United States Patent
Hession et al.

(10) Patent No.: US 6,307,025 B1
(45) Date of Patent: Oct. 23, 2001

(54) VCAM FUSION PROTEINS AND DNA CODING THEREFOR

(75) Inventors: Catherine A. Hession, South Weymouth; Roy R. Lobb, Westwood; Susan E. Goelz, Winchester; Laurelee Osborn, Brighton; Christopher D. Benjamin, Beverly; Margaret D. Rosa, Winchester, all of MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 08/482,073

(22) Filed: Jun. 7, 1995

Related U.S. Application Data

(62) Division of application No. 08/342,642, filed on Nov. 21, 1994, now abandoned, which is a continuation of application No. 07/608,298, filed on Oct. 31, 1990, now abandoned, which is a continuation-in-part of application No. PCT/US90/02357, filed on Apr. 29, 1990, and a continuation-in-part of application No. 07/452,675, filed on Dec. 18, 1989, now Pat. No. 5,272,263, which is a continuation-in-part of application No. 07/359,516, filed on Jun. 1, 1989, now abandoned, which is a continuation-in-part of application No. 07/345,151, filed on Apr. 28, 1989, now Pat. No. 5,217,810.

(51) Int. Cl.[7] .................. C07K 16/46; C07K 14/705; C12N 15/00; C12N 15/11
(52) U.S. Cl. ...................... 530/387.3; 424/134.1; 424/192.1; 435/252.3; 435/320.1; 435/471; 435/476; 530/350; 536/23.1; 536/23.4; 536/23.5; 536/23.53
(58) Field of Search ................. 435/172.3, 69.1, 435/310.1, 471, 476, 252.3; 530/350, 387.3; 536/23.1, 23.4, 23.5, 23.53; 424/134.1, 192.1

(56) References Cited

U.S. PATENT DOCUMENTS

| | | |
|---|---|---|
| 4,752,569 | 6/1988 | Terasaki et al. . |
| 5,011,778 | 4/1991 | Newman et al. . |
| 5,098,833 | * 3/1992 | Lasky et al. .................. 435/69.1 |

FOREIGN PATENT DOCUMENTS

| | | |
|---|---|---|
| 3 642 096 | 12/1986 | (DK) . |
| 0 330 506 | 8/1989 | (EP) . |
| 0 408 859 | 1/1991 | (EP) . |
| WO 95/19790 | 7/1995 | (WO) . |

OTHER PUBLICATIONS

Arfors, K.-E., et al., "A Monoclonal Antibody to the Membrane Glycoprotein Complex CD18 Inhibits Polymorphonuclear Leukocyte Accumulation and Plasma Leakage In Vivo", *Blood*, 69, pp. 338–340 (1987).
Aruffo, A., and B. Seed, "Molecular Cloning of a CD28 cDNA by a High Efficiency COS Cell Expression System", *Proc. Natl. Acad. Sci. USA*, 84, pp. 8573–8577 (1987).
Becker, D., et al., "Proliferation of Human Malignant Melanomas Is Inhibited by Antisense Oligodeoxynucleotides Targeted Against Basic Fibroblast Growth Factor", *EMBO J.*, 8, pp. 3685–3691 (1989).
Benchimol, S., et al., "Carcinoembryonic Antigen, A Human Tumor Marker, Functions as an Intercellular Adhesion Molecule", *Cell*, 57, pp. 327–334 (1989).
Bevilacqua, M.P., et al., "Identification of an Inducible Endothelial–Leukocyte Adhesion Molecule (E–LAM 1) Using Monoclonal Antibodies (Mab)", *Fed. Amer. Soc. Exper. Biol.*, 71st Annual Meeting, Abstr. #514, p. 505 (1987).
Bevilacqua, M.P., et al., "Identification of an Inducible Endothelial–Leukocyte Adhesion Molecule", *Proc. Natl. Acad. Sci. USA*, 84, pp. 9238–9242 (1987b).
Bevilacqua, M.P., et al., "Endothelial Leukocyte Adhesion Molecule 1: An Inducible Receptor for Neutrophils Related to Complement Regulatory Proteins and Lectins", *Science*, 243, pp. 1160–1165 (1989).
Bevilacqua, M.P., et al., "Interleukin 1 Acts on Cultured Human Vascular Endothelium to Increase the Adhesion of Polymorphonuclear Leukocytes, Monocytes, and Related Leukocyte Cell Lines", *J. Clin. Invest.*, 76, pp. 2003–2011 (1985).
Bevilacqua, M.P., et al., "Endothelial–Dependent Mechanisms of Leukocyte Adhesion: Regulation by Interleukin–1 and Tumor Necrosis Factor", *Leukocyte Emigration and Its Sequelae* (S. Karger A.G., Switzerland, 1987a), pp. 79–93.
Bevilacqua, M.P., and M.A. Gimbrone, "Inducible Endothelial Functions in Inflammation and Coagulation", *Seminars in Thrombosis and Hemostasis*, 13, pp. 425–433 (1987).
Breathnach, R. and P. Chambon, "Organization and Expression of Eucaryotic Split Genes Coding for Proteins", *Ann. Rev. Biochem.*, 50, pp. 349–383 (1981).
Brenan, M. and C.R. Parish, "Intracellular Fluorescent Labelling of Cells for Analysis of Lymphocyte Migration", *J. Immun. Meth.*, 74, pp. 31–38 (1984).
Capon, D.J., et al., "Designing CD4 Immunoadhesins for AIDS Therapy", *Nature*, 337, pp. 525–531 (1989).
Carlsson, R., and C. Glad, "Monoclonal Antibodies into the '90s", *Bio/Technology*, 7, pp. 567–573 (Jun. 1989).
Cate, R., et al., "Isolation of the Bovine and Human Genes for Mullerian Inhibiting Substance and Expression of the Human Gene in Animal Cells", *Cell*, 45, pp. 685–698 (1986).
Cech, T.R., "Ribozymes and Their Medical Implications", *J. Amer. Med. Assn.*, 260, pp. 3030–3034 (1988).
Chang et al., "Recombination Following Transformation of *Escherichia coli* by Heteroduplex Plasmid DNA Molecules", *Gene*, 29, pp. 255–261 (1984).

(List continued on next page.)

Primary Examiner—Phillip Gambel
(74) Attorney, Agent, or Firm—Warren A. Kaplan; Biogen, Inc.

(57) ABSTRACT

VCAM fusion proteins capable of binding to VLA4, and DNA molecules coding on these fusions.

7 Claims, 15 Drawing Sheets

OTHER PUBLICATIONS

Chen, Y.P., et al., "Molecular Cloning and Characterization of Two Rat Renal Kallikrein Genes", *Biochemistry*, 27, pp. 7189–7196 (1988).

Colley, K.J., et al., "Conversion of a Golgi Apparatus Sialyltransferase to a Secretory Protein by Replacement of the NH$_2$–terminal Signal Anchor with a Signal Peptide", *J. Biol. Sci.*, 264, pp. 17619–17622 (1989).

Cotran, R.S., and J.S. Pober, "Endothelial Activation: Its Role in Inflammatory and Immune Reactions", in *Endothelial Cell Biology*, Simionescu and Simionescu, Eds., Plenum Press, New York (1988), pp. 335–347.

Cotran, R.S., et al., "Induction and Detection of a Human Endothelial Activation Antigen In Vivo", *J. Exp. Med.*, 164, pp. 661–666 (1986).

Dana, N., et al., "Mo1 Surface Glycoprotein: Structure, Function and Clinical Importance", *Pathol. Immunopathol. Res.*, 5, pp. 371–383 (1986).

Davis, M.M., et al., "Cell Type–Specific cDNA Probes and the Murine I Region: The Localization and Orientation of Ad", *Proc. Natl. Acad. Sci. USA*, 81, pp. 2194–2198 (1984).

Davis, M.M., "Subtractive cDNA Hybridization and the T–cell Receptor Gene", *Handbook of Experimental Immunology In Four Volumes*, 4th ed. Blackwell Scientific Publications, Oxford, England (1986), pp. 76.1–76.13.

Devereux, J., et al., "A Comprehensive Set of Sequence Analysis Programs for the VAX", *Nucl. Acids Res.*, 12, pp. 387–395 (1984).

Dixon, L., et al., "Evidence For Replicative Recombination In Cauliflower Mosaic Virus", *Virology*, 150, pp. 463–468 (1986).

Duguid, J.R., et al., "Isolation of cDNAs of Scrapie–Modulated RNAs by Subtractive Hybridization of a cDNA Library", *Proc. Natl. Acad. Sci. USA*, 85, pp. 5738–5742 (1988).

Dustin, M.L., et al., Induction by IL1 and Interferon–gamma: Tissue Distribution, Biochemistry, and Function of a Natural Adherence Molecule (ICAM–1), *J. Immunol.*, 137, pp. 245–254 (1986).

Dustin, M.L., and T.A. Springer, "Lymphocyte Function–Associated Antigen–1 (LFA–1) Interaction with Intercellular Adhesion Molecule 1 (ICAM1) Is One of at Least Three Mechanisms for Lymphocyte Adhesion to Cultured Endothelial Cells", *J. Cell. Biol.*, 107, pp. 321–333 (1988).

Elices, M.S., et al., "VCAM–1 on Activated Endothelium Interacts with the Leukocyte Integrin VLA–4 at a Site Distinct from the VLA–4 Fibronectin Binding Site", *Cell*, 60, pp. 577–584 (1990).

Ellison, J.W., et al., "The Sequence of a Human Immunoglobulin C–gamma–1 Gene", *Nucl. Acids Res.*, 10, pp. 4071–4079 (1982).

Feinberg, A.P., and B. Vogelstein, "A Technique for Radiolabeling DNA Restriction Endonuclease Fragments to High Specific Activity", *Anal. Biochem.*, 132, pp. 6–13 (1983).

Feinberg, A.P., and B. Vogelstein, "A Technique for Radiolabeling DNA Restriction Endonuclease Fragments to High Specific Activity", *Anal. Biochem.*, 137, pp. 266–267 (1984).

Fisher, R.A., et al., "HIV Infection Is Blocked In Vitro by Recombinant Soluble CD4", *Nature*, 331, pp. 76–78 (1988).

Gimbrone, M.A., "Culture of Vascular Endothelium", *Prog. Hemostasis Thromb.*, 3, pp. 1–28 (1976).

Goldenberg, D.M., "Targeted Cancer Treatment", *Immunology Today*, 10, pp. 286–288 (1989).

Grau, G.E., et al., "Monoclonal Antibody Against Interferon Gamma Can Prevent Experimental Cerebral Malaria and Its Associated Overproduction of Tumor Necrosis Factor", *Proc. Natl. Acad. Sci., USA*, 86, pp. 5572–5574 (1989).

Gubler, U. and Hoffman, B.J., "A Simple and Very Efficient Method for Generating cDNA Libraries", *Gene*, 25, pp. 263–269 (1983).

Hambor, J.E., et al., "Functional Consequences of Anti–Sense RNA–Mediated Inhibition of CD8 Surface Expression in a Human T Cell Clone", *J. Exp. Med.*, 168, pp. 1237–1245 (1988).

Harlan, J.M., et al., "The Role of Neutrophil Membrane Proteins in Neutrophil Emigration", in *Leukocyte Emigration and Its Sequelae*, H. Movat, ed. (S. Karger AG, Basel, Switzerland, 1987), pp. 94–104.

Harlan, J.M., "Neutrophil–Mediated Vascular Injury", *Acta Med. Scand., Suppl.*, 715, pp. 123–129 (1987).

Harlan, J.M., "Leukocyte–Endothelial Interactions", *Blood*, 65, pp. 513–525 (1985).

Haselhoff, J., and W.L. Gerlach, "Simple RNA Enzymes with New and Highly Specific Endoribonuclease Activities", *Nature*, 334, pp. 585–591 (1988).

Hedrick, S.M., et al., "Isolation of cDNA Clones Encoding T Cell–Specific Membrane–Associated Proteins", *Nature*, 308, pp. 149–153 (1984).

Hemler, M.E., et al., "The VLA Protein Family (Characterization of Five Distinct Cell Surface Heterodimers Each with a Common 130,000 Molecular Weight Subunit)", *J. Biol. Chem.*, 262, pp. 3300–3309 (1987a).

Hemler, M.E., et al., "Characterization of the Cell Surface Heterodimer VLA–4 and Related Peptides", *J. Biol. Chem.*, 262, pp. 11478–11485 (1987b).

Hemler, M.E., "Adhesion Protein Receptors on Hematopoietic Cells", *Immunol. Today*, 9, pp. 109–113 (1988).

Hession, C., et al., "Endothelial Leukocyte Adhesion Molecule 1: Direct Expression Cloning and Functional Interactions", *Proc. Natl. Acad. Sci., USA*, 87, pp. 1673–1677 (1990).

Hirt, B., "Selective Extraction of Polyoma DNA from Infected Mouse Cell Cultures", *J. Mol. Biol.*, 26, pp. 365–369 (1967).

Hough, A. and L. Sokoloff, "Pathology", Chap. 4, *Rheumatoid Arthritis*, P.D. Ustinger, N.J. Zugifler, and Ehrlich, G.E., eds., (Lippencott, Philadelphia, 1985), pp. 49–69.

Hunkapiller, T. and L. Hood, "Diversity of the Immunoglobulin Gene Superfamily", *Adv. Immunol.*, 44, pp. 1–63 (1989).

Huse, W.D., et al., "Generation of a Large Combinatorial Library of the Immunoglobulin Repertoire in Phage Lambda", *Science*, 246, pp. 1275–1281 (1989).

Hynes, R.O., "Integrins: A Family of Cell Surface Receptors", *Cell*, 48, pp. 549–554 (1987).

Kalderon et al., "Deletion Loop Mutagenesis: A Novel Method for the Construction of Point Mutations Using Deletion Mutants", *Nucl. Acids Res.*, 10, pp. 5161–5171 (1982).

Kennedy, R.C., et al., "Anti–idiotypes and Immunity", *Sci. Am.*, 255, pp. 48–56 (Jul. 1986).

Kukowska–Latallo, J.F., et al., "A Cloned Human cDNA Determines Expression of a Mouse Stage–specific Embryonic Antigen and the Lewis Blood Group α(1,3/1,4)Fucosyltransferase", *Genes and Development,* 4, pp. 1288–1303 (1990).

Kurzinger, K., et al., "A Novel Lymphocyte Function–Associated Antigen (LFA–1): Cellular Distribution, Quantitative Expression, and Structure", *J. Immunol.,* 127, pp. 596–602 (1981).

Larsen, R.D., et al., "Molecular Cloning, Sequence, and Expression of a Human GPD–L–Fucose: –D–Galactoside 2–α–L–Fucosyltransferase cDNA That Can Form the H Blood Group Antigen", *Proc. Natl. Acad. Sci. USA,* 87, pp. 6674–6678 (1990).

Lehrach, H., et al., "RNA Molecular Weight Determinations by Gel Electrophoresis under Denaturing Conditions, a Critical Reexamination", *Biochem.,* 16, pp. 4743–4751 (1977).

Lenardo, M.J. and D. Baltimore, "NF–KB: A Pleiotropic Mediator of Inducible and Tissue Specific Gene Control", *Cell,* 58, pp. 227–230 (1989).

Lowe, J.B., et al., "ELAM–1 Dependent Cell Adhesion to Vascular Endothelium Determined by a Transfected Human Fucosyl–Transferase cDNA", *Cell,* 63, pp. 475–484 (1990).

Lundwall, A.B., et al., "Isolation and Sequence Analysis of a cDNA Clone Encoding The Fifth Complement Component", *J. Biol. Chem.,* 260, pp. 2108–2112 (1985).

Luscinskas, F.E., et al., "Endothelial–Leukocyte Adhesion Molecule–1 Dependent and Leukocyte (CD11/CD18) Dependent Mechanisms Contribute to Polymorphonuclear Leukocyte Adhesion to Cytokine Activated Human Vascular Epithelium", *J. Immunol.,* 142(7), pp. 2257–2263 (1989).

Malech, H.L. and Gallin, J.I., "Neutrophils in Human Diseases", *N. Eng. J. Med.,* 317, pp. 687–694 (1987).

Marcantonio, E.E., and R.O. Hynes, "Antibodies to the Conserved Cytoplasmic Domain of the Integrin β–1 Subunit React with Proteins in Vertebrates, Invertebrates and Fungi", *J. Cell. Biol,* 106, pp. 1765–1772 (1988).

Marcus–Sekura, C.J., "Techniques for Using Antisense Oligonucleotides to Study Gene Expression", *Anal. Biochem.,* 172, pp. 289–295 (1988).

Marlin, S.D., and T.A. Springer, "Purified Intercellular Adhesion Molecule–1 (ICAM–1) Is a Ligand for Lymphocyte Function–Associated Antigen 1 (LFA–1)", *Cell,* 51, pp. 813–819 (1987).

Maxam, A. and W. Gilbert, "Sequencing End–Labeled DNA with Base–Specific Chemical Cleavages", *Methods in Enzymol.,* 65, pp. 499–560 (1980).

Mohamed, A.H., et al., "Primary Structure of the Multifunctional α–Subunit Protein of Yeast Fatty Acid Synthase Derived from FAS2 Gene Sequence", *J. Biol. Chem.,* 263, pp. 12315–12325 (1988).

Morinaga et al., "Improvement of Oligonucleotide–Directed Site–Specific Mutagenesis Using Double–Stranded Plasmid DNA", *Bio/Technology,* 2, pp. 636–639 (1984).

Oostra et al., "Transforming Activity of Polyoma Virus Middle–T Antigen Probed by Site–Directed Mutagenesis", *Nature,* 304, pp. 456–460 (1983).

Osborn, L., et al., "Tumor Necrosis Factor α and Interleukin 1 Stimulate the Human Immunodeficiency Virus Enhancer by Activation of the Nucleus Factor κB", *Proc. Natl. Acad. Sci., U.S.A.,* 86, pp. 2336–2340 (1989).

Osborn, et al., "Direct Expression Cloning of Vascular Cell Adhesion Molecule 1, A Cytokine–Induced Endothelial Protein that Binds to Lymphocytes", *Cell,* 59, pp. 1203–1212 (1989).

Palcic, M.M., et al., "A Bisubstrate Analogue Inhibitor for α (1–2)–Fucosyltransferase", *J. Biol. Chem.,* 264, pp. 17177–17178 (1989).

Paulson, J.C., and K.J. Colley, "Glycosyltransferases: Structure, Localization, and Control of Cell Type–specific Glycosylation", *J. Biol. Chem.,* 264, pp. 17615–17618 (1989).

Peden, K.W.C. and D. Nathans, "Local Mutagenesis Within Deletion Loops of DNA Heteroduplexes", *Proc. Natl. Acad. Sci., U.S.A.,* 79, 7214–7217 (1982).

Pober, J.S., et al., "Overlapping Patterns of Activation of Human Endothelial Cells by Interleukin 1, Tumor Necrosis Factor, and Immune Interferon", *J. Immunol.,* 137, pp. 1895–1896 (1986).

Potvin, B., et al., "Transfection of a Human alpha–(1,3) Fucosyltransferase Gene Into Chinese Hamster Ovary Cells", *J. Biol. Chem.,* 265, pp. 1615–1616 (1990).

Ross, R., "The Pathogenesis of Atherosclerosis—An Update", *N. Eng. J. Med,* 314, pp. 488–500 (1986).

Rothlein, R., et al., "A Human Intercellular Adhesion Molecule (ICAM–1) Distinct from LFA–1", *J. Immunol.,* 137, pp. 1270–1274 (1986).

Ruoslahti, E., "Fibronectin and its Receptors", *Ann. Rev. Biochem.,* 57, pp. 375–413 (1988).

Sambrook, J., et al., "In Vitro Amplification of DNA by Polymerase Chain Reaction", Chapter 14 in *Molecular Cloning, A Laboratory Manual,* Cold Spring Harbor Laboratory Press, Cold Spring Harbor, New York (1989), pp. 14.1–14.35.

Sandri–Goldin, R.M., et al., "High Frequency Transfer of Cloned Herpes Simplex Virus Type 1 Sequences to Mammalian Cells by Protoplast Fusion", *Molec. and Cell Biol.,* 1, pp. 743–752 (1981).

Sargent, T.D., "Isolation of Differentially Expressed Genes", *Methods in Enzymol.,* 152, pp. 432–447 (1987).

Sato, K., et al., "A Specific DNA Sequence Controls Termination of Transcription in the Gastrin Gene", *Molec. and Cell Biol.,* 6, pp. 1032–1043 (1986).

Schneider, C., et al., "A One–Step Purification of Membrane Proteins Using a High Efficiency Immunomatrix", *J. Biol. Chem.,* 257, pp. 10766–10769 (1982).

Schwartz, B.R., et al., "Identification of Surface Proteins Mediating Adherence of CD11/CD18—Deficient Lymphoblastoid Cells to Cultured Human Endothelium", *J. Clin. Invest.,* 85, pp. 2019–2022 (1990).

Seed, B., "An LFA–3 cDNA Encodes a Phospholipid–Linked Membrane Protein Homologous to Its Receptor CD2", *Nature,* 329, pp. 840–842 (1987).

Seed, B. and A. Aruffo, "Molecular Cloning of the CD2 Antigen, the T–cell Erythrocyte Receptor, by a Rapid Immunoselection Procedure", *Proc. Natl. Acad. Sci. USA,* 84, pp. 3365–3369 (1987).

Simmons et al., "ICAM, an Adhesion Ligand of LFA–1, Is Homologous to the Neural Cell Adhesion Molecule NCAM", *Nature,* 331, pp. 624–647 (1988).

Skerra, A. and A. Plückthun, "Assembly of a Functional Immunoglobulin $F_v$ Fragment in *Escherichia coli*", *Science,* 240, pp. 1038–1043 (1988).

Smith, C.W., et al., "Cooperative Interactions of LFA–1 and Mac–1 with Intercellular Adhesion Molecule 1 in Facilitating Adherence and Transendothelial Cell Migration of Human Neutrophils in Vitro", *J. Clin. Invest.,* 83, pp. 2008–2017 (1989).

Springer, T.A., et al., "The Lymphocyte Function–Associated LFA–1, CD2, and LFA–3 Molecules: Cell Adhesion Receptors of the Immune System", *Ann. Rev. Immunol.,* 5, pp. 223–252 (1987).

Staunton, D.E., et al., "Primary Structure of ICAM–1 Demonstrates Interaction Between Members of the Immunoglobulin and Integrin Supergene Families", *Cell,* 52, pp. 925–933 (1988).

Subramani, S., et al., "Expression of the Mouse Dihydrofolate Reductase Complementary Deoxyribonucleic Acid in Simian Virus 40 Vectors", *Molec. Cell. Biol.,* 1, pp. 854–864 (1981).

Takada, Y., and M.E. Hemler, "The Primary Structure of the VLA–2/Collagen Receptor $\alpha^2$ Subunit (Platelet GP Ia): Homology to Other Integrins and the Presence of a Possible Collagen–Binding Domain", *J. Cell. Biol.,* 109, pp. 397–407 (1989).

Takada, Y., et al., "The Primary Structure of the $\alpha 4$ Subunit of VLA–4: Homology to Other Integrins and a Possible Cell–Cell Adhesion Function", *EMBO J.,* 8, pp. 1361–1368 (1989).

Thomas, H. and Sikora, K., "Biological Approaches to Cancer Therapy", *J. Intl. Med. Res.,* 17, pp. 191–204 (1989).

Todd III, R.F., et al., "The Anti–Inflammatory Properties of Monoclonal Anti–Mol (CD11B/CD18) Antibodies in Vitro and in Vivo", in *Structure and Function of Molecules Involved in Leukocyte Adhesion,* Chapter 9, pp. 125–137 Rosenthal et al., Eds., Springer–Verlag, New York (1989).

Vedder, N.B., et al., "A Monoclonal Antibody to the Adherence–Promoting Leukocyte Glycoprotein, CD18, Reduces Organ Injury and Improves Survival from Hemorrhagic Shock and Resuscitation in Rabbits", *J. Clin. Invest.,* 81, pp. 939–944 (1988).

von Heijne, G., "A Method for Predicting Signal Sequence Cleavage Sites", *Nucl. Acids Res.,* 14, pp. 4693–90 (1986).

Wallis, W.J., and J.M. Harlan, "Effector Functions of Endothelium in Inflammatory and Immunologic Reactions", *Pathol. Immunopathol. Res.,* 5, pp. 73–103 (1986).

Walz, G., et al., "Recognition by ELAM–1 of the Sialyl–Le$^x$ Determinant on Myeloid and Tumor Cells", *Science,* 250, pp. 1132–1135 (1990).

Ward, E.S., et al., "Binding Activities of a Repertoire of Single Immunoglobulin Variable Domains Secreted from *Escherichia coli*", *Nature,* 341, pp. 544–546 (1989).

Warrick, H.M., et al., "Conserved Protein Domains in a Myosin Heavy Chain Gene From *Dictyostelium Discoideum*", *Proc. Natl. Acad. Sci., USA,* 83, pp. 9433–9437 (1986).

Wayner, E.A., et al., "Identification and Characterization of the Lymphocyte Adhesion Receptor for an Alternative Cell Attachment Domain in Plasma Fibronectin", *J. Cell. Biol.,* 109: 1321–1330, (1989).

Weintraub, H.M., "Antisense RNA and DNA", *Sci. Am.,* 262, pp. 40–46 (Jan. 1990).

Wheeler, M.E., et al., "Cultured Human Endothelial Cells Stimulated with Cytokines or Endotoxin Produce an Inhibitor of Leukocyte Adhesion", *J. Clin. Invest.,* 82, pp. 1211–1218 (1988).

White, J. and D. Littman, "Viral Receptors of the Immunoglobulin Superfamily", *Cell,* 56, pp. 725–728 (1989).

Williams, A. and Barclay, A.N., "The Immunoglobulin Superfamily—Domains for Cell Surface Recognition", *Ann. Rev. Immunol.,* 6, pp. 381–405 (1988).

Wong, C.–H., "Enzymatic Catalysts in Organic Synthesis", *Science,* 244, pp. 1145–1152 (1989).

Wysocki, L.J. and V.L. Sato, "'Panning' for Lymphocytes: A Method for Cell Selection", *Proc. Natl. Acad. Sci. USA,* 75, pp. 2844–2848 (1978).

Yamasaki, K., et al., "Cloning and Expression of the Human Interleukin–6 (BSF–2/IFNB2) Receptor", *Science,* 241, pp. 825–828 (1988).

Young, R.A. and R.W. Davis, "Efficient Isolation of Genes by Using Antibody Probes", *Proc. Natl. Acad. Sci. USA,* 80, pp. 1194–1198 (1983).

Young, R.A. and R.W. Davis, "Yeast RNA Polymerase II Genes: Isolation with Antibody Probes", *Science,* 222, pp. 778–782 (1984).

Rice et al Science 246: 1303–1306(1989).*

Pepinsky et al. J. Biol. Chem. 267: 17820–17826(1992).*

Graber et al. J. Immunol. 145: 819–830(1990).*

Polte et al. Nuc. Acids. Res. 18: 5901 (1990).*

* cited by examiner

```
  1  TTCACATCAAAACTCCTATACTGACCTGAGACAGAGGCAGCAGTGATACC            50

51  CACCTGAGAGATCCTGTGTTTGAACAACTGCTTCCCAAAACGGAAAGTAT           100

101  TTCAAGCCTAAACCTTTGGGTGAAAGAACTCTTGAAGTCATGATTGCTT            150
                                                 MetIleAlaS

151  CACAGTTTCTCTCAGCTCTCACTTTGGTGCTTCTCATTAAAGAGAGTGGA           200
     erGlnPheLeuSerAlaLeuThrLeuValLeuLeuIleLysGluSerGly

201  GCCTGGTCTTACAACACCTCCACGGAAGCTATGACTTATGATGAGGCCAG           250
     AlaTrpSerTyrAsnThrSerThrGluAlaMetThrTyrAspGluAlaSe

251  TGCTTATTGTCAGCAAAGGTACACACACCTGGTTGCAATTCAAAACAAAG           300
     rAlaTyrCysGlnGlnArgTyrThrHisLeuValAlaIleGlnAsnLysG

301  AAGAGATTGAGTACCTAAACTCCATATTGAGCTATTCACCAAGTTATTAC           350
     luGluIleGluTyrLeuAsnSerIleLeuSerTyrSerProSerTyrTyr

351  TGGATTGGAATCAGAAAAGTCAACAATGTGTGGGTCTGGGTAGGAACCCA           400
     TrpIleGlyIleArgLysValAsnAsnValTrpValTrpValGlyThrGl

401  GAAACCTCTGACAGAAGAAGCCAAGAACTGGGCTCCAGGTGAACCCAACA           450
     nLysProLeuThrGluGluAlaLysAsnTrpAlaProGlyGluProAsnA

451  ATAGGCAAAAAGATGAGGACTGCGTGGAGATCTACATCAAGAGAGAAAAA           500
     snArgGlnLysAspGluAspCysValGluIleTyrIleLysArgGluLys

501  GATGTGGGCATGTGGAATGATGAGAGGTGCAGCAAGAAGAAGCTTGCCCT           550
     AspValGlyMetTrpAsnAspGluArgCysSerLysLysLysLeuAlaLe

551  ATGCTACACAGCTGCCTGTACCAATACATCCTGCAGTGGCCACGGTGAAT           600
     uCysTyrThrAlaAlaCysThrAsnThrSerCysSerGlyHisGlyGluC

601  GTGTAGAGACCATCAATAATTACACTTGCAAGTGTGACCCTGGCTTCAGT           650
     ysValGluThrIleAsnAsnTyrThrCysLysCysAspProGlyPheSer

651  GGACTCAAGTGTGAGCAAATTGTGAACTGTACAGCCCTGGAATCCCCTGA           700
     GlyLeuLysCysGluGlnIleValAsnCysThrAlaLeuGluSerProGl

701  GCATGGAAGCCTGGTTTGCAGTCACCCACTGGGAAACTTCAGCTACAATT           750
     uHisGlySerLeuValCysSerHisProLeuGlyAsnPheSerTyrAsnS

751  CTTCCTGCTCTATCAGCTGTGATAGGGGTTACCTGCCAAGCAGCATGGAG           800
     erSerCysSerIleSerCysAspArgGlyTyrLeuProSerSerMetGlu
```

FIG. 1A

```
801   ACCATGCAGTGTATGTCCTCTGGAGAATGGAGTGCTCCTATTCCAGCCTG      850
      ThrMetGlnCysMetSerSerGlyGluTrpSerAlaProIleProAlaCy

851   CAATGTGGTTGAGTGTGATGCTGTGACAAATCCAGCCAATGGGTTCGTGG      900
      sAsnValValGluCysAspAlaValThrAsnProAlaAsnGlyPheValG

901   AATGTTTCCAAAACCCTGGAAGCTTCCCATGGAACACAACCTGTACATTT      950
      luCysPheGlnAsnProGlySerPheProTrpAsnThrThrCysThrPhe

951   GACTGTGAAGAAGGATTTGAACTAATGGGAGCCCAGAGCCTTCAGTGTAC      1000
      AspCysGluGluGlyPheGluLeuMetGlyAlaGlnSerLeuGlnCysTh

1001  CTCATCTGGGAATTGGGACAACGAGAAGCCAACGTGTAAAGCTGTGACAT      1050
      rSerSerGlyAsnTrpAspAsnGluLysProThrCysLysAlaValThrC

1051  GCAGGGCCGTCCGCCAGCCTCAGAATGGCTCTGTGAGGTGCAGCCATTCC      1100
      ysArgAlaValArgGlnProGlnAsnGlySerValArgCysSerHisSer

1101  CCTGCTGGAGAGTTCACCTTCAAATCATCCTGCAACTTCACCTGTGAGGA      1150
      ProAlaGlyGluPheThrPheLysSerSerCysAsnPheThrCysGluGl

1151  AGGCTTCATGTTGCAGGGACCAGCCCAGGTTGAATGCACCACTCAAGGGC      1200
      uGlyPheMetLeuGlnGlyProAlaGlnValGluCysThrThrGlnGlyG

1201  AGTGGACACAGCAAATCCCAGTTTGTGAAGCTTTCCAGTGCACAGCCTTG      1250
      lnTrpThrGlnGlnIleProValCysGluAlaPheGlnCysThrAlaLeu

1251  TCCAACCCCGAGCGAGGCTACATGAATTGTCTTCCTAGTGCTTCTGGCAG      1300
      SerAsnProGluArgGlyTyrMetAsnCysLeuProSerAlaSerGlySe

1301  TTTCCGTTATGGGTCCAGCTGTGAGTTCTCCTGTGAGCAGGGTTTTGTGT      1350
      rPheArgTyrGlySerSerCysGluPheSerCysGluGlnGlyPheValL

1351  TGAAGGGATCCAAAAGGCTCCAATGTGGCCCCACAGGGGAGTGGGACAAC      1400
      euLysGlySerLysArgLeuGlnCysGlyProThrGlyGluTrpAspAsn

1401  GAGAAGCCCACATGTGAAGCTGTGAGATGCGATGCTGTCCACCAGCCCCC      1450
      GluLysProThrCysGluAlaValArgCysAspAlaValHisGlnProPr

1451  GAAGGGTTTGGTGAGGTGTGCTCATTCCCCTATTGGAGAATTCACCTACA      1500
      oLysGlyLeuValArgCysAlaHisSerProIleGlyGluPheThrTyrL

1501  AGTCCTCTTGTGCCTTCAGCTGTGAGGAGGGATTTGAATTACATGGATCA      1550
      ysSerSerCysAlaPheSerCysGluGluGlyPheGluLeuHisGlySer

1551  ACTCAACTTGAGTGCACATCTCAGGGACAATGGACAGAAGAGGTTCCTTC      1600
      ThrGlnLeuGluCysThrSerGlnGlyGlnTrpThrGluGluValProSe
```

FIG. 1B

| | | |
|---|---|---|
| 1601 | CTGCCAAGTGGTAAAATGTTCAAGCCTGGCAGTTCCGGGAAAGATCAACA<br>rCysGlnValValLysCysSerSerLeuAlaValProGlyLysIleAsnM | 1650 |
| 1651 | TGAGCTGCAGTGGGGAGCCCGTGTTTGGCACTGTGTGCAAGTTCGCCTGT<br>etSerCysSerGlyGluProValPheGlyThrValCysLysPheAlaCys | 1700 |
| 1701 | CCTGAAGGATGGACGCTCAATGGCTCTGCAGCTCGGACATGTGGAGCCAC<br>ProGluGlyTrpThrLeuAsnGlySerAlaAlaArgThrCysGlyAlaTh | 1750 |
| 1751 | AGGACACTGGTCTGGCCTGCTACCTACCTGTGAAGCTCCCACTGAGTCCA<br>rGlyHisTrpSerGlyLeuLeuProThrCysGluAlaProThrGluSerA | 1800 |
| 1801 | ACATTCCCTTGGTAGCTGGACTTTCTGCTGCTGGACTCTCCCTCCTGACA<br>snIleProLeuValAlaGlyLeuSerAlaAlaGlyLeuSerLeuLeuThr | 1850 |
| 1851 | TTAGCACCATTTCTCCTCTGGCTTCGGAAATGCTTACGGAAAGCAAAGAA<br>LeuAlaProPheLeuLeuTrpLeuArgLysCysLeuArgLysAlaLysLy | 1900 |
| 1901 | ATTTGTTCCTGCCAGCAGCTGCCAAAGCCTTGAATCAGATGGAAGCTACC<br>sPheValProAlaSerSerCysGlnSerLeuGluSerAspGlySerTyrG | 1950 |
| 1951 | AAAAGCCTTCTTACATCCTTTAAGTTCAAAAGAATCAGAAACAGGTGCAT<br>lnLysProSerTyrIleLeu | 2000 |
| 2001 | CTGGGGAACTAGAGGGATACACTGAAGTTAACAGAGACAGATAACTCTCC | 2050 |
| 2051 | TCGGGTCTCTGGCCCTTCTTGCCTACTATGCCAGATGCCTTTATGGCTGA | 2100 |
| 2101 | AACCGCAACACCCATCACCACTTCAATAGATCAAAGTCCAGCAGGCAAGG | 2150 |
| 2151 | ACGGCCTTCAACTGAAAAGACTCAGTGTTCCCTTTCCTACTCTCAGGATC | 2200 |
| 2201 | AAGAAAGTGTTGGCTAATGAAGGGAAAGGATATTTTCTTCCAAGCAAAGG | 2250 |
| 2251 | TGAAGAGACCAAGACTCTGAAATCTCAGAATTCCTTTTCTAACTCTCCCT | 2300 |
| 2301 | TGCTCGCTGTAAAATCTTGGCACAGAAACACAATATTTTGTGGCTTTCTT | 2350 |
| 2351 | TCTTTTGCCCTTCACAGTGTTTCGACAGCTGATTACACAGTTGCTGTCAT | 2400 |
| 2401 | AAGAATGAATAATAATTATCCAGAGTTTAGAGGAAAAAAATGACTAAAAA | 2450 |
| 2451 | TATTATAACTTAAAAAATGACAGATGTTGAATGCCCACAGGCAAATGCAT | 2500 |
| 2501 | GGAGGGTTGTTAATGGTGCAAATCCTACTGAATGCTCTGTGCGAGGGTTA | 2550 |
| 2551 | CTATGCACAATTTAATCACTTTCATCCCTATGGGATTCAGTGCTTCTTAA | 2600 |

FIG. 1C

```
2601  AGAGTTCTTAAGGATTGTGATATTTTACTTGCATTGAATATATTATAAT  2650
2651  CTTCCATACTTCTTCATTCAATACAAGTGTGGTAGGGACTTAAAAAACTT  2700
2701  GTAAATGCTGTCAACTATGATATGGTAAAAGTTACTTATTCTAGATTACC  2750
2751  CCCTCATTGTTTATTAACAAATTATGTTACATCTGTTTTAAATTTATTTC  2800
2801  AAAAAGGGAAACTATTGTCCCCTAGCAAGGCATGATGTTAACCAGAATAA  2850
2851  AGTTCTGAGTGTTTTACTACAGTTGTTTTTGAAAACATGGTAGAATTG    2900
2901  GAGAGTAAAAACTGAATGGAAGGTTTGTATATTGTCAGATATTTTTCAG   2950
2951  AAATATGTGGTTTCCACGATGAAAACTTCCATGAGGCCAAACGTTTTGA   3000
3001  ACTAATAAAAGCATAAATGCAAACACACAAAGGTATAATTTTATGAATGT  3050
3051  CTTTGTTGGAAAAGAATACAGAAAGATGGATGTGCTTTGCATTCCTACAA  3100
3101  AGATGTTTGTCAGATATGATATGTAAACATAATTCTTGTATATTATGGAA  3150
3151  GATTTTAAATTCACAATAGAAACTCACCATGTAAAAGAGTCATCTGGTAG  3200
3201  ATTTTTAACGAATGAAGATGTCTAATAGTTATTCCCTATTTGTTTCTTC   3250
3251  TGTATGTTAGGGTGCTCTGGAAGAGAGGAATGCCTGTGTGAGCAAGCATT  3300
3301  TATGTTTATTTATAAGCAGATTTAACAATTCCAAAGGAATCTCCAGTTTT  3350
3351  CAGTTGATCACTGGCAATGAAAAATTCTCAGTCAGTAATTGCCAAAGCTG  3400
3401  CTCTAGCCTTGAGGAGTGTGAGAATCAAAACTCTCCTACACTTCCATTAA  3450
3451  CTTAGCATGTGTTGAAAAAAAGTTTCAGAGAAGTTCTGGCTGAACACTG   3500
3501  GCAACAACAAAGCCAACAGTCAAAACAGAGATGTGATAAGGATCAGAACA  3550
3551  GCAGAGGTTCTTTTAAAGGGGCAGAAAAACTCTGGGAAATAAGAGAGAAC  3600
3601  AACTACTGTGATCAGGCTATGTATGGAATACAGTGTTATTTTCTTTGAAA  3650
3651  TTGTTTAAGTGTTGTAAATATTTATGTAAACTGCATTAGAAATTAGCTGT  3700
3701  GTGAAATACCAGTGTGGTTTGTGTTTGAGTTTATTGAGAATTTTAAATT   3750
3751  ATAACTTAAAATATTTTATAATTTTTAAAGTATATATTTATTTAAGCTTA  3800
```

FIG. 1D

3801 TGTCAGACCTATTTGACATAACACTATAAAGGTTGACAATAAATGTGCTT 3850

3851 ATGTTTAAAAAAA 3863

FIG. 1E

```
  1  CGGGCCTCACTGGCTTCAGGAGCTGAATACCCTCCCAGGCACACACAGGT      50
 51  GGGACACAAATAAGGGTTTTGGAACCACTATTTTCTCATCACGACAGCAA     100
101  CTTAAAATGCCTGGGAAGATGGTCGTGATCCTTGGAGCCTCAAATATACT     150
         MetProGlyLysMetValValIleLeuGlyAlaSerAsnIleLe
151  TTGGATAATGTTTGCAGCTTCTCAAGCTTTTAAAATCGAGACCACCCCAG     200
     uTrpIleMetPheAlaAlaSerGlnAlaPheLysIleGluThrThrProG
201  AATCTAGATATCTTGCTCAGATTGGTGACTCCGTCTCATTGACTTGCAGC     250
     luSerArgTyrLeuAlaGlnIleGlyAspSerValSerLeuThrCysSer
251  ACCACAGGCTGTGAGTCCCCATTTTTCTCTTGGAGAACCCAGATAGATAG     300
     ThrThrGlyCysGluSerProPhePheSerTrpArgThrGlnIleAspSe
301  TCCACTGAATGGGAAGGTGACGAATGAGGGGACCACATCTACGCTGACAA     350
     rProLeuAsnGlyLysValThrAsnGluGlyThrThrSerThrLeuThrM
351  TGAATCCTGTTAGTTTTGGGAACGAACACTCTTACCTGTGCACAGCAACT     400
     etAsnProValSerPheGlyAsnGluHisSerTyrLeuCysThrAlaThr
401  TGTGAATCTAGGAAATTGGAAAAAGGAATCCAGGTGGAGATCTACTCTTT     450
     CysGluSerArgLysLeuGluLysGlyIleGlnValGluIleTyrSerPh
451  TCCTAAGGATCCAGAGATTCATTTGAGTGGCCCTCTGGAGGCTGGGAAGC     500
     eProLysAspProGluIleHisLeuSerGlyProLeuGluAlaGlyLysP
501  CGATCACAGTCAAGTGTTCAGTTGCTGATGTATACCCATTTGACAGGCTG     550
     roIleThrValLysCysSerValAlaAspValTyrProPheAspArgLeu
551  GAGATAGACTTACTGAAAGGAGATCATCTCATGAAGAGTCAGGAATTTCT     600
     GluIleAspLeuLeuLysGlyAspHisLeuMetLysSerGlnGluPheLe
601  GGAGGATGCAGACAGGAAGTCCCTGGAAACCAAGAGTTTGGAAGTAACCT     650
     uGluAspAlaAspArgLysSerLeuGluThrLysSerLeuGluValThrP
651  TTACTCCTGTCATTGAGGATATTGGAAAAGTTCTTGTTTGCCGAGCTAAA     700
     heThrProValIleGluAspIleGlyLysValLeuValCysArgAlaLys
701  TTACACATTGATGAAATGGATTCTGTGCCCACAGTAAGGCAGGCTGTAAA     750
     LeuHisIleAspGluMetAspSerValProThrValArgGlnAlaValLy
751  AGAATTGCAAGTCTACATATCACCCAAGAATACAGTTATTTCTGTGAATC     800
     sGluLeuGlnValTyrIleSerProLysAsnThrValIleSerValAsnP
```

FIG. 2A

```
801  CATCCACAAAGCTGCAAGAAGGTGGCTCTGTGACCATGACCTGTTCCAGC   850
     roSerThrLysLeuGlnGluGlyGlySerValThrMetThrCysSerSer

851  GAGGGTCTACCAGCTCCAGAGATTTTCTGGAGTAAGAAATTAGATAATGG   900
     GluGlyLeuProAlaProGluIlePheTrpSerLysLysLeuAspAsnGl

901  GAATCTACAGCACCTTTCTGGAAATGCAACTCTCACCTTAATTGCTATGA   950
     yAsnLeuGlnHisLeuSerGlyAsnAlaThrLeuThrLeuIleAlaMetA

951  GGATGGAAGATTCTGGAATTTATGTGTGTGAAGGAGTTAATTTGATTGGG   1000
     rgMetGluAspSerGlyIleTyrValCysGluGlyValAsnLeuIleGly

1001 AAAAACAGAAAAGAGGTGGAATTAATTGTTCAAGCATTCCCTAGAGATCC   1050
     LysAsnArgLysGluValGluLeuIleValGlnAlaPheProArgAspPr

1051 AGAAATCGAGATGAGTGGTGGCCTCGTGAATGGGAGCTCTGTCACTGTAA   1100
     oGluIleGluMetSerGlyGlyLeuValAsnGlySerSerValThrValS

1101 GCTGCAAGGTTCCTAGCGTGTACCCCCTTGACCGGCTGGAGATTGAATTA   1150
     erCysLysValProSerValTyrProLeuAspArgLeuGluIleGluLeu

1151 CTTAAGGGGGAGACTATTCTGGAGAATATAGAGTTTTTGGAGGATACGGA   1200
     LeuLysGlyGluThrIleLeuGluAsnIleGluPheLeuGluAspThrAs

1201 TATGAAATCTCTAGAGAACAAAAGTTTGGAAATGACCTTCATCCCTACCA   1250
     pMetLysSerLeuGluAsnLysSerLeuGluMetThrPheIleProThrI

1251 TTGAAGATACTGGAAAAGCTCTTGTTTGTCAGGCTAAGTTACATATTGAT   1300
     leGluAspThrGlyLysAlaLeuValCysGlnAlaLysLeuHisIleAsp

1301 GACATGGAATTCGAACCCAAACAAAGGCAGAGTACGCAAACACTTTATGT   1350
     AspMetGluPheGluProLysGlnArgGlnSerThrGlnThrLeuTyrVa

1351 CAATGTTGCCCCCAGAGATACAACCGTCTTGGTCAGCCCTTCCTCCATCC   1400
     lAsnValAlaProArgAspThrThrValLeuValSerProSerSerIleL

1401 TGGAGGAAGGCAGTTCTGTGAATATGACATGCTTGAGCCAGGGCTTTCCT   1450
     euGluGluGlySerSerValAsnMetThrCysLeuSerGlnGlyPhePro

1451 GCTCCGAAAATCCTGTGGAGCAGGCAGCTCCCTAACGGGGAGCTACAGCC   1500
     AlaProLysIleLeuTrpSerArgGlnLeuProAsnGlyGluLeuGlnPr

1501 TCTTTCTGAGAATGCAACTCTCACCTTAATTTCTACAAAAATGGAAGATT   1550
     oLeuSerGluAsnAlaThrLeuThrLeuIleSerThrLysMetGluAspS

1551 CTGGGGTTTATTTATGTGAAGGAATTAACCAGGCTGGAAGAAGCAGAAAG   1600
     erGlyValTyrLeuCysGluGlyIleAsnGlnAlaGlyArgSerArgLys
```

FIG. 2B

```
1601  GAAGTGGAATTAATTATCCAAGTTACTCCAAAAGACATAAAACTTACAGC     1650
      GluValGluLeuIleIleGlnValThrProLysAspIleLysLeuThrAl

1651  TTTTCCTTCTGAGAGTGTCAAAGAAGGAGACACTGTCATCATCTCTTGTA     1700
      aPheProSerGluSerValLysGluGlyAspThrValIleIleSerCysT

1701  CATGTGGAAATGTTCCAGAAACATGGATAATCCTGAAGAAAAAGCGGAG      1750
      hrCysGlyAsnValProGluThrTrpIleIleLeuLysLysLysAlaGlu

1751  ACAGGAGACACAGTACTAAAATCTATAGATGGCGCCTATACCATCCGAAA     1800
      ThrGlyAspThrValLeuLysSerIleAspGlyAlaTyrThrIleArgLy

1801  GGCCCAGTTGAAGGATGCGGGAGTATATGAATGTGAATCTAAAAACAAAG     1850
      sAlaGlnLeuLysAspAlaGlyValTyrGluCysGluSerLysAsnLysV

1851  TTGGCTCACAATTAAGAAGTTTAACACTTGATGTTCAAGGAAGAGAAAAC     1900
      alGlySerGlnLeuArgSerLeuThrLeuAspValGlnGlyArgGluAsn

1901  AACAAAGACTATTTTCTCCTGAGCTTCTCGTGCTCTATTTTGCATCCTC      1950
      AsnLysAspTyrPheSerProGluLeuLeuValLeuTyrPheAlaSerSe

1951  CTTAATAATACCTGCCATTGGAATGATAATTTACTTTGCAAGAAAAGCCA     2000
      rLeuIleIleProAlaIleGlyMetIleIleTyrPheAlaArgLysAlaA

2001  ACATGAAGGGGTCATATAGTCTTGTAGAAGCACAGAAATCAAAAGTGTAG     2050
      snMetLysGlySerTyrSerLeuValGluAlaGlnLysSerLysVal

2051  CTAATGCTTGATATGTTCAACTGGAGACACTATTTATCTGTGCAAATCCT     2100
2101  TGATACTGCTCATCATTCCTTGAGAAAAACAATGAGCTGAGAGGCAGACT     2150
2151  TCCCTGAATGTATTGAACTTGGAAAGAAATGCCCATCTATGTCCCTTGCT     2200
2201  GTGAGCAAGAAGTCAAAGTAAAACTTGCTGCCTGAAGAACAGTAACTGCC     2250
2251  ATCAAGATGAGAGAACTGGAGGAGTTCCTTGATCTGTATATACAATAACA     2300
2301  TAATTTGTACATATGTAAAATAAAATTATGCCATAGCAAGATTGCTTAAA     2350
2351  ATAGCAACACTCTATATTTAGATTGTTAAAATAACTAGTGTTGCTTGGAC     2400
2401  TATTATAATTTAATGCATGTTAGGAAAATTTCACATTAATATTTGCTGAC     2450
2451  AGCTGACCTTTGTCATCTTTCTTCTATTTTATTCCCTTTCACAAAATTTT     2500
2501  ATTCCTATATAGTTTATTGACAATAATTTCAGGTTTTGTAAAGATGCCGG     2550
```

FIG. 2C

```
2551  GTTTTATATTTTTATAGACAAATAATAAGCAAAGGGAGCACTGGGTTGAC  2600
2601  TTTCAGGTACTAAATACCTCAACCTATGGTATAATGGTTGACTGGGTTTC  2650
2651  TCTGTATAGTACTGGCATGGTACGGAGATGTTTCACGAAGTTTGTTCATC  2700
2701  AGACTCCTGTGCAACTTTCCCAATGTGGCCTAAAAATGCAACTTCTTTTT  2750
2751  ATTTTCTTTTGTAAATGTTTAGGTTTTTTGTATAGTAAAGTGATAATTT   2800
2801  CTGGAATTAAA  2811
```

FIG. 2D

```
  1  CACTGGCTTCAGGAGCTGAATACCCTCCCAGGCACACACAGGTGGGACAC    50

51  AAATAAGGGTTTTGGAACCACTATTTTCTCATCACGACAGCAACTTAAAA   100
                                                      M
101  TGCCTGGGAAGATGGTCGTGATCCTTGGAGCCTCAAATATACTTTGGATA   150
     etProGlyLysMetValValIleLeuGlyAlaSerAsnIleLeuTrpIle
151  ATGTTTGCAGCTTCTCAAGCTTTTAAAATCGAGACCACCCCAGAATCTAG   200
     MetPheAlaAlaSerGlnAlaPheLysIleGluThrThrProGluSerAr
201  ATATCTTGCTCAGATTGGTGACTCCGTCTCATTGACTTGCAGCACCACAG   250
     gTyrLeuAlaGlnIleGlyAspSerValSerLeuThrCysSerThrThrG
251  GCTGTGAGTCCCCATTTTTCTCTTGGAGAACCCAGATAGATAGTCCACTG   300
     lyCysGluSerProPhePheSerTrpArgThrGlnIleAspSerProLeu
301  AATGGGAAGGTGACGAATGAGGGGACCACATCTACGCTGACAATGAATCC   350
     AsnGlyLysValThrAsnGluGlyThrThrSerThrLeuThrMetAsnPr
351  TGTTAGTTTTGGGAACGAACACTCTTACCTGTGCACAGCAACTTGTGAAT   400
     oValSerPheGlyAsnGluHisSerTyrLeuCysThrAlaThrCysGluS
401  CTAGGAAATTGGAAAAAGGAATCCAGGTGGAGATCTACTCTTTTCCTAAG   450
     erArgLysLeuGluLysGlyIleGlnValGluIleTyrSerPheProLys
451  GATCCAGAGATTCATTTGAGTGGCCCTCTGGAGGCTGGGAAGCCGATCAC   500
     AspProGluIleHisLeuSerGlyProLeuGluAlaGlyLysProIleTh
501  AGTCAAGTGTTCAGTTGCTGATGTATACCCATTTGACAGGCTGGAGATAG   550
     rValLysCysSerValAlaAspValTyrProPheAspArgLeuGluIleA
551  ACTTACTGAAAGGAGATCATCTCATGAAGAGTCAGGAATTTCTGGAGGAT   600
     spLeuLeuLysGlyAspHisLeuMetLysSerGlnGluPheLeuGluAsp
601  GCAGACAGGAAGTCCCTGGAAACCAAGAGTTTGGAAGTAACCTTTACTCC   650
     AlaAspArgLysSerLeuGluThrLysSerLeuGluValThrPheThrPr
651  TGTCATTGAGGATATTGGAAAAGTTCTTGTTTGCCGAGCTAAATTACACA   700
     oValIleGluAspIleGlyLysValLeuValCysArgAlaLysLeuHisI
701  TTGATGAAATGGATTCTGTGCCCACAGTAAGGCAGGCTGTAAAAGAATTG   750
     leAspGluMetAspSerValProThrValArgGlnAlaValLysGluLeu
```

FIG. 3A

```
751  CAAGTCTACATATCACCCAAGAATACAGTTATTTCTGTGAATCCATCCAC  800
     GlnValTyrIleSerProLysAsnThrValIleSerValAsnProSerTh

801  AAAGCTGCAAGAAGGTGGCTCTGTGACCATGACCTGTTCCAGCGAGGGTC  850
     rLysLeuGlnGluGlyGlySerValThrMetThrCysSerSerGluGlyL

851  TACCAGCTCCAGAGATTTTCTGGAGTAAGAAATTAGATAATGGGAATCTA  900
     euProAlaProGluIlePheTrpSerLysLysLeuAspAsnGlyAsnLeu

901  CAGCACCTTTCTGGAAATGCAACTCTCACCTTAATTGCTATGAGGATGGA  950
     GlnHisLeuSerGlyAsnAlaThrLeuThrLeuIleAlaMetArgMetGl

951  AGATTCTGGAATTTATGTGTGTGAAGGAGTTAATTTGATTGGGAAAAACA  1000
     uAspSerGlyIleTyrValCysGluGlyValAsnLeuIleGlyLysAsnA

1001 GAAAAGAGGTGGAATTAATTGTTCAAGAGAAACCATTTACTGTTGAGATC  1050
     rgLysGluValGluLeuIleValGlnGluLysProPheThrValGluIle

1051 TCCCCTGGACCCCGGATTGCTGCTCAGATTGGAGACTCAGTCATGTTGAC  1100
     SerProGlyProArgIleAlaAlaGlnIleGlyAspSerValMetLeuTh

1101 ATGTAGTGTCATGGGCTGTGAATCCCCATCTTTCTCCTGGAGAACCCAGA  1150
     rCysSerValMetGlyCysGluSerProSerPheSerTrpArgThrGlnI

1151 TAGACAGCCCTCTGAGCGGGAAGGTGAGGAGTGAGGGGACCAATTCCACG  1200
     leAspSerProLeuSerGlyLysValArgSerGluGlyThrAsnSerThr

1201 CTGACCCTGAGCCCTGTGAGTTTTGAGAACGAACACTCTTATCTGTGCAC  1250
     LeuThrLeuSerProValSerPheGluAsnGluHisSerTyrLeuCysTh

1251 AGTGACTTGTGGACATAAGAAACTGGAAAAGGGAATCCAGGTGGAGCTCT  1300
     rValThrCysGlyHisLysLysLeuGluLysGlyIleGlnValGluLeuT

1301 ACTCATTCCCTAGAGATCCAGAAATCGAGATGAGTGGTGGCCTCGTGAAT  1350
     yrSerPheProArgAspProGluIleGluMetSerGlyGlyLeuValAsn

1351 GGGAGCTCTGTCACTGTAAGCTGCAAGGTTCCTAGCGTGTACCCCCTTGA  1400
     GlySerSerValThrValSerCysLysValProSerValTyrProLeuAs

1401 CCGGCTGGAGATTGAATTACTTAAGGGGGAGACTATTCTGGAGAATATAG  1450
     pArgLeuGluIleGluLeuLeuLysGlyGluThrIleLeuGluAsnIleG

1451 AGTTTTGGAGGATACGGATATGAAATCTCTAGAGAACAAAAGTTTGGAA  1500
     luPheLeuGluAspThrAspMetLysSerLeuGluAsnLysSerLeuGlu

1501 ATGACCTTCATCCCTACCATTGAAGATACTGGAAAAGCTCTTGTTTGTCA  1550
     MetThrPheIleProThrIleGluAspThrGlyLysAlaLeuValCysGl
```

FIG. 3B

```
1551  GGCTAAGTTACATATTGATGACATGGAATTCGAACCCAAACAAAGGCAGA  1600
      nAlaLysLeuHisIleAspAspMetGluPheGluProLysGlnArgGlnS

1601  GTACGCAAACACTTTATGTCAATGTTGCCCCCAGAGATACAACCGTCTTG  1650
      erThrGlnThrLeuTyrValAsnValAlaProArgAspThrThrValLeu

1651  GTCAGCCCTTCCTCCATCCTGGAGGAAGGCAGTTCTGTGAATATGACATG  1700
      ValSerProSerSerIleLeuGluGluGlySerSerValAsnMetThrCy

1701  CTTGAGCCAGGGCTTTCCTGCTCCGAAAATCCTGTGGAGCAGGCAGCTCC  1750
      sLeuSerGlnGlyPheProAlaProLysIleLeuTrpSerArgGlnLeuP

1751  CTAACGGGGAGCTACAGCCTCTTTCTGAGAATGCAACTCTCACCTTAATT  1800
      roAsnGlyGluLeuGlnProLeuSerGluAsnAlaThrLeuThrLeuIle

1801  TCTACAAAAATGGAAGATTCTGGGGTTTATTTATGTGAAGGAATTAACCA  1850
      SerThrLysMetGluAspSerGlyValTyrLeuCysGluGlyIleAsnGl

1851  GGCTGGAAGAAGCAGAAAGGAAGTGGAATTAATTATCCAAGTTACTCCAA  1900
      nAlaGlyArgSerArgLysGluValGluLeuIleIleGlnValThrProL

1901  AAGACATAAAACTTACAGCTTTTCCTTCTGAGAGTGTCAAAGAAGGAGAC  1950
      ysAspIleLysLeuThrAlaPheProSerGluSerValLysGluGlyAsp

1951  ACTGTCATCATCTCTTGTACATGTGGAAATGTTCCAGAAACATGGATAAT  2000
      ThrValIleIleSerCysThrCysGlyAsnValProGluThrTrpIleIl

2001  CCTGAAGAAAAAGCGGAGACAGGAGACACAGTACTAAAATCTATAGATG  2050
      eLeuLysLysLysAlaGluThrGlyAspThrValLeuLysSerIleAspG

2051  GCGCCTATACCATCCGAAAGGCCCAGTTGAAGGATGCGGGAGTATATGAA  2100
      lyAlaTyrThrIleArgLysAlaGlnLeuLysAspAlaGlyValTyrGlu

2101  TGTGAATCTAAAAACAAAGTTGGCTCACAATTAAGAAGTTTAACACTTGA  2150
      CysGluSerLysAsnLysValGlySerGlnLeuArgSerLeuThrLeuAs

2151  TGTTCAAGGAAGAGAAAACAACAAAGACTATTTTCTCCTGAGCTTCTCG  2200
      pValGlnGlyArgGluAsnAsnLysAspTyrPheSerProGluLeuLeuV

2201  TGCTCTATTTTGCATCCTCCTTAATAATACCTGCCATTGGAATGATAATT  2250
      alLeuTyrPheAlaSerSerLeuIleIleProAlaIleGlyMetIleIle

2251  TACTTTGCAAGAAAAGCCAACATGAAGGGGTCATATAGTCTTGTAGAAGC  2300
      TyrPheAlaArgLysAlaAsnMetLysGlySerTyrSerLeuValGluAl

2301  ACAGAAATCAAAAGTGTAGCTAATGCTTGATATGTTCAACTGGAGACACT  2350
      aGlnLysSerLysVal
```

FIG. 3C

```
2351  ATTTATCTGTGCAAATCCTTGATACTGCTCATCATTCCTTGAGAAAAACA  2400
2401  ATGAGCTGAGAGGCAGACTTCCCTGAATGTATTGAACTTGGAAAGAAATG  2450
2451  CCCATCTATGTCCCTTGCTGTGAGCAAGAAGTCAAAGTAAAACTTGCTGC  2500
2501  CTGAAGAACAGTAACTGCCATCAAGATGAGAGAACTGGAGGAGTTCCTTG  2550
2551  ATCTGTATATACAATAACATAATTTGTACATATGTAAAATAAAATTATGC  2600
2601  CATAGCAAGATTGCTTAAAATAGCAACACTCTATATTTAGATTGTTAAAA  2650
2651  TAACTAGTGTTGCTTGGACTATTATAATTTAATGCATGTTAGGAAAATTT  2700
2701  CACATTAATATTTGCTGACAGCTGACCTTGTCATCTTTCTTCTATTTTA   2750
2751  TTCCCTTTCACAAAATTTTATTCCTATATAGTTTATTGACAATAATTTCA  2800
2801  GGTTTTGTAAAGATGCCGGGTTTTATATTTTTATAGACAAATAATAAGCA  2850
2851  AAGGGAGCACTGGGTTGACTTTCAGGTACTAAATACCTCAACCTATGGTA  2900
2901  TAATGGTTGACTGGGTTTCTCTGTATAGTACTGGCATGGTACGGAGATGT  2950
2951  TTCACGAAGTTTGTTCATCAGACTCCTGTGCAACTTTCCCAATGTGGCCT  3000
3001  AAAAATGCAACTTCTTTTTATTTTCTTTTGTAAATGTTTAGGTTTTTTG   3050
3051  TATAGTAAAGTGATAATTTCTGGAATTAAA  3080
```

FIG. 3D

```
                                    *                                              *
            G   h f C           P       Wp                  P       DsG   o C    N
1                       FKIETTPESRYLAQIGDSVSLTCSTTGCESPFFSVRTQIDSPLNGK----------VTNEGTTSTLTMNPVSFGNEHSYLCTATCESRKLEKGI
2   QVEIYSFPKDPEIHLSGPL-EAGKPITVKCSVA-DVYPFDRLEIDLLKGDHLMKSQEFLEDADRKSLETKSLEVTFTPVIEDIGKVLVCRAKLHIDEMDSVPTVRQAVKEL
3   QVYISPKNTVISVNPSTKL-QEGGSVTMTCSSEGLPAPEIFVSKKLDNGNLQH----------LSGNATLTL-IAMRMEDSG-IYVCEGVNLIGKNRKEVELIVQA
4       FPRDPEIEMSGGL-VNGSSVTVSCKVP-SVYPLDRLEIELLKGETILENIEFLEDTDMKSLENKSLEMTFIPTIEDTGKALVCQAKLHIDDMEFEPKQRQSTQTL
5   YVNVAPRDTTVLVSPSSIL-EEGSSVNMTCLSQGFPAPKILVSRQLPNGELQP----------LSENATLTL-ISTKMEDSG-VYLCEGINQAGRSRKEVELIIQV
6   TPKDIKLTAFPSESV-KEGDTVIISCTCGNV--PET-VIILKKAETGDTVL----------SIDGAYTIRKAQLKDAG-VYECESKNKVGSQLRSLTLDVQGREN

NKDYFSPELLVLYFASSLIIPAIGMIIYFARKANMKGSYSLVEAQKSKV
```

FIG. 4

```
                *                                                                          *
         G    h f C       P     Wp                                            P   DsG   o C      N

1              FKIETTPESRYLAQIGDSVSLTCSTTGCESPFFSWRTQIDSPLNGK---------------VTNEGTTSTLTMNPVSFGNEHSYLCTATCESRKLEKGI
2    QVEIYSFPKDPEIHLSGPL-EAGKPITVKCSVA-DVYPFDRLEIDLLKGDHLMKSQEFLEDADRKSLETKSLEVTFTPVIEDIGKVLVCRAKLHIDEMDSVPTVRQAVKEL
3    QVYISPKNTVISVNPSTKL-QEGGSVTMTCSSEGLPAPEIFWSKKLDNGNLQH---------------LSGNATLTL-IAMRMEDSG-IYVCEGVNLIGKNRKEVELIVQEKP
3B             FTVEISPGPRIAAQIGDSVMLTCSVMGCESPSFSWRTQIDSPLSGK---------------VRSEGTNSTLTLSPVSFENEHSYLCTVTCGHKKLEKGI
4    QVELYSFPRDPEIEMSGGL-VNGSSVTVSCKVP-SVYPLDRLEIELLKGETILENIEFLEDTDMKSLEMTFIPTIEDTGKALVCQAKLHIDDMEFEPKQRQSTQTL
5    YVNVAPRDTTVLVSPSSIL-EEGSSVNMTCLSQGFPAPKILWSRQLPNGELQP---------------LSENATLTL-ISTKMEDSG-VYLCEGINQAGRSRKEVELIIQV
6    TPKDIKLTAFPSESV-KEGDTVIISCTCGNV--PET-VIILKKKAETGDTVL---------------SIDGAYTIRKAQLKDAG-VYECESKNKVGSQLRSLTLDVQGREN

NKDYFSPELLVLYFASSLIIPAIGMIIYFARKANMKGSYSLVEAQKSKV
```

FIG. 5

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
        (A) LENGTH: 3863 base pairs
        (B) TYPE: nucleic acid
        (C) STRANDEDNESS: double
        (D) TOPOLOGY: linear (xi) SEQUENCE DESCRIPTION: SEQ ID NO:1:

```
TTCACATCAA AACTCCTATA CTGACCTGAG ACAGAGGCAG CAGTGATACC CACCTGAGAG       60

ATCCTGTGTT TGAACAACTG CTTCCCAAAA CGGAAAGTAT TTCAAGCCTA AACCTTTGGG      120

TGAAAAGAAC TCTTGAAGTC ATGATTGCTT CACAGTTTCT CTCAGCTCTC ACTTTGGTGC      180

TTCTCATTAA AGAGAGTGGA GCCTGGTCTT ACAACACCTC CACGGAAGCT ATGACTTATG      240

ATGAGGCCAG TGCTTATTGT CAGCAAAGGT ACACACACCT GGTTGCAATT CAAAACAAAG      300

AAGAGATTGA GTACCTAAAC TCCATATTGA GCTATTCACC AAGTTATTAC TGGATTGGAA      360

TCAGAAAAGT CAACAATGTG TGGGTCTGGG TAGGAACCCA GAAACCTCTG ACAGAAGAAG      420

CCAAGAACTG GGCTCCAGGT GAACCCAACA ATAGGCAAAA AGATGAGGAC TGCGTGGAGA      480

TCTACATCAA GAGAGAAAAA GATGTGGGCA TGTGGAATGA TGAGAGGTGC AGCAAGAAGA      540

AGCTTGCCCT ATGCTACACA GCTGCCTGTA CCAATACATC CTGCAGTGGC CACGGTGAAT      600

GTGTAGAGAC CATCAATAAT TACACTTGCA AGTGTGACCC TGGCTTCAGT GGACTCAAGT      660

GTGAGCAAAT TGTGAACTGT ACAGCCCTGG AATCCCCTGA GCATGGAAGC CTGGTTTGCA      720

GTCACCCACT GGGAAACTTC AGCTACAATT CTTCCTGCTC TATCAGCTGT GATAGGGGTT      780

ACCTGCCAAG CAGCATGGAG ACCATGCAGT GTATGTCCTC TGGAGAATGG AGTGCTCCTA      840

TTCCAGCCTG CAATGTGGTT GAGTGTGATG CTGTGACAAA TCCAGCCAAT GGGTTCGTGG      900

AATGTTTCCA AAACCCTGGA AGCTTCCCAT GGAACACAAC CTGTACATTT GACTGTGAAG      960

AAGGATTTGA ACTAATGGGA GCCCAGAGCC TTCAGTGTAC CTCATCTGGG AATTGGGACA     1020

ACGAGAAGCC AACGTGTAAA GCTGTGACAT GCAGGGCCGT CCGCCAGCCT CAGAATGGCT     1080

CTGTGAGGTG CAGCCATTCC CCTGCTGGAG AGTTCACCTT CAAATCATCC TGCAACTTCA     1140

CCTGTGAGGA AGGCTTCATG TTGCAGGGAC CAGCCCAGGT TGAATGCACC ACTCAAGGGC     1200
```

```
AGTGGACACA GCAAATCCCA GTTTGTGAAG CTTTCCAGTG CACAGCCTTG TCCAACCCCG    1260

AGCGAGGCTA CATGAATTGT CTTCCTAGTG CTTCTGGCAG TTTCCGTTAT GGGTCCAGCT    1320

GTGAGTTCTC CTGTGAGCAG GGTTTTGTGT TGAAGGGATC CAAAAGGCTC AATGTGGCC     1380

CCACAGGGGA GTGGGACAAC GAGAAGCCCA CATGTGAAGC TGTGAGATGC GATGCTGTCC    1440

ACCAGCCCCC GAAGGGTTTG GTGAGGTGTG CTCATTCCCC TATTGGAGAA TTCACCTACA    1500

AGTCCTCTTG TGCCTTCAGC TGTGAGGAGG GATTTGAATT ACATGGATCA ACTCAACTTG    1560

AGTGCACATC TCAGGGACAA TGGACAGAAG AGGTTCCTTC CTGCCAAGTG GTAAAATGTT    1620

CAAGCCTGGC AGTTCCGGGA AGATCAACA TGAGCTGCAG TGGGGAGCCC GTGTTTGGCA     1680

CTGTGTGCAA GTTCGCCTGT CCTGAAGGAT GGACGCTCAA TGGCTCTGCA GCTCGGACAT    1740

GTGGAGCCAC AGGACACTGG TCTGGCCTGC TACCTACCTG TGAAGCTCCC ACTGAGTCCA    1800

ACATTCCCTT GGTAGCTGGA CTTTCTGCTG CTGGACTCTC CCTCCTGACA TTAGCACCAT    1860

TTCTCCTCTG GCTTCGGAAA TGCTTACGGA AGCAAAGAA ATTTGTTCCT GCCAGCAGCT     1920

GCCAAAGCCT TGAATCAGAT GGAAGCTACC AAAAGCCTTC TTACATCCTT TAAGTTCAAA    1980

AGAATCAGAA ACAGGTGCAT CTGGGGAACT AGAGGGATAC ACTGAAGTTA ACAGAGACAG    2040

ATAACTCTCC TCGGGTCTCT GGCCCTTCTT GCCTACTATG CCAGATGCCT TTATGGCTGA    2100

AACCGCAACA CCCATCACCA CTTCAATAGA TCAAAGTCCA GCAGGCAAGG ACGGCCTTCA    2160

ACTGAAAAGA CTCAGTGTTC CCTTTCCTAC TCTCAGGATC AAGAAAGTGT TGGCTAATGA    2220

AGGGAAAGGA TATTTTCTTC CAAGCAAAGG TGAAGAGACC AAGACTCTGA ATCTCAGAA     2280

TTCCTTTTCT AACTCTCCCT TGCTCGCTGT AAAATCTTGG CACAGAAACA CAATATTTTG    2340

TGGCTTTCTT TCTTTTGCCC TTCACAGTGT TTCGACAGCT GATTACACAG TTGCTGTCAT    2400

AAGAATGAAT AATAATTATC CAGAGTTTAG AGGAAAAAAA TGACTAAAAA TATTATAACT    2460

TAAAAAATGA CAGATGTTGA ATGCCCACAG GCAAATGCAT GGAGGGTTGT TAATGGTGCA    2520

AATCCTACTG AATGCTCTGT GCGAGGGTTA CTATGCACAA TTTAATCACT TTCATCCCTA    2580

TGGGATTCAG TGCTTCTTAA AGAGTTCTTA AGGATTGTGA TATTTTTACT TGCATTGAAT    2640

ATATTATAAT CTTCCATACT TCTTCATTCA ATACAAGTGT GGTAGGGACT TAAAAAACTT    2700

GTAAATGCTG TCAACTATGA TATGGTAAAA GTTACTTATT CTAGATTACC CCCTCATTGT    2760

TTATTAACAA ATTATGTTAC ATCTGTTTTA AATTTATTTC AAAAAGGGAA ACTATTGTCC    2820

CCTAGCAAGG CATGATGTTA ACCAGAATAA AGTTCTGAGT GTTTTTACTA CAGTTGTTTT    2880

TTGAAAACAT GGTAGAATTG GAGAGTAAAA ACTGAATGGA AGGTTTGTAT ATTGTCAGAT    2940

ATTTTTTCAG AAATATGTGG TTTCCACGAT GAAAAACTTC CATGAGGCCA AACGTTTTGA    3000

ACTAATAAAA GCATAAATGC AAACACACAA AGGTATAATT TTATGAATGT CTTTGTTGGA    3060

AAAGAATACA GAAAGATGGA TGTGCTTTGC ATTCCTACAA AGATGTTTGT CAGATATGAT    3120

ATGTAAACAT AATTCTTGTA TATTATGGAA GATTTTAAAT TCACAATAGA AACTCACCAT    3180

GTAAAAGAGT CATCTGGTAG ATTTTTAACG AATGAAGATG TCTAATAGTT ATTCCCTATT    3240

TGTTTTCTTC TGTATGTTAG GGTGCTCTGG AAGAGAGGAA TGCCTGTGTG AGCAAGCATT    3300

TATGTTTATT TATAAGCAGA TTTAACAATT CCAAAGGAAT CTCCAGTTTT CAGTTGATCA    3360

CTGGCAATGA AAAATTCTCA GTCAGTAATT GCCAAAGCTG CTCTAGCCTT GAGGAGTGTG    3420

AGAATCAAAA CTCTCCTACA CTTCCATTAA CTTAGCATGT GTTGAAAAAA AGTTTCAGA     3480

GAAGTTCTGG CTGAACACTG GCAACAACAA AGCCAACAGT CAAAACAGAG ATGTGATAAG    3540

GATCAGAACA GCAGAGGTTC TTTTAAAGGG GCAGAAAAAC TCTGGGAAAT AAGAGAGAAC    3600
```

```
AACTACTGTG ATCAGGCTAT GTATGGAATA CAGTGTTATT TTCTTTGAAA TTGTTTAAGT      3660

GTTGTAAATA TTTATGTAAA CTGCATTAGA AATTAGCTGT GTGAAATACC AGTGTGGTTT      3720

GTGTTTGAGT TTTATTGAGA ATTTTAAATT ATAACTTAAA ATATTTTATA ATTTTTAAAG      3780

TATATATTTA TTTAAGCTTA TGTCAGACCT ATTTGACATA ACACTATAAA GGTTGACAAT      3840

AAATGTGCTT ATGTTTAAAA AAA                                             3863

(2) INFORMATION FOR SEQ ID NO:2:

(i) SEQUENCE CHARACTERISTICS:
        (A) LENGTH: 110 base pairs
        (B) TYPE: nucleic acid
        (C) STRANDEDNESS: double
        (D) TOPOLOGY: linear (xi) SEQUENCE DESCRIPTION: SEQ ID NO:2:

GCTAGCGGCC TCCGCGGCCA GTCCAACCAC CAATCTCAAA GCATAGGCGA CATGCGGCCG        60

CAAAACGATC AGCAGATCCT CACATCCCAA TCCGAGGCCG CGGTGGCCGC                  110

(2) INFORMATION FOR SEQ ID NO:3:

(i) SEQUENCE CHARACTERISTICS:
        (A) LENGTH: 2811 base pairs
        (B) TYPE: nucleic acid
        (C) STRANDEDNESS: double
        (D) TOPOLOGY: linear (xi) SEQUENCE DESCRIPTION: SEQ ID NO:3:

CGGGCCTCAC TGGCTTCAGG AGCTGAATAC CCTCCCAGGC ACACACAGGT GGGACACAAA        60

TAAGGGTTTT GGAACCACTA TTTTCTCATC ACGACAGCAA CTTAAAATGC CTGGGAAGAT       120

GGTCGTGATC CTTGGAGCCT CAAATATACT TTGGATAATG TTTGCAGCTT CTCAAGCTTT       180

TAAAATCGAG ACCACCCCAG AATCTAGATA TCTTGCTCAG ATTGGTGACT CCGTCTCATT       240

GACTTGCAGC ACCACAGGCT GTGAGTCCCC ATTTTTCTCT TGGAGAACCC AGATAGATAG       300

TCCACTGAAT GGGAAGGTGA CGAATGAGGG GACCACATCT ACGCTGACAA TGAATCCTGT       360

TAGTTTTGGG AACGAACACT CTTACCTGTG CACAGCAACT TGTGAATCTA GGAAATTGGA       420

AAAAGGAATC CAGGTGGAGA TCTACTCTTT TCCTAAGGAT CCAGAGATTC ATTTGAGTGG       480

CCCTCTGGAG GCTGGGAAGC CGATCACAGT CAAGTGTTCA GTTGCTGATG TATACCCATT       540

TGACAGGCTG GAGATAGACT TACTGAAAGG AGATCATCTC ATGAAGAGTC AGGAATTTCT       600

GGAGGATGCA GACAGGAAGT CCCTGGAAAC CAAGAGTTTG GAAGTAACCT TTACTCCTGT       660

CATTGAGGAT ATTGGAAAAG TTCTTGTTTG CCGAGCTAAA TTACACATTG ATGAAATGGA       720

TTCTGTGCCC ACAGTAAGGC AGGCTGTAAA AGAATTGCAA GTCTACATAT CACCCAAGAA       780

TACAGTTATT TCTGTGAATC CATCCACAAA GCTGCAAGAA GGTGGCTCTG TGACCATGAC       840

CTGTTCCAGC GAGGGTCTAC CAGCTCCAGA GATTTTCTGG AGTAAGAAAT TAGATAATGG       900

GAATCTACAG CACCTTTCTG GAAATGCAAC TCTCACCTTA ATTGCTATGA GGATGGAAGA       960

TTCTGGAATT TATGTGTGTG AAGGAGTTAA TTTGATTGGG AAAAACAGAA AGAGGTGGA      1020

ATTAATTGTT CAAGCATTCC CTAGAGATCC AGAAATCGAG ATGAGTGGTG GCCTCGTGAA      1080

TGGGAGCTCT GTCACTGTAA GCTGCAAGGT TCCTAGCGTG TACCCCCTTG ACCGGCTGGA      1140

GATTGAATTA CTTAAGGGGG AGACTATTCT GGAGAATATA GAGTTTTTGG AGGATACGGA      1200

TATGAAATCT CTAGAGAACA AAAGTTTGGA AATGACCTTC ATCCCTACCA TTGAAGATAC      1260
```

```
TGGAAAAGCT CTTGTTTGTC AGGCTAAGTT ACATATTGAT GACATGGAAT TCGAACCCAA      1320

ACAAAGGCAG AGTACGCAAA CACTTTATGT CAATGTTGCC CCCAGAGATA CAACCGTCTT      1380

GGTCAGCCCT TCCTCCATCC TGGAGGAAGG CAGTTCTGTG AATATGACAT GCTTGAGCCA      1440

GGGCTTTCCT GCTCCGAAAA TCCTGTGGAG CAGGCAGCTC CCTAACGGGG AGCTACAGCC      1500

TCTTTCTGAG AATGCAACTC TCACCTTAAT TTCTACAAAA ATGGAAGATT CTGGGGTTTA      1560

TTTATGTGAA GGAATTAACC AGGCTGGAAG AAGCAGAAAG GAAGTGGAAT TAATTATCCA      1620

AGTTACTCCA AAAGACATAA AACTTACAGC TTTTCCTTCT GAGAGTGTCA AGAAGGAGA      1680

CACTGTCATC ATCTCTTGTA CATGTGGAAA TGTTCCAGAA ACATGGATAA TCCTGAAGAA      1740

AAAAGCGGAG ACAGGAGACA CAGTACTAAA ATCTATAGAT GGCGCCTATA CCATCCGAAA      1800

GGCCCAGTTG AAGGATGCGG GAGTATATGA ATGTGAATCT AAAAACAAAG TTGGCTCACA      1860

ATTAAGAAGT TTAACACTTG ATGTTCAAGG AAGAGAAAAC AACAAAGACT ATTTTTCTCC      1920

TGAGCTTCTC GTGCTCTATT TTGCATCCTC CTTAATAATA CCTGCCATTG GAATGATAAT      1980

TTACTTTGCA AGAAAAGCCA ACATGAAGGG GTCATATAGT CTTGTAGAAG CACAGAAATC      2040

AAAAGTGTAG CTAATGCTTG ATATGTTCAA CTGGAGACAC TATTTATCTG TGCAAATCCT      2100

TGATACTGCT CATCATTCCT TGAGAAAAAC AATGAGCTGA GAGGCAGACT TCCCTGAATG      2160

TATTGAACTT GGAAAGAAAT GCCCATCTAT GTCCCTTGCT GTGAGCAAGA AGTCAAAGTA      2220

AAACTTGCTG CCTGAAGAAC AGTAACTGCC ATCAAGATGA GAGAACTGGA GGAGTTCCTT      2280

GATCTGTATA TACAATAACA TAATTTGTAC ATATGTAAAA TAAAATTATG CCATAGCAAG      2340

ATTGCTTAAA ATAGCAACAC TCTATATTTA GATTGTTAAA ATAACTAGTG TTGCTTGGAC      2400

TATTATAATT TAATGCATGT TAGGAAAATT TCACATTAAT ATTTGCTGAC AGCTGACCTT      2460

TGTCATCTTT CTTCTATTTT ATTCCCTTTC ACAAAATTTT ATTCCTATAT AGTTTATTGA      2520

CAATAATTTC AGGTTTTGTA AAGATGCCGG GTTTTATATT TTTATAGACA AATAATAAGC      2580

AAAGGGAGCA CTGGGTTGAC TTTCAGGTAC TAAATACCTC AACCTATGGT ATAATGGTTG      2640

ACTGGGTTTC TCTGTATAGT ACTGGCATGG TACGAGATG TTTCACGAAG TTTGTTCATC      2700

AGACTCCTGT GCAACTTTCC CAATGTGGCC TAAAAATGCA ACTTCTTTTT ATTTTCTTTT      2760

GTAAATGTTT AGGTTTTTTT GTATAGTAAA GTGATAATTT CTGGAATTAA A              2811

(2) INFORMATION FOR SEQ ID NO:4:

(i) SEQUENCE CHARACTERISTICS:
        (A) LENGTH: 3080 base pairs
        (B) TYPE: nucleic acid
        (C) STRANDEDNESS: double
        (D) TOPOLOGY: linear (xi) SEQUENCE DESCRIPTION: SEQ ID NO:4:

CACTGGCTTC AGGAGCTGAA TACCCTCCCA GGCACACACA GGTGGGACAC AAATAAGGGT        60

TTTGGAACCA CTATTTTCTC ATCACGACAG CAACTTAAAA TGCCTGGGAA GATGGTCGTG       120

ATCCTTGGAG CCTCAAATAT ACTTTGGATA ATGTTTGCAG CTTCTCAAGC TTTTAAAATC       180

GAGACCACCC CAGAATCTAG ATATCTTGCT CAGATTGGTG ACTCCGTCTC ATTGACTTGC       240

AGCACCACAG GCTGTGAGTC CCCATTTTTC TCTTGGAGAA CCCAGATAGA TAGTCCACTG       300

AATGGGAAGG TGACGAATGA GGGGACCACA TCTACGCTGA CAATGAATCC TGTTAGTTTT       360

GGGAACGAAC ACTCTTACCT GTGCACAGCA ACTTGTGAAT CTAGGAAATT GGAAAAAGGA       420

ATCCAGGTGG AGATCTACTC TTTTCCTAAG GATCCAGAGA TTCATTTGAG TGGCCCTCTG       480
```

-continued

```
GAGGCTGGGA AGCCGATCAC AGTCAAGTGT TCAGTTGCTG ATGTATACCC ATTTGACAGG      540

CTGGAGATAG ACTTACTGAA AGGAGATCAT CTCATGAAGA GTCAGGAATT TCTGGAGGAT      600

GCAGACAGGA AGTCCCTGGA AACCAAGAGT TTGGAAGTAA CCTTTACTCC TGTCATTGAG      660

GATATTGGAA AAGTTCTTGT TTGCCGAGCT AAATTACACA TTGATGAAAT GGATTCTGTG      720

CCCACAGTAA GGCAGGCTGT AAAAGAATTG CAAGTCTACA TATCACCCAA GAATACAGTT      780

ATTTCTGTGA ATCCATCCAC AAAGCTGCAA GAAGGTGGCT CTGTGACCAT GACCTGTTCC      840

AGCGAGGGTC TACCAGCTCC AGAGATTTTC TGGAGTAAGA AATTAGATAA TGGGAATCTA      900

CAGCACCTTT CTGGAAATGC AACTCTCACC TTAATTGCTA TGAGGATGGA AGATTCTGGA      960

ATTTATGTGT GTGAAGGAGT TAATTTGATT GGGAAAAACA GAAAAGAGGT GGAATTAATT     1020

GTTCAAGAGA AACCATTTAC TGTTGAGATC TCCCCTGGAC CCCGGATTGC TGCTCAGATT     1080

GGAGACTCAG TCATGTTGAC ATGTAGTGTC ATGGGCTGTG AATCCCCATC TTTCTCCTGG     1140

AGAACCCAGA TAGACAGCCC TCTGAGCGGG AAGGTGAGGA GTGAGGGGAC CAATTCCACG     1200

CTGACCCTGA GCCCTGTGAG TTTTGAGAAC GAACACTCTT ATCTGTGCAC AGTGACTTGT     1260

GGACATAAGA AACTGGAAAA GGGAATCCAG GTGGAGCTCT ACTCATTCCC TAGAGATCCA     1320

GAAATCGAGA TGAGTGGTGG CCTCGTGAAT GGGAGCTCTG TCACTGTAAG CTGCAAGGTT     1380

CCTAGCGTGT ACCCCCTTGA CCGGCTGGAG ATTGAATTAC TTAAGGGGGA GACTATTCTG     1440

GAGAATATAG AGTTTTTGGA GGATACGGAT ATGAAATCTC TAGAGAACAA AGTTTGGAA     1500

ATGACCTTCA TCCCTACCAT TGAAGATACT GGAAAAGCTC TTGTTTGTCA GGCTAAGTTA     1560

CATATTGATG ACATGGAATT CGAACCCAAA CAAAGGCAGA GTACGCAAAC ACTTTATGTC     1620

AATGTTGCCC CCAGAGATAC AACCGTCTTG GTCAGCCCTT CCTCCATCCT GGAGGAAGGC     1680

AGTTCTGTGA ATATGACATG CTTGAGCCAG GGCTTTCCTG CTCCGAAAAT CCTGTGGAGC     1740

AGGCAGCTCC CTAACGGGGA GCTACAGCCT CTTTCTGAGA ATGCAACTCT CACCTTAATT     1800

TCTACAAAAA TGGAAGATTC TGGGGTTTAT TTATGTGAAG GAATTAACCA GGCTGGAAGA     1860

AGCAGAAAGG AAGTGGAATT AATTATCCAA GTTACTCCAA AAGACATAAA ACTTACAGCT     1920

TTTCCTTCTG AGAGTGTCAA AGAAGGAGAC ACTGTCATCA TCTCTTGTAC ATGTGGAAAT     1980

GTTCCAGAAA CATGGATAAT CCTGAAGAAA AAGCGGAGA CAGGAGACAC AGTACTAAAA     2040

TCTATAGATG GCGCCTATAC CATCCGAAAG GCCCAGTTGA AGGATGCGGG AGTATATGAA     2100

TGTGAATCTA AAAACAAAGT TGGCTCACAA TTAAGAAGTT TAACACTTGA TGTTCAAGGA     2160

AGAGAAAACA ACAAAGACTA TTTTTCTCCT GAGCTTCTCG TGCTCTATTT TGCATCCTCC     2220

TTAATAATAC CTGCCATTGG AATGATAATT TACTTTGCAA GAAAGCCAA CATGAAGGGG     2280

TCATATAGTC TTGTAGAAGC ACAGAAATCA AAAGTGTAGC TAATGCTTGA TATGTTCAAC     2340

TGGAGACACT ATTTATCTGT GCAAATCCTT GATACTGCTC ATCATTCCTT GAGAAAAACA     2400

ATGAGCTGAG AGGCAGACTT CCCTGAATGT ATTGAACTTG GAAAGAAATG CCCATCTATG     2460

TCCCTTGCTG TGAGCAAGAA GTCAAAGTAA AACTTGCTGC CTGAAGAACA GTAACTGCCA     2520

TCAAGATGAG AGAACTGGAG GAGTTCCTTG ATCTGTATAT ACAATAACAT AATTTGTACA     2580

TATGTAAAAT AAAATTATGC CATAGCAAGA TTGCTTAAAA TAGCAACACT CTATATTTAG     2640

ATTGTTAAAA TAACTAGTGT TGCTTGGACT ATTATAATTT AATGCATGTT AGGAAAATTT     2700

CACATTAATA TTTGCTGACA GCTGACCTTT GTCATCTTTC TTCTATTTTA TTCCCTTTCA     2760

CAAAATTTTA TTCCTATATA GTTTATTGAC AATAATTTCA GGTTTTGTAA AGATGCCGGG     2820

TTTTATATTT TTATAGACAA ATAATAAGCA AAGGGAGCAC TGGGTTGACT TTCAGGTACT     2880
```

```
AAATACCTCA ACCTATGGTA TAATGGTTGA CTGGGTTTCT CTGTATAGTA CTGGCATGGT      2940

ACGGAGATGT TTCACGAAGT TGTTCATCA GACTCCTGTG CAACTTTCCC AATGTGGCCT       3000

AAAAATGCAA CTTCTTTTTA TTTTCTTTTG TAAATGTTTA GGTTTTTTTG TATAGTAAAG      3060

TGATAATTTC TGGAATTAAA                                                   3080
```

(2) INFORMATION FOR SEQ ID NO:5:

(i) SEQUENCE CHARACTERISTICS:
        (A) LENGTH: 647 amino acids
        (B) TYPE: amino acid
        (C) STRANDEDNESS: single
        (D) TOPOLOGY: linear (xi) SEQUENCE DESCRIPTION: SEQ ID NO:5:

```
Met Pro Gly Lys Met Val Val Ile Leu Gly Ala Ser Asn Ile Leu Trp
1               5                  10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Ala Phe Pro Arg Asp Pro Glu Ile Glu Met Ser
305                 310                 315                 320
```

```
Gly Gly Leu Val Asn Gly Ser Ser Val Thr Val Ser Cys Lys Val Pro
                325                 330                 335
Ser Val Tyr Pro Leu Asp Arg Leu Glu Ile Glu Leu Leu Lys Gly Glu
            340                 345                 350
Thr Ile Leu Glu Asn Ile Glu Phe Leu Glu Asp Thr Asp Met Lys Ser
        355                 360                 365
Leu Glu Asn Lys Ser Leu Glu Met Thr Phe Ile Pro Thr Ile Glu Asp
    370                 375                 380
Thr Gly Lys Ala Leu Val Cys Gln Ala Lys Leu His Ile Asp Asp Met
385                 390                 395                 400
Glu Phe Glu Pro Lys Gln Arg Gln Ser Thr Gln Thr Leu Tyr Val Asn
                405                 410                 415
Val Ala Pro Arg Asp Thr Thr Val Leu Val Ser Pro Ser Ser Ile Leu
            420                 425                 430
Glu Glu Gly Ser Ser Val Asn Met Thr Cys Leu Ser Gln Gly Phe Pro
        435                 440                 445
Ala Pro Lys Ile Leu Trp Ser Arg Gln Leu Pro Asn Gly Glu Leu Gln
    450                 455                 460
Pro Leu Ser Glu Asn Ala Thr Leu Thr Leu Ile Ser Thr Lys Met Glu
465                 470                 475                 480
Asp Ser Gly Val Tyr Leu Cys Glu Gly Ile Asn Gln Ala Gly Arg Ser
                485                 490                 495
Arg Lys Glu Val Glu Leu Ile Ile Gln Val Thr Pro Lys Asp Ile Lys
            500                 505                 510
Leu Thr Ala Phe Pro Ser Glu Ser Val Lys Glu Gly Asp Thr Val Ile
        515                 520                 525
Ile Ser Cys Thr Cys Gly Asn Val Pro Glu Thr Trp Ile Ile Leu Lys
        530                 535                 540
Lys Lys Ala Glu Thr Gly Asp Thr Val Leu Lys Ser Ile Asp Gly Ala
545                 550                 555                 560
Tyr Thr Ile Arg Lys Ala Gln Leu Lys Asp Ala Gly Val Tyr Glu Cys
                565                 570                 575
Glu Ser Lys Asn Lys Val Gly Ser Gln Leu Arg Ser Leu Thr Leu Asp
            580                 585                 590
Val Gln Gly Arg Glu Asn Asn Lys Asp Tyr Phe Ser Pro Glu Leu Leu
        595                 600                 605
Val Leu Tyr Phe Ala Ser Ser Leu Ile Ile Pro Ala Ile Gly Met Ile
    610                 615                 620
Ile Tyr Phe Ala Arg Lys Ala Asn Met Lys Gly Ser Tyr Ser Leu Val
625                 630                 635                 640
Glu Ala Gln Lys Ser Lys Val
                645

(2) INFORMATION FOR SEQ ID NO:6:

(i) SEQUENCE CHARACTERISTICS:
        (A) LENGTH: 739 amino acids
        (B) TYPE: amino acid
        (C) STRANDEDNESS: single
        (D) TOPOLOGY: linear (xi) SEQUENCE DESCRIPTION: SEQ ID NO:6:

Met Pro Gly Lys Met Val Val Ile Leu Gly Ala Ser Asn Ile Leu Trp
1               5                   10                  15
Ile Met Phe Ala Ala Ser Gln Ala Phe Lys Ile Glu Thr Thr Pro Glu
```

```
              20                  25                  30
Ser Arg Tyr Leu Ala Gln Ile Gly Asp Ser Val Ser Leu Thr Cys Ser
             35                  40                  45
Thr Thr Gly Cys Glu Ser Pro Phe Phe Ser Trp Arg Thr Gln Ile Asp
 50                  55                  60
Ser Pro Leu Asn Gly Lys Val Thr Asn Glu Gly Thr Thr Ser Thr Leu
 65                  70                  75                  80
Thr Met Asn Pro Val Ser Phe Gly Asn Glu His Ser Tyr Leu Cys Thr
                 85                  90                  95
Ala Thr Cys Glu Ser Arg Lys Leu Glu Lys Gly Ile Gln Val Glu Ile
                100                 105                 110
Tyr Ser Phe Pro Lys Asp Pro Glu Ile His Leu Ser Gly Pro Leu Glu
             115                 120                 125
Ala Gly Lys Pro Ile Thr Val Lys Cys Ser Val Ala Asp Val Tyr Pro
130                 135                 140
Phe Asp Arg Leu Glu Ile Asp Leu Leu Lys Gly Asp His Leu Met Lys
145                 150                 155                 160
Ser Gln Glu Phe Leu Glu Asp Ala Asp Arg Lys Ser Leu Glu Thr Lys
                165                 170                 175
Ser Leu Glu Val Thr Phe Thr Pro Val Ile Glu Asp Ile Gly Lys Val
                180                 185                 190
Leu Val Cys Arg Ala Lys Leu His Ile Asp Glu Met Asp Ser Val Pro
                195                 200                 205
Thr Val Arg Gln Ala Val Lys Glu Leu Gln Val Tyr Ile Ser Pro Lys
         210                 215                 220
Asn Thr Val Ile Ser Val Asn Pro Ser Thr Lys Leu Gln Glu Gly Gly
225                 230                 235                 240
Ser Val Thr Met Thr Cys Ser Ser Glu Gly Leu Pro Ala Pro Glu Ile
                245                 250                 255
Phe Trp Ser Lys Lys Leu Asp Asn Gly Asn Leu Gln His Leu Ser Gly
                260                 265                 270
Asn Ala Thr Leu Thr Leu Ile Ala Met Arg Met Glu Asp Ser Gly Ile
             275                 280                 285
Tyr Val Cys Glu Gly Val Asn Leu Ile Gly Lys Asn Arg Lys Glu Val
         290                 295                 300
Glu Leu Ile Val Gln Glu Lys Pro Phe Thr Val Glu Ile Ser Pro Gly
305                 310                 315                 320
Pro Arg Ile Ala Ala Gln Ile Gly Asp Ser Val Met Leu Thr Cys Ser
                325                 330                 335
Val Met Gly Cys Glu Ser Pro Ser Phe Ser Trp Arg Thr Gln Ile Asp
             340                 345                 350
Ser Pro Leu Ser Gly Lys Val Arg Ser Glu Gly Thr Asn Ser Thr Leu
         355                 360                 365
Thr Leu Ser Pro Val Ser Phe Glu Asn Glu His Ser Tyr Leu Cys Thr
 370                 375                 380
Val Thr Cys Gly His Lys Lys Leu Glu Lys Gly Ile Gln Val Glu Leu
385                 390                 395                 400
Tyr Ser Phe Pro Arg Asp Pro Glu Ile Glu Met Ser Gly Gly Leu Val
                405                 410                 415
Asn Gly Ser Ser Val Thr Val Ser Cys Lys Val Pro Ser Val Tyr Pro
             420                 425                 430
Leu Asp Arg Leu Glu Ile Glu Leu Leu Lys Gly Glu Thr Ile Leu Glu
         435                 440                 445
```

```
Asn Ile Glu Phe Leu Glu Asp Thr Asp Met Lys Ser Leu Glu Asn Lys
            450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
                500                 505                 510

Asp Thr Thr Val Leu Val Ser Pro Ser Ile Leu Glu Glu Gly Ser
            515                 520                 525

Ser Val Asn Met Thr Cys Leu Ser Gln Gly Phe Pro Ala Pro Lys Ile
            530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
            595                 600                 605

Pro Ser Glu Ser Val Lys Glu Gly Asp Thr Val Ile Ile Ser Cys Thr
610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
                660                 665                 670

Lys Val Gly Ser Gln Leu Arg Ser Leu Thr Leu Asp Val Gln Gly Arg
            675                 680                 685

Glu Asn Asn Lys Asp Tyr Phe Ser Pro Glu Leu Leu Val Leu Tyr Phe
            690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val (2) INFORMATION FOR SEQ ID NO:7:

(i) SEQUENCE CHARACTERISTICS:
        (A) LENGTH: 1566 base pairs
        (B) TYPE: nucleic acid
        (C) STRANDEDNESS: double
        (D) TOPOLOGY: linear (xi) SEQUENCE DESCRIPTION: SEQ ID NO:7:

GCATGCGCCA CCATGCCCAG CTAATTTTGT ATTTTTAGTA GAGATGGCGT TTCTCCATGT      60

TGGTCAGGCT GGTCTTGAAC TCCCGGCCTC AGGTGATCCG CCTGCCTCGG CCTCCCAAAG    120

TGGTGGGATT ACAGGCGTGA GCCACTGTGC CTGGCCTCCT TTTTATTTTT TTCACTGAAC    180

AAACCATGAA ACTTTCCCAG ATGTAAATAT CTATTTCCCA TTTTTCTTTT TTAAAATAA     240

GGCATTATTT TAACCATTTG AGTGTTAGAT ATTATTTTTA GATAATATTT TAATTTAGGC    300

ATAACTGCCG TGCAAAATCT GAAGATTAAT ATCTACCTTG TGAGTCATTC CTCTGTGAGA    360
```

```
CAGTGCATGT TAAATATGTT GAATTGGCAG GTGAAAAAGG AAGAAAAAAT GAGTAGTGAT      420

TGGTTATCCA CAGCTATGAA TGAGAAATTG AAGGTAGTAG ACTATGGATG ACAAACCTAT      480

TCTTGGTTTC CTTCTGTTTC TGAAATTCTA ATTACTACCA CAACTACATG AGAGACACTA      540

CTAACAAGCA AAGTTTTACA ACTTTTTAAA GACATAGACT TTATGTTATT ATAATTAAAA      600

ATCATGCATT TTTGTCATAT TAATAAAATT GCATATACGA TATAAAGGCA TGGACAAAGG      660

TGAAGTAGCT TCAAGAGACA GAGTTTCTGA CATCATTGTA ATTTTAAGCA TCGTGGATAT      720

TCCCGGGAAA GTTTTTGGAT GCCATTGGGG ATTTCCTCTT TACTGGATGT GGACAATATC      780

CTCCTATTAT TCACAGGAAG CAATCCCTCC TATAAAAGGG CCTCAGCCGA AGTAGTGTTC      840

AGCTGTTCTT GGCTGACTTC ACATCAAAAC TCCTATACTG ACCTGAGACA GAGGCAGCAG      900

TGATACCCAC CTGAGAGATC CTGTGTTTGA ACAACTGCTT CCCAAAACGG TAAGTGCAGA      960

ACGCTTTATA AGGGCAGCCT CGGGCCATGA ACACAGATA TGCAAAAGGC CTTCTAATAA      1020

AAACCACATC TGTACAAGCT CTTATTGTAT TGTAGCTAAA ACCTGTCTTT TCTCTTTGAC      1080

CTAAATAATG AAAGTCTTAA AATTTGTTTA TTTATTTGAT TAAACTCTGA AATAAAGATT      1140

ATTGCACTAG TGTCCTTTGC CCAAAATCTT AGGATGCTGC CTTAAACATC ATGGTAGAAT      1200

AATGTAACTA GCTACCCACG ATTTCCTTCT TTAATTCATT TTGTGTTTTA TCTCCCCAGG      1260

AAAGTATTTC AAGCCTAAAC CTTTGGGTGA AAAGAACTCT TGAAGTCATG ATTGCTTCAC      1320

AGTTTCTCTC AGCTCTCACT TTGGGTAAGT CAGTGCCATT AGACCAAGAT TTCTCATTCT      1380

CGCACTATAG ATATTTCAGA CTGAAATATC CTTGCTTGTC TGGGGCTGTC CTGCACAGGA      1440

TATCTGGCAG CATCCTTGAC CTCTACCTGC AATGTGTTCT TCCCTGGGCT TGGGGTCATT      1500

TACTTTACCT CTTGGTGTCT CCCTTTCCTT AAGTGTAAAG TGTGGATCCG TTGACCTGCA      1560

GGTCGA                                                                1566

(2) INFORMATION FOR SEQ ID NO:8:

(i) SEQUENCE CHARACTERISTICS:
         (A) LENGTH: 1032 base pairs
         (B) TYPE: nucleic acid
         (C) STRANDEDNESS: double
         (D) TOPOLOGY: linear (xi) SEQUENCE DESCRIPTION: SEQ ID NO:8:

AAGCTTCATT CTGCAATCAG CATTGTCCTT TATCTTTCCA GTAAAGATAG CCTTTTGGAG       60

TCGAAGATGA GGAAAAGCCT GTATTTTATA GTCTTGGAAG TGTCTTCTTT TGCCAGGACA      120

GAGAGAGGAG CTTCAGCAGT GAGAGCAACT GAAGGGGTTA ATAGTGGAAC TTGGCTGGGT      180

GTCTGTTAAA CTTTTTTCCC TGGCTCTGCC CTGGGTTTCC CCTTGAAGGG ATTTCCCTCC      240

GCCTCTGCAA CAAGACCCTT TATAAAGCAC AGACTTTCTA TTTCACTCCG CGGTATCTGC      300

ATCGGGCCTC ACTGGCTTCA GGAGCTGAAT ACCCTCCCAG GCACACACAG GTGGGACACA      360

AATAAGGGTT TTGGAACCAC TATTTTCTCA TCACGCAGAC AACTTAAAAT GCCTGGGAAG      420

ATGGTCGTGA TCCTTGGAGC CTCAAATATA CTTTGGATAA TGTTTGCAGC TTGTAAGTTC      480

TTTCCCTTCA TCTGTTTCAA ATGTTAGCAT TCAATTTTAG CCCTGGTTTT GGCTTCAGTC      540

AGTTTTGCGA TAGTAGTGAA GTAAAGACAC TAGGATTTTA AACAGTAGGA AAAGTTAATT      600

TAGTCTAACT TTTAATATGC AATTGAGTTT TGCTATATAC CATTGTACTG TCATAGTTAG      660

AGCTGAAAAT TGATGTTTTT GGTATCTTTT TTTCCAAAGG CAATTGAGTA ATTTGGATTC      720

TGTCTCTAGT CGGTCTGTCT CTTTAGTTTC CTATACTTGA CAATGAGGTC AAACTTAGCA      780
```

-continued

```
AATAACAAAA CAGCTTTGAT AAATGGGCAT CAAGGTTGGA ACTGAGAATT CTCTCTACTG      840

AAGATGATTC CATAAACTTT TTTGGCAGTG ACTTCGGTGC TTTTTGGCTA CCTTGCAGTT      900

AGTTTGAAGC AGCTTAGGAA AGAGATCAGT CTGATCATAT TTTAGACATT ATACAGAGAA      960

GAAGGAGGAG AATACTAGAC AAACTAGTGG TAAATTTGCT TCTGTCTTTT TTTGCTTTTG     1020

CAGCTCAAGC TT                                                         1032
```

(2) INFORMATION FOR SEQ ID NO:9:

(i) SEQUENCE CHARACTERISTICS:
        (A) LENGTH: 2175 base pairs
        (B) TYPE: nucleic acid
        (C) STRANDEDNESS: double
        (D) TOPOLOGY: linear (xi) SEQUENCE DESCRIPTION: SEQ ID NO:9:

```
GCGGCCGCCG CTCCTCCACG CCTGCGGACG CGTGGCGAGC GGAGGCAGCG CTGCCTGTTC       60

GCGCCATGGG GGCACCGTGG GGCTCGCCGA CGGCGGCGGC GGGCGGGCGG CGCGGGTGGC      120

GCCGAGGCCG GGGGCTGCCA TGGACCGTCT GTGTGCTGGC GGCCGCCGGC TTGACGTGTA      180

CGGCGCTGAT CACCTACGCT TGCTGGGGGC AGCTGCCGCC GCTGCCCTGG GCGTCGCCAA      240

CCCCGTCGCG ACCGGTGGGC GTGCTGCTGT GGTGGGAGCC CTTCGGGGGG CGCGATAGCG      300

CCCCGAGGCC GCCCCCTGAC TGCCGGCTGC GCTTCAACAT CAGCGGCTGC CGCCTGCTCA      360

CCGACCGCGC GTCCTACGGA GAGGCTCAGG CCGTGCTTTT CCACCACCGC GACCTCGTGA      420

AGGGGCCCCC CGACTGGCCC CCGCCCTGGG GCATCCAGGC GCACACTGCC GAGGAGGTGG      480

ATCTGCGCGT GTTGGACTAC GAGGAGGCAG CGGCGGCGGC AGAAGCCCTG GCGACCTCCA      540

GCCCCAGGCC CCCGGGCCAG CGCTGGGTTT GGATGAACTT CGAGTCGCCC TCGCACTCCC      600

CGGGGCTGCG AAGCCTGGCA AGTAACCTCT TCAACTGGAC GCTCTCCTAC CGGGCGGACT      660

CGGACGTCTT TGTGCCTTAT GGCTACCTCT ACCCCAGAAG CCACCCCGGC GACCCGCCCT      720

CAGGCCTGGC CCCGCCACTG TCCAGGAAAC AGGGGCTGGT GGCATGGGTG GTGAGCCACT      780

GGGACGAGCG CCAGGCCCGG GTCCGCTACT ACCACCAACT GAGCCAACAT GTGACCGTGG      840

ACGTGTTCGG CCGGGGCGGG CCGGGGCAGC CGGTGCCCGA AATTGGGCTC CTGCACACAG      900

TGGCCCGCTA CAAGTTCTAC CTGGCTTTCG AGAACTCGCA GCACCTGGAT TATATCACCG      960

AGAAGCTCTG GCGCAACGCG TTGCTCGCTG GGCGGTGCC GGTGGTGCTG GCCCAGACC      1020

GTGCCAACTA CGAGCGCTTT GTGCCCCGCG GCGCCTTCAT CCACGTGGAC GACTTCCCAA     1080

GTGCCTCCTC CCTGGCCTCG TACCTGCTTT TCCTCGACCG CAACCCCGCG GTCTATCGCC     1140

GCTACTTCCA CTGGCGCCGG AGCTACGCTG TCCACATCAC CTCCTTCTGG GACGAGCCTT     1200

GGTGCCGGGT GTGCCAGGCT GTACAGAGGG CTGGGGACCG GCCCAAGAGC ATACGGAACT     1260

TGGCCAGCTG GTTCAGCGG TGAAGCCGCG CTCCCCTGGA AGCGACCCAG GGGAGGCCAA     1320

GTTGTCAGCT TTTTGATCCT CTACTGTGCA TCTCCTTGAC TGCCGCATCA TGGGAGTAAG     1380

TTCTTCAAAC ACCCATTTTT GCTCTATGGG AAAAAAACGA TTTACCAATT AATATTACTC     1440

AGCACAGAGA TGGGGCCCG GTTTCCATAT TTTTTGCACA GCTAGCAATT GGGCTCCCTT     1500

TGCTGCTGAT GGGCATCATT GTTTAGGGGT GAAGGAGGGG GTTCTTCCTC ACCTTGTAAC     1560

CAGTGCAGAA ATGAAATAGC TTAGCGGCAA GAAGCCGTTG AGGCGGTTTC CTGAATTTCC     1620

CCATCTGCCA CAGGCCATAT TTGTGGCCCG TGCAGCTTCC AAATCTCATA CACAACTGTT     1680

CCCGATTCAC GTTTTTCTGG ACCAAGGTGA AGCAAATTTG TGGTTGTAGA AGGAGCCTTG     1740
```

-continued

```
TTGGTGGAGA GTGGAAGGAC TGTGGCTGCA GGTGGGACTT TGTTGTTTGG ATTCCTCACA      1800

GCCTTGGCTC CTGAGAAAGG TGAGGAGGGC AGTCCAAGAG GGGCCGCTGA CTTCTTTCAC      1860

AAGTACTATC TGTTCCCCTG TCCTGTGAAT GGAAGCAAAG TGCTGGATTG TCCTTGGAGG      1920

AAACTTAAGA TGAATACATG CGTGTACCTC ACTTTACATA AGAAATGTAT TCCTGAAAAG      1980

CTGCATTTAA ATCAAGTCCC AAATTCATTG ACTTAGGGGA GTTCAGTATT TAATGAAACC      2040

CTATGGAGAA TTTATCCCTT TACAATGTGA ATAGTCATCT CCTAATTTGT TTCTTCTGTC      2100

TTTATGTTTT TCTATAACCT GGATTTTTTA AATCATATTA AAATTACAGA TGTGAAAATA      2160

AAAAAAAGCG GCCGC                                                        2175
```

(2) INFORMATION FOR SEQ ID NO:10:

(i) SEQUENCE CHARACTERISTICS:
        (A) LENGTH: 2861 base pairs
        (B) TYPE: nucleic acid
        (C) STRANDEDNESS: double
        (D) TOPOLOGY: linear (xi) SEQUENCE DESCRIPTION: SEQ ID NO:10:

```
CTGCTCCTGC GCGGCAGCTG CTTTAGAAGG TCTCGAGCCT CCTGTACCTT CCCAGGGATG        60

AACCGGGCCT TCCCTCTGGA AGGCGAGGGT TCGGCCACA GTGAGCGAGG GCCAGGGCGG       120

TGGGCGCGCG CAGAGGGAAA CCGGATCAGT TGAGAGAGAA TCAAGAGTAG CGGATGAGGC       180

GCTTGTGGGG CGCGGCCCGG AAGCCCTCGG GCGCGGGCTG GGAGAAGGAG TGGGCGGAGG       240

CGCCGCAGGA GGCTCCCGGG GCCTGGTCGG GCCGGCTGGG CCCCGGGCGC AGTGGAAGAA       300

AGGGACGGGC GGTGCCCGGT TGGGCGTCCT GGCCAGCTCA CCTTGCCCTG GCGGCTCGCC       360

CCGCCCGGCA CTTGGGAGGA GCAGGGCAGG GCCCGCGGCC TTTGCATTCT GGGACCGCCC       420

CCTTCCATTC CCGGGCCAGC GGCGAGCGGC AGCGACGGCT GGAGCCGCAG CTACAGCATG       480

AGAGCCGGTG CCGCTCCTCC ACGCCTGCGG ACGCGTGGCG AGCGGAGGCA GCGCTGCCTG       540

TTCGCGCCAT GGGGGCACCG TGGGGCTCGC CGACGGCGGC GGCGGGCGGG CGGCGCGGGT       600

GGCGCCGAGG CCGGGGGCTG CCATGGACCG TCTGTGTGCT GGCGGCCGCC GGCTTGACGT       660

GTACGGCGCT GATCACCTAC GCTTGCTGGG GGCAGCTGCC GCCGCTGCCC TGGGCGTCGC       720

CAACCCCGTC GCGACCGGTG GGCGTGCTGC TGTGGTGGGA GCCCTTCGGG GGCGCGATA       780

GCGCCCCGAG GCCGCCCCCT GACTGCCGGC TGCGCTTCAA CATCAGCGGC TGCCGCCTGC       840

TCACCGACCG CGCGTCCTAC GGAGAGGCTC AGGCCGTGCT TTTCCACCAC CGCGACCTCG       900

TGAAGGGGCC CCCCGACTGG CCCCCGCCCT GGGGCATCCA GGCGCACACT GCCGAGGAGG       960

TGGATCTGCG CGTGTTGGAC TACGAGGAGG CAGCGGCGGC GGCAGAAGCC CTGGCGACCT      1020

CCAGCCCCAG GCCCCGGGC CAGCGCTGGG TTTGGATGAA CTTCGAGTCG CCCTCGCACT      1080

CCCCGGGGCT GCGAAGCCTG GCAAGTAACC TCTTCAACTG GACGCTCTCC TACCGGGCGG      1140

ACTCGGACGT CTTTGTGCCT TATGGCTACC TCTACCCCAG AAGCCACCCC GGCGACCCGC      1200

CCTCAGGCCT GGCCCCGCCA CTGTCCAGGA AACAGGGGCT GGTGGCATGG GTGGTGAGCC      1260

ACTGGGACGA CGCCAGGCC CGGGTCCGCT ACTACCACCA ACTGAGCCAA CATGTGACCG      1320

TGGACGTGTT CGGCCGGGGC GGGCCGGGC AGCCGGTGCC CGAAATTGGG CTCCTGCACA      1380

CAGTGGCCCG CTACAAGTTC TACCTGGCTT TCGAGAACTC GCAGCACCTG GATTATATCA      1440

CCGAGAAGCT CTGGCGCAAC GCGTTGCTCG CTGGGCGGT GCCGGTGGTG CTGGGCCCAG      1500

ACCGTGCCAA CTACGAGCGC TTTGTGCCCC GCGGCGCCTT CATCCACGTG GACGACTTCC      1560
```

```
CAAGTGCCTC CTCCCTGGCC TCGTACCTGC TTTTCCTCGA CCGCAACCCC GCGGTCTATC   1620

GCCGCTACTT CCACTGGCGC CGGAGCTACG CTGTCCACAT CACCTCCTTC TGGGACGAGC   1680

CTTGGTGCCG GGTGTGCCAG GCTGTACAGA GGGCTGGGGA CCGGCCCAAG AGCATACGGA   1740

ACTTGGCCAG CTGGTTCGAG CGGTGAAGCC GCGCTCCCCT GGAAGCGACC CAGGGGAGGC   1800

CAAGTTGTCA GCTTTTTGAT CCTCTACTGT GCATCTCCTT GACTGCCGCA TCATGGGAGT   1860

AAGTTCTTCA ACACCCATT TTTGCTCTAT GGGAAAAAAA CGATTTACCA ATTAATATTA   1920

CTCAGCACAG AGATGGGGGC CCGGTTTCCA TATTTTTTGC ACAGCTAGCA ATTGGGCTCC   1980

CTTTGCTGCT GATGGGCATC ATTGTTTAGG GGTGAAGGAG GGGGTTCTTC CTCACCTTGT   2040

AACCAGTGCA GAAATGAAAT AGCTTAGCGG CAAGAAGCCG TTGAGGCGGT TTCCTGAATT   2100

TCCCCATCTG CCACAGGCCA TATTTGTGGC CCGTGCAGCT TCCAAATCTC ATACACAACT   2160

GTTCCCGATT CACGTTTTTC TGGACCAAGG TGAAGCAAAT TTGTGGTTGT AGAAGGAGCC   2220

TTGTTGGTGG AGAGTGGAAG GACTGTGGCT GCAGGTGGGA CTTTGTTGTT TGGATTCCTC   2280

ACAGCCTTGG CTCCTGAGAA AGGTGAGGAG GGCAGTCCAA GAGGGGCCGC TGACTTCTTT   2340

CACAAGTACT ATCTGTTCCC CTGTCCTGTG AATGGAAGCA AAGTGCTGGA TTGTCCTTGG   2400

AGGAAACTTA AGATGAATAC ATGCGTGTAC CTCACTTTAC ATAAGAAATG TATTCCTGAA   2460

AAGCTGCATT TAAATCAAGT CCCAAATTCA TTGACTTAGG GGAGTTCAGT ATTTAATGAA   2520

ACCCTATGGA GAATTTATCC CTTTACAATG TGAATAGTCA TCTCCTAATT TGTTTCTTCT   2580

GTCTTTATGT TTTTCTATAA CCTGGATTTT TTAAATCATA TTAAAATTAC AGATGTGAAA   2640

ATAAAGCAGA AGCAACCTTT TTCCCTCTTC CCAGAAAACC AGTCTGTGTT TACAGACAGA   2700

AGAGAAGGAA GCCATAGTGT CACTTCCACA CAATTATTTA TTTCATGTCT TTACTGGACC   2760

TGAAATTTAA ACTGCAATGC CAGTCCTGCA GGAGTGCTGG CATTACCCTC TGCAGAACAG   2820

TGAAAGGTAT TGCACTACAT TATGGAATCA TGCAAAAAAA A                      2861
```

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:11:

```
GCGGCCGCTT TAGAGCACA                                                  19
```

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:12:

```
CTCTAAAGCG GCCGC                                                      15
```

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

TGTGAAGCTC CCTAAATTCC C                                              21

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (xi) SEQUENCE DESCRIPTION: SEQ ID NO:14:

TCGACGCGGC CGCG                                                      14

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO:15:

GGGGATTTCC                                                           10

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO:16:

AGGGATTTCC                                                           10

(2) INFORMATION FOR SEQ ID NO:17:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO:17:

GGGGAAACCC                                                           10

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:18:

GAGCTCGAGG CCGCACCATG CCTGGGAAGA TG                                  32

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:19:

CTAGCTAGCG CGTTTTACTT CAC                                    23

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:20:

CTAGCTTTCC AAGGTGAGTC CTA                                    23

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:21:

AGCTTAGGAC TCACCTTGGA AAG                                    23

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:22:

CCCAGGCATT TTAAG                                             15

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:23:

AUGCCUGGGA AGAUGGUCGU GAUCCUU                                27

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:24:

AAGAUGGUCG UGAUCCUU                                          18

(2) INFORMATION FOR SEQ ID NO:25:

(i) SEQUENCE CHARACTERISTICS:
        (A) LENGTH: 39 base pairs
        (B) TYPE: nucleic acid -continued

```
        (C) STRANDEDNESS: single
        (D) TOPOLOGY: linear (xi) SEQUENCE DESCRIPTION: SEQ ID NO:25:

AAGGAUCACC UGAUGAGUCC GUGAGGACGA AACCAUCUU                                          39
```

VCAM FUSION PROTEINS AND DNA CODING THEREFOR

This application is a division of U.S. application Ser. No. 08/342,642, filed Nov. 21, 1994, now abandoned which is a continuation of U.S. application Ser. No. 07/608,298, filed Oct. 31, 1990, now abandoned, which is a continuation-in-part of PCT/US90/02357 filed Apr. 27, 1990, and a continuation-in-part of U.S. application Ser. No. 07/452,675, filed Dec. 18, 1989, now U.S. Pat. No. 5,272,263, which is a continuation-in-part of U.S. application Ser. No. 07/359,516, filed Jun. 1, 1989, now abandoned, which is a continuation-in-part of U.S. application Ser. No. 07/345,151, filed Apr. 28, 1989, now U.S. Pat. No. 5,217,870. This application also claims priority from International application PCT/US90/02357, filed Apr. 27, 1990.

TECHNICAL FIELD OF INVENTION

This invention relates to molecules involved in the adhesion of leukocytes to endothelial cells during inflammation and to DNA sequences that code on expression for them. More particularly, it relates to Endothelial Cell Adhesion Molecules (ELAMs), including ELAM1 and Vascular Cell Adhesion Molecule 1 and 1b (VCAM1 and VCAM1b). It also relates to molecules on the surface of leukocytes involved in leukocyte adhesion to endothelial cells (MILAs). These include CDX, a molecule involved in the ELAM1 adhesion pathway, and VLA4, the ligand of VCAM1 and VCAM1b. This invention also relates to clone 7.2 and clone 1. These DNA sequences encode protein 7.2 and protein 1, respectively, which are involved in the expression of CDX. These proteins appear to be 1,3-fucosyl transferases that glycosylate CDX. This invention also relates to Pseudo-X and Pseudo-X$_2$, proteins that appear on COS 7 and CHO cells, respectively, that have been transfected with clone 7.2. Cells expressing those proteins bind ELAM1 and are recognized by anti-CDX monoclonal antibodies. This invention further relates to antibodies that recognize these adhesion molecules and anti-idiotype antibodies that recognize both those antibodies and the ligands or receptors for the adhesion molecules. The invention also relates to antigense DNA and RNA molecules complementary to mRNA for such adhesion molecules and also relates to ribozymes which recognize mRNA for such molecules. The invention also relates to methods for using the aforementioned molecules, DNA sequences, antibodies, anti-idiotype antibodies, antisense molecules and ribozymes, for example in developing diagnostic and therapeutic agents to detect or inhibit leukocyte adhesion to endothelial cells.

BACKGROUND OF THE INVENTION

Inflammation is the response of vascularized tissues to infection or injury. Clinically it is accompanied by four classic signs: redness, heat, pain and swelling. Its course may be acute or chronic.

At the cellular level, inflammation involves the adhesion of leukocytes (white blood cells) to the endothelial wall of blood vessels and their infiltration into the surrounding tissues. (Harlan, 1985.) Acute inflammation is characterized by the adhesion and infiltration of polymorphonuclear leukocytes (PMNs). (Harlan, 1987 and Malech and Gallin, 1987.) PMN accumulation in the tissues reaches its peak between two and one half to four hours after an inflammatory stimulus and ceases by about twenty-eight hours. (Bevilacqua and Gimbrone, 1987.) In contrast, chronic inflammation is characterized by the adhesion and infiltration of other leukocytes, especially monocytes and lymphocytes.

In normal inflammation, the infiltrating leukocytes phagocytize invading organisms or dead cells, and play a role in tissue repair and the immune response. However, in pathologic inflammation, infiltrating leukocytes can cause serious and sometimes deadly damage. Rheumatoid arthritis and atherosclerosis are examples of chronic inflammatory diseases in which mononuclear leukocytes infiltrate the tissues and cause damage. (Hough and Sokoloff, 1985 and Ross, 1986.) Multiple organ failure syndrome, adult respiratory distress syndrome (ARDS), and ischemic reperfusion injury are acute inflammations in which infiltrating PMNs cause the damage (Harlan, 1987 and Malech and Gallin, 1987). In multiple organ failure syndrome, which can occur after shock such as that associated with severe burns, PMN-mediated damage exacerbates the injury. In ARDS, PMNs cause the lungs to fill with fluid, and the victim may drown. In ischemic reperfusion injury, which occurs when tissue cut off from the supply of blood is suddenly perfused with blood (for example after heart attack, stroke, or limb re-attachment), PMN adhesion causes serious tissue damage (Harlan, 1987).

Recognizing that leukocyte infiltration is the cause of much inflammation-related pathology and that leukocyte adhesion is the first step in infiltration, investigators have recently focused attention on the mechanism of leukocyte binding to the endothelial cell surface. Studies show that binding is mediated by cell-surface molecules on both endothelial cells and leukocytes which act as receptor and ligand (Harlan et al., 1987; Dana et al., 1986; and Bevilacqua et al., 1987a).

During the course of inflammation, certain inflammatory agents can act on the leukocytes, making them hyperadhesive for endothelium. Known inflammatory agents include leukotriene-B4 (LTB4), complement factor 5a (C5a), and formyl-methionyl-leucyl-phenylalanine (FMLP). These agents activate a group of proteins called LeuCAMs. The LeuCAMs are dimers of the CD11 and CD18 proteins. One of the LeuCAMs, CD11a/CD18 (also called LFA1) binds to a receptor on endothelial cells called ICAM1 (intercellular adhesion molecule 1). (Harlan, 1985 and Dana et al., 1986.) Investigators have shown that monoclonal antibodies (Moabs) to LeuCAMs inhibit PMN adhesion to endothelium both in vitro and in vivo. (Arfors, 1987; Vedder et al., 1988; and Todd, 1989.)

Other inflammatory agents act directly on endothelial cells to substantially augment leukocyte adhesion. These agents include the cytokines interleukin-1 (IL-1), lymphotoxin (LT) and tumor necrosis factor (TNF), as well as the bacterial endotoxin, lipopolysaccharide (LPS). For example, IL-1 has been shown to stimulate adhesion of PMNs, monocytes, and the related cell lines HL-60 (PMN-like) and U937 (monocyte-like), to human endothelial cell monolayers. The action is both time-dependent and protein-synthesis dependent. (Bevilacqua et al., 1987a; Bevilacqua et al., 1987b; and Bevilacqua et al., 1985.)

Current evidence indicates that these agents induce a group of molecules on the endothelial cell surface called ELAMs (endothelial cell-leukocyte adhesion molecules). To date investigators have identified two of these molecules, intercellular adhesion molecule 1 (ICAM1) and endothelial cell-leukocyte adhesion molecule 1 (ELAM1). (Simmons et al., 1988; Staunton et al., 1988; and Bevilacqua et al., 1987b.) ICAM1 is found on many cell types, and its expression on vascular endothelium is strongly upregulated both in vitro and in vivo by the inflammatory cytokines interleukin-1 (IL-1), tumor necrosis factor-α (TNF), and gamma interferon (IFN-γ). (Pober et al., 1986; Dustin and Springer, 1988; and Cotran and Pober, 1988.)

ELAM1 was initially detected and characterized by a monoclonal antibody that partially blocked PMN adhesion to cytokine-treated human umbilical vein endothelial cells (HUVECs). ELAM1 is a 116 kD call surface glycoprotein rapidly synthesized by HUVECs in response to the inflammatory cytokines IL-1 or TNF, but not IFN-γ. (Bevilacqua et al., 1987b.) Unlike ICAM1, ELAM1 appears to be expressed only in endothelium, and its expression is transient even in the continued presence of cytokine. Like ICAM1, ELAM1 is present at inflammatory sites in vivo. Immunohistologic studies show that it exists at sites of acute, but not chronic, inflammation and is absent from the non-inflamed vessel wall. (Cotran et al., 1986 and Cotran and Pober, 1988.) Therefore, ELAM1 appears to be a major mediator of PMN adhesion to the inflamed vascular wall in vivo. Importantly, the presence of ELAM1 on the cell surface follows the natural course of acute inflammation, appearing a few hours after stimulation and gradually dissipating within a day. (Bevilacqua et al., 1987b.)

Indirect evidence suggests that other ELAMs exist. Although inflammatory agents induce binding of PMNS, monocytes, and lymphocytes to endothelium in vitro, Moabs against ELAM1 inhibit only the binding of PMNs and related cells. (Bevilacqua and Gimbrone, 1987.) Furthermore, maximal accumulation of lymphocytes and monocytes at sites of inflammation in vivo occurs at about twenty-four hours, when ELAM1 expression has returned to basal levels. On the basis of such information investigators inferred the presence of other ELAMs that mediate binding of these lymphocytes and monocytes. (Bevilacqua et al., 1987b.) As set forth in detail below, we have characterized and cloned two more ELAMS, designated VCAM1 and VCAM1b, that mediate binding of lymphocytes to endothelial cells. ELAMs accordingly may be regarded as a family of molecules.

A growing body of evidence indicates that ELAMs may play important roles in a wide range of pathological states involving cell-cell recognition, including tumor invasion, metastasis and viral infection. (Harlan, 1985; Wallis and Harlan, 1986; Bevilacqua et al., 1987a; and Cotran and Pober, 1988.)

The adhesion of leukocytes to cells expressing ELAMs suggests the existence on leukocytes of ELAM ligands. One such molecule is the ICAM1 ligand, lymphocyte function associated antigen 1 (LFA1). LFA1 is one of a trio of heterodimeric molecules known as the β2 integrins or the CD11/18 family. (Dustin et al., 1986; Rothlein et al., 1986; and Marlin and Springer, 1987.) Recent studies show that the ICAM1/LFA1 pathway plays a role in both lymphocyte and polymorphonuclear leukocyte (PMN) adhesion to endothelial cells in vitro. (Dustin and Springer, 1988; Smith et al., 1989.) We report here the isolation of a molecule involved in leukocyte adhesion to endothelial cells (MILA) which may prove to be an ELAM1 ligand. The molecule, designated CDX, is a protein of approximately 150 kD and was isolated from HL-60 cells. Monoclonal antibodies that recognize CDX inhibit the binding of PMNs and HL-60 cells to ELAM1-expressing cells. Furthermore, CDX is present on leukocyte cell types known to adhere to ELAM1 and is absent from leukocyte cell types and other cell types that do not adhere to ELAM1. Thus, CDX is a molecule expressed on certain leukocytes that plays an important role in ELAM1-mediated leukocyte-endothelial cell adhesion. We also report the isolation and sequencing of cDNA encoding molecules involved in CDX expression.

We also report the identification of a VCAM1 and VCAM1b ligand, VLA4. (Hemler and Takada, EP 330 506).

Antibodies specific for the $\alpha^4$ and $\beta_1$ subunits of VLA4 completely eliminate binding of VLA4-expressing cells to VCAM1.

Because leukocyte adhesion to the vascular wall is the first step in inflammation, therapies directed to preventing this step are attractive for the treatment of pathologic inflammation. Clinicians are already testing, with some success, therapies based on inhibiting leukocyte-mediated adhesion. One such approach involves Moab binding to the leukocyte cell-surface complex, CD11/CD18, to inhibit PMN adhesion. (Arfors et al., 1987; Vedder et al., 1988; and Todd et al., 1989.)

We believe that alternative therapies for preventing leukocyte adhesion, based on endothelial cell-mediated binding, and on ELAMs and MILAs (including ELAM ligands), in particular, are more promising. The ELAM system is particularly appealing for two reasons: First, because ELAM expression on endothelial cells is induced rather than constitutive, ELAMs are concentrated at sites of inflammation and are limited in number. This means that adhesion inhibitors need act only locally and, consequently, would be effective at lower doses than inhibitors directed to constitutively expressed molecules. Second, ELAM binding is selective for different leukocyte classes. For example, ELAM1 binds PMNs, and VCAM1 binds lymphocytes. Therefore, these therapies would be specific for certain classes of leukocytes and would not affect the circulation or migration of other leukocyte classes. Furthermore, for the above reasons, such therapies may prove to be cheaper and less toxic.

ELAM-based approaches to therapy require, as starting materials, both ELAMs and MILAs in highly purified form, free of normally associated animal proteins. There is also a need for methods to produce these molecules. These and other needs have now been met as described herein, by isolating DNA sequences that code on expression for particular adhesion molecules and by constructing recombinant DNA molecules and expression vehicles for their production.

SUMMARY OF THE INVENTION

It is the principal object of this invention to provide new means to study, diagnose, prevent and treat inflammation. More particularly, it is an object of this invention to provide molecules involved in leukocyte binding to endothelial cells and to isolate other molecules which are themselves useful in inhibiting the endothelial cell binding of leukocytes.

This invention provides DNA sequences that code on expression for endothelial cell-leukocyte adhesion molecules (ELAMs), genomic DNA sequences for ELAMs (including ELAM expression control sequences), recombinant DNA molecules containing these DNA sequences, unicellular hosts transformed with these DNA molecules, processes for producing ELAMs, and ELAM proteins essentially free of normally associated animal proteins. The present invention also provides for antibody preparations reactive for ELAMs.

This invention also provides DNA sequences that code on expression for molecules involved in leukocyte adhesion to endothelial cells (MILAs). MILAs will include leukocyte surface molecules that bind directly to ELAMs, i.e., ELAM ligands. Monoclonal antibodies recognizing ELAM ligands can inhibit ELAM/ELAM ligand binding directly. MILAs will also include leukocyte surface molecules that are involved indirectly in adhesion, for example molecules that inhibit ELAM/ELAM ligand binding by interacting with a third molecule, such as a monoclonal antibody. Such molecules may act, for example, by changing the surface conformation of an ELAM ligand so that its affinity for the ELAM is reduced. This invention also provides recombinant DNA molecules containing MILA DNA sequences and unicellular hosts transformed with them. It also provides for MILA proteins essentially free of normally associated animal proteins, methods for producing MILAs, and monoclonal antibodies that recognize MILAs, particularly CDX.

This invention provides DNA sequences encoding molecules that cause several cell lines, including COS, CHO and R1.1, both to express surface glycoproteins that are recognized by anti-CDX ($\alpha$-CDX) antibodies and to bind to ELAM1. This invention provides, in particular, clone 7.2 and clone 1, and protein 7.2 and protein 1, respectively. These proteins appear to be 1,3-fucosyl transferases.

This invention also provides the glycoproteins, Pseudo-X and Pseudo-$X_2$, which cause COS cells and CHO cells, respectively, to bind ELAM1 and to be recognized by $\alpha$-CDX antibodies.

This invention further provides methods for inhibiting PMN binding to endothelial cells involving the use of ELAMs, MILAs including ELAM ligands, or portions of those molecules to block receptors or ligands. It also relates to the use of antisense nucleic acids and ribozymes to inhibit ELAM expression. The invention also relates to methods for identifying binding inhibitors by screening molecules for their ability to inhibit binding of an ELAM to its ligand. It provides methods for identifying ELAMs and their ligands. One such method involves using anti-idiotypic antibodies against antibodies that recognize ELAMs or ELAM ligands.

BRIEF DESCRIPTION OF THE DRAWINGS

FIGS. 1A–E depict the composite ELAM1 cDNA sequence (SEQ ID NO:1) and deduced amino acid sequence derived from the DNA sequences of ELAM pCDM8 clone 6, pSQ148 and pSQ149. The nucleotides are numbered from 1 to 3863. Throughout this application we refer to the coding DNA sequence of this figure as the DNA sequence for ELAM1. We also refer to the molecule comprising the amino acid sequence depicted in this figure as ELAM1.

FIGS. 2A–D depict the sequence of cDNA coding for VCAM1 (SEQ ID NO:3) and the deduced amino acid sequence of VCAM1 (SEQ ID NO:5) derived from AM pCDM8 clone 41. The nucleotides are numbered 1 to 2811. In this application we refer to the coding DNA sequence of this figure as the DNA sequence for VCAM1. We also refer to the molecule comprising the amino acid sequence depicted in this figure as VCAM1.

FIGS. 3A–D depict the sequence of cDNA coding for VCAM1b (SEQ ID NO:4) and the deduced amino acid sequence of VCAM1b (SEQ ID NO:6) derived from VCAM1b pCDM8 clone 1E11. The nucleotides are numbered 1 to 3080. In this application we refer to the coding DNA sequence of this figure as the DNA sequence for VCAM1b. We also refer to the molecule comprising the amino acid sequence depicted in this figure as VCAM1b.

FIG. 4 depicts the domain structure of VCAM1. Amino acid number 25 of SEQ ID NO:5 corresponds to the first amino acid of FIG. 4. The amino acids are indicated according to the one letter code used by the University of Wisconsin Genetics Computer Group. (Devereux et al., 1984.)

FIG. 5 depicts the domain structure of VCAM1. Amino acid number 25 of SEQ ID NO:6 corresponds to the first amino acid of FIG. 5. The amino acids are indicated according to the one letter code used by the University of Wisconsin Genetics Computer Group. (Devereux et al., 1984.)

SEQ ID NO:7 depicts the DNA sequence of portions of the 5' untranslated and untranscribed region of ELAM1 derived from clone EL1-07.

SEQ ID NO:8 depicts the DNA sequence of portions of the 5' untranslated and untranscribed region of VCAM1 derived from clone VC1-16.

SEQ ID NO:9 depicts the sequence of cDNA coding for protein 7.2 derived from pSQ219 and CDX pCDM8 clone 7.2. The nucleotides are numbered 1–2175. In this application we refer to the coding DNA sequence of SEQ ID NO:9 as the DNA sequence for clone 7.2. We also refer to the polypeptide comprising the amino acid sequence encoded by SEQ ID NO:9 as protein 7.2.

SEQ ID NO:10 depicts the sequence of cDNA coding for protein 1 derived from clone 1. The nucleotides are numbered 1–2861. In this application we refer to the coding DNA sequence of SEQ ID NO:10 as the DNA sequence for clone 1. We also refer to the polypeptide comprising the amino acid sequence encoded by SEQ ID NO:10 as protein 1.

DETAILED DESCRIPTION OF THE INVENTION

In accordance with this detailed description, the following definitions apply:

Expression control sequence—A DNA sequence that controls and regulates the transcription and translation of another DNA sequence.

Operatively linked—A DNA sequence is operatively linked to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence, If a gene that one desires to insert into a recombinant DNA molecule does not contain an appropriate start signal, such a start signal can be inserted in front of the gene.

Antibody—An immunoglobulin molecule or functional fragment thereof, such as Fab, F(ab')$_2$ or dAb. An antibody preparation is reactive for a particular antigen when at least a portion of the individual immunoglobulin molecules in the preparation recognize (i.e., bind to) the antigen. An antibody preparation is non-reactive for an antigen when binding of the individual immunoglobulin molecules in the preparation to the antigen is not detectable by commonly used methods.

Standard hybridization conditions—salt and temperature conditions substantially equivalent to 5×SSC and 65° C. for both hybridization and wash. Under standard hybridization conditions the DNA sequences of this invention will hybridize to other DNA sequences having sufficient homology, including homologous sequences from different species. It is understood that the stringency of hybridization conditions is a factor in the degree of homology required for hybridization.

DNA sequences—The DNA sequences of this invention refer to DNA sequences prepared or isolated using recombinant DNA techniques. These include cDNA sequences, DNA sequences isolated from their native genome, and synthetic DNA sequences. The term as used in the claims is not intended to include naturally occurring DNA sequences as they exist in Nature.

ELAM—A molecule expressed on the surface of endothelial cells that mediates adhesion of leukocytes to endothelial cells.

MILA—A molecule expressed on the surface of leukocytes that is involved in ELAM-mediated binding to endothelial cells. This includes ELAM ligands, i.e., molecules that bind directly to ELAMs.

As described below, we have isolated and sequenced cDNAs from ELAM mRNAs, expressed ELAM moleculer in an appropriate host, isolated and sequenced cDNAs encoding MILAS, and isolated and expressed DNA sequences for MILAs.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or cleavage of a signal sequence to produce a "mature" protein. Accordingly, as used herein, the term "protein", including ELAM, MILA, protein 1, protein 7.2, Pseudo-X and Pseudo-$X_2$ encompass full-length polypeptides and modifications or derivatives thereof, such as glycosylated versions of such polypeptides, mature proteins, polypeptides retaining a signal peptide, truncated polypeptides having comparable biological activity, and the like.

ELAMs are expressed on the surface of endothelial cells only during inflammation. We utilized this phenomenon to isolate ELAM cDNAs. We have designated the polypeptides encoded by our cDNA isolates ELAM1, VCAM1 and VCAM1b. The first step involved in the isolation was selection of cells that differentially expressed the ELAM molecules. We chose human umbilical vein endothelial cells because they produce ELAMs when induced by the inflammatory cytokine, IL-1β. However, the practitioner is not limited to this cytokine, to this cell type, or even to human cells in particular. Other mammalian cells, e.g., baboon endothelial cells, are also known to produce ELAMs. (Cotran and Pober, 1988.)

The next step was to isolate mRNA from cells expressing ELAMs, in this case, IL-1β-induced HUVECs, and to create a cDNA library from them. Many methods are known for isolating mRNA and for producing cDNA from it. (See, e.g., Gubler and Hoffman, 1983 and Maniatis et al., 1982.)

We then inserted the cDNA into an appropriate vector. We chose the eukaryotic expression vector pCDM8, described by Brian Seed. (Seed, 1987.) This plasmid has several advantages including a high copy number in E. coli, a eukaryotic promoter, and high level of expression in transient expression systems such as COS 7 cells. However, several other vector systems are available. (See, e.g., Cate et al., 1986.)

After constructing a cDNA library, the next step was to isolate from it clones containing ELAM cDNA sequences. There are currently many ways to isolate cDNA for a differentially expressed mRNA. These include, for example, (1) plus/minus screening with labeled cDNA; (2) production of subtracted cDNA libraries; and (3) screening with subtractive cDNA probes. (Davis, 1986; Sargent, 1987; Davis et al., 1985, Hedrick et al., 1984; and Duguid et al., 1988.) We chose the third technique, screening with subtractive cDNA probes, and produced a cDNA sublibrary enriched for ELAM sequences.

As we will describe in more detail below, we produced a subtractive cDNA probe enriched for mRNA produced by cytokine-induced, but not uninduced cells. Then we probed the cytokine-induced cDNA library with the subtracted cDNA probe using techniques well known to the art. This enabled us to isolate clones forming a sublibrary enriched for ELAM sequences.

At this point we used two techniques to identify clones that contained cDNA for ELAM sequences. In a first method, we tested clones for expression of ELAM activity in an appropriate eukaryotic expression system. One can use a variety of direct expression techniques, including antibody screening of fusion proteins encoded by cDNA cloned in λGT11 (Young and Davis, 1983; Young and Davis, 1984); or activity assay of oocyte-conditioned media after injection of mRNA from cloned cDNA, or from plasmid or phage DNA carrying SP6/T7 promoters. Alternatively, one can make libraries in plasmid, phage, and cosmid vectors containing a variety of promoter, selection and replication elements. Animal cells may be transfected with the library for transient or stable expression. Transfection can be accomplished by a variety of methods. For transient expression, investigators have used spheroplast fusion, DEAE dextran, and electroporation. For stable expression they have used calcium phosphate, spheroplast fusion, and electroporation. We used COS 7 cells, a transient expression system, transfected by spheroplast fusion. (Aruffo and Seed, 1987.)

Until recently, identification of cloned molecules by direct expression has required sensitive assays and has been restricted to lymphokines. However, cDNA cloning of single-chain cell-surface molecules in efficient transient expression vectors (see, e.g., Seed and Aruffo, 1987 and Seed, 1987), either by antibody "panning" technology (Wysocki and Sato, 1978) or by identification of functional molecules by FACS (Yamasaki et al., 1988), has expanded the range of cloned molecules that one can identify by direct expression. We have extended this technology by using an adhesion assay in that an appropriate cell type, expressing the ligand for the cloned molecule, is used to identify that molecule.

We detected ELAM expression by testing the ability of transfected cells to bind either the human neutrophil-like cell line, HL-60 (Bevilacqua et al., 1985), or the human B-lymphocyte-like cell line, RAMOS (American Type Culture Collection, ATCC accession no. CRL 1596, human Burkitt lymphoma). We describe this in more detail below. Because the transfected cells were non-human, those producing human ELAM polypeptides did so in substantially purified form and essentially free of normally associated animal proteins. We picked cells that tested positive in this assay, collected the plasmid DNA, and isolated the inserts from them. These inserts contailed DNA sequences encoding ELAM1 (selected by adhesion to HL-60 cells) and VCAM1 (selected by adhesion to RAMOS cells).

In a second method, we identified cDNA inserts from the enriched sublibrary that hybridized on a Northern blot to a 4 kb band of induced, but not uninduced, mRNA. Two of these inserts contained DNA sequences for ELAM1. Other inserts from the sublibrary encode different induced mRNAs.

We isolated a cDNA for another VCAM, VCAM1b, by probing the IL-1β-induced HUVEC cDNA library with a random-primed oligonucleotide $^{32}$P-labeled probe derived from the VCAM1 cDNA sequence. VCAM1b is larger than VCAM1.

Using the clones identified by these three methods, we determined the sequences of cDNAs for ELAM1 ana VCAM1 and 1b. It should be noted that due to the degeneracy of the genetic code, one may alter many of the nucleotides of these sequences and retain DNA sequences that code on expression for an amino acid sequence identical to those encoded by the DNA sequences we have presented in FIGS. 1 (SEQ ID NO:1), 2 (SEQ ID NO:3) and 3 (SEQ ID NO:4). Additionally, DNA sequences for fragments of the ELAM cDNA sequences, or DNA sequences that are substantially homologous to the ELAM cDNA sequences and that themselves encode ELAM polypeptides, would hybridize to the disclosed ELAM cDNA sequence under standard hybridization conditions.

From the DNA sequences described above, we deduced the amino acid sequences of ELAM1, VCAM1 and VCAM1b. It should be clear that given the current state of the protein-engineering art, an artisan could make purposeful alterations, insertions or deletions in these amino acid sequences and obtain a variety of molecules having substantially the same biological or immunological activities as those of the molecules we have disclosed herein.

We have also isolated genomic DNA sequences, including transcriptional promoters, for the ELAM1 and VCAM1 and 1b genes. We screened a human genomic library with $^{32}$P-labeled probes derived from the coding regions of the ELAM1 or VCAM1 DNA sequences. This yielded clones that contained portions of the 5' untranscribed and untranslated regions of both the ELAM1 and VCAM1 gene.

ELAM1 and VCAM1 transcriptional promoters have a number of uses. First, they are useful to construct vectors inducible by cytokines (such as TNF or IL-1), and bacterial lipopolysaccharide (LPS), or any other agent found to induce expression of ELAMs in endothelial cells. Such vectors may be useful, for example, in gene transfer assays, wherein the inducible promoter is positioned so that it drives transcription of a reporter gene such as chloramphenicol acetyltransferase, beta-galectosidase, luciferase, etc. This construct will then be introduced transiently or stably into an appropriate mammalian cell line. Potential inhibitors or stimulators of induction can then be assayed by measuring their effect on induction by any or all of the inducers listed above.

We have also isolated a hybridoma producing monoclonal antibodies recognizing ELAM1, designated BB11. We describe its production in Example V, infra.

VCAM1 is involved in T and B cell binding to endothelial cells. T cells activated by lectin stimulation or by a specific antigen bind to HUVECs in vitro. This binding is mediated in part by the ICAM/LFA1 pathway, since monoclonal antibodies that bind to an inhibitory epitope on CD18 (the common β chain of LFA1) partially inhibit T cell binding. We found that anti-CD18 and anti-VCAM1 monoclonals completely inhibited binding. Coupled with the observations that humans deficient in CD18 exhibit normal recruitment of lymphocytes to sites of inflammation, and that activated T cells do not recirculate through the lymphatic system (i.e., they will not exit from the blood stream except at sites of inflammation), this implies that VCAM1 is central to activated T cell migration in vivo. Thus, VCAM1 serves to focus all activated T cells into an inflammatory site. Since the presence of activated T cells is the hallmark of numerous inflammatory and autoimmune diseases, this in turn implies that inappropriate expression of VCAM1 might be the fundamental pathochemical characteristic of such diseases. Therefore, the VCAM1 pathway may provide a key intervention point for diseases where activated T cell recruitment is involved, e.g., arthritis, lupus, multiple sclerosis, etc. Therefore, we disclose a therapeutic treatment to inhibit T cell binding to the endothelium by blocking the VCAM1 binding pathway. This may be accomplished by any of the means we describe herein.

The DNA sequence of VCAM1 reveals that the molecule has no structural similarity to ELAM1 but is a member of the immunoglobulin supergene family. Three of the Ig superfamily members are established cell-cell adhesion molecules. These are NCAM, CEA, and ICAM1. NCAM binds to itself on the surface of other cells (homotypic adhesion) thus promoting adhesion between cells of the same type. The function of CEA was unknown until recently, when it was discovered to function as an adhesion molecule, mediating homotypic aggregation of colon tumor cells as well as cells transfected with the cDNA for CEA. (Benchimol et al., 1989.) ICAM1 is a ligand for the leukocyte surface protein, LFA1, and mediates both leukocyte-leukocyte and leukocyte-endothelial cell adhesion. (Staunton et al., 1988.) ICAM1 and VCAM1 possess some functional similarities, e.g., both are induced in endothelial cells after treatment with cytokines, and both mediate adhesion of lymphocytes and related cell lines. The ligand for ICAM1, LFA-1, has been well-characterized. The ligand for VCAM1 has been identified as VLA4 (see, infra). ICAM1 is believed to play a role not only in the migration of lymphocytes to sites of inflammation in vivo but also in numerous lymphocyte functions related to the immune response. Additionally, ICAM1 has recently been shown to be the receptor for many of the rhinoviruses. Receptors for other viruses (e.g., polio, HIV) are also members of the Ig superfamily. (White and Littman, 1989.) Thus, VCAM1 may play a critical role in both immune regulation and viral infection.

Both CEA and ICAM1 are expressed on tumor cells. CEA has been used as a diagnostic marker for colon cancer for many years. Recent diagnostic techniques include the use of radioimmunoconjugates in which anti-CEA antibodies are bound to radioactive markers and introduced into the patient. Using this method, clinicians have been able to identify tumors as small as three millimeters. (Goldenberg, 1989.)

Investigators are also exploring radioimmunotherapy and immunotoxin therapy. Radioimmunotherapy involves the use of radioimmunoconjugates in which nucleotides such as $^{125}$I, $^{90}$y, $^{186}$Re and the like are bound to antibodies recognizing a particular surface antigen. Immunotoxins are antibodies conjugated with cell toxins, such as Pseudomonas exotoxin and the like. Upon injection, these conjugated antibodies target the toxic agents to cells expressing the antigen. In accordance with this invention, radioactive markers, nuclides and cellular toxins may be conjugated with VCAM1 and 1b or antibodies recognizing them to target cells expressing VCAM1 ligands (e.g., VLA4) or VCAM1.

The discovery of new ELAMs or the future discovery of ELAMs or MILAs being expressed on other cells, such a tumor cells, also makes possible new TIL therapies. For example, where a tumor is discovered which expresses an ELAM on its surface, the tumor can be biopsied and infiltrated lymphocytes can be removed. A gene for a tumorcidal agent, such as TNF in a retroviral expression vector, is then used to transfect the tumor infiltrating lymphocytes (TILs), which are then expanded with IL-2. When the transfected TILs are injected back into the patient, the TILs are specifically directed to the original tumor and migrate back into the tumor, where the tumorcidal gene product is released for local effect. (See, Thomas and Sikora, 1989.) Since all ELAMs bind some form of leukocyte and thereby mediate infiltration, modified TIL therapies in which infiltrated leukocyte cells are isolated, transfected for expression of a particular desired gene product, amplified and reintroduced to the patient are contemplated herein.

An alternative TIL therapy takes advantage of the fact that certain cell types, notably some forms of cancer cells, express ELAMs or MILAs. For example, colon carcinomas are known to express CDX and melanomas express VLA4.

Employing the DNA sequences disclosed herein, a therapy can be designed to enhance and improve the cytolytic activity of leukocytes by transfecting them to express surface ELAMs or MILAs, thereby improving their binding to target cells expressing the corresponding ligand. Where the cytolytic activity of a leukocyte cell type is increased as a function of stronger cell-cell adhesion, such a method would improve the ability of leukocytes to destroy targeted cells. For example, in the case of colon carcinoma or melanoma, leukocytes (preferably infiltrating leukocytes, which already have an affinity for the target cancer cell) may be transfected with an expression vector including a gene for ELAM1 (in the case of colon carcinoma) or VCAM1 or VCAM1b (in the case of melanoma). Introducing such leukocytes into the patient provides a population of leukocytes capable of homing in on the carcinoma or melanoma cells, respectively, which leukocytes have enhanced ability to adhere to those cells to produce the desired cytolytic effect.

We have also found that incubating HUVECs with TNF and IFN-γ together increases VCAM1 expression about one-hundred percent over incubation with TNF alone. Activated T cells secrete IFN-γ, and therefore may promote their own recruitment to inflammatory sites through a positive feedback system: VCAM causes T cell binding, T cells further stimulate VCAM production via IFN-γ secretion. Thus, we have devised a new treatment for VCAM-dependent pathologies which involves inhibition of this feedback mechanism. The treatment comprises inhibiting cytokines such as IL-1, TNF or IFN-γ, for example with monoclonal antibodies, to block cytokine-stimulated production of VCAM.

We have also isolated a MILA, CDX, that is involved in ELAM1-mediated adhesion and, in fact, is probably the (or an) ELAM1 ligand. The isolation involved, as a first step, the production of monoclonal antibodies against the CDX molecule. We immunized mice with whole HL-60 cells, a PMN-related cell line, that was known to bind to ELAM1. Alternatively, one could immunize with any cell line that binds to ELAM1, including PMNs themselves and, as we shall show, U937 cells. In addition, to isolate MILAs involved in adhesion to other ELAMS, one could immunize with any cell line that binds to the appropriate ELAM. For example, in isolating VCAM1, we have identified two such cell lines: The β2-lymphocyte-like cell line, RAMOS, and the T-lymphocyte-like cell line, JURKAT.

After finding that immune serum from the immunized mice inhibited binding of HL-60 cells to HUVECs in the adhesion assay We will describe, we created hybridomas from spleen cells in a manner well known to the art. (Goding, 1983.) Then we identified those hybridomas that produced monoclonal antibodies against CDX by testing their ability in the adhesion assay to inhibit binding of HL-60 cells to induced HUVECs. We used several of these hybridomas to produce ascites fluid containing monoclonal antibodies.

One can also generate monoclonal Fab fragments recognizing these antigens using the technique of Huse et al. (1989). (See also Skerra and Plückthun, 1988.) Alternatively, one can produce single domain antibodies as described by Ward et al. (1989).

Our monoclonal antibodies against CDX possess the following characteristics; First, they inhibit binding of HL-60 cells or PMNs to cells that express ELAM1. Second, these antibodies exhibit a specific cell-binding pattern—they recognize cells that bind to ELAM1, but they do not recognize cells that do not bind to ELAM1. Third, they have a recognition pattern for human cell lines that is distinct from the pattern of antibodies against other cell-surface molecules, such as anti-LFA-1, anti-LFA-3, anti-CD44, anti-ICAM, anti-CD4, and anti-Leu8.

We used these Moabs to isolate CDX. We radioactively labeled HL-60 surface proteins and surface proteins from neutrophils (isolated from human blood) with iodine using a modification of a method described by Kurzinger (Kurzinger et al., 1981) or metabolically with $^{35}$S-methionine. We solubilized the membrane proteins and incubated them with an anti-CDX monoclonal bound through a μ-chain-specific rabbit anti-mouse IgG to Protein A sepharose (ARX), and then we isolated the antibody-bound protein. This protein is CDX isolated substantially free of normally associated animal proteins. The protein appears on SDS-PAGE as a single, diffuse band of about 150 kD. a 90 kD protein band was sometimes observed in the bound proteins from HL-60 cells and always in the proteins from neutrophils. We believe this 90 kD band represents a CDX degradation product. We also sometimes observed higher molecular weight bands (i.e., around 170 kD). These may be non-specific bands. When the isolated 150 kD protein was treated with N-glycanase, the molecular weight was reduced to approximately 70 kD. When the 150 kD band was treated with N-glycanase and O-glycanase, the molecular weight was not further reduced. We believe this represents the protein core of a very heavily glycosylated protein.

We have isolated two DNA sequences, clone 7.2 and clone 1, that appear to encode 1,3-fucosyl transferases that glycosylate the CDX polypeptide and impart to it the ability to bind ELAM1. 1,3-fucosyl transferases are highly specific enzymes that function in the Golgi apparatus and endoplasmic reticulum to attach fucosyl moieties to appropriate acceptor carbohydrates through a 1,3 glycosidic linkage. The genetic structure of these sequences is consistent with that of other, known glycosyl transferases. Furthermore, CHO cells trinsfected with clone 7.2 express fucosyl transferase activity.

Several 1,3-fucosyl transferases are known to the art. (Paulson and Colley, 1989 and Kukowska-Latallo et al., 1990.) These proteins of similar activity share little sequence homology between themselves or other glycosyl transferases. (Paulson and Colley, 1989 and Kukowska-Latallo et al., 1990.) Therefore, we would not expect these DNA sequences to share homology with the DNA sequences of this invention. However, other species are likely to contain homologous genes that share significant sequence homology with the DNA sequences disclosed here. One can isolate these homologous genes using the DNA sequences of this invention as probes under standard hybridization conditions. This invention specifically contemplates and encompasses such sequences.

When COS 7 cells were transfected with either of these two clones, they behaved like cells expressing CDX, that is, they became "visible" to ELAM1 in that they were able to produce a surface glycoprotein to which ELAM1 binds and which are recognized by the α-CDX monoclonal, $SGB_3B_4$. Using α-CDX monoclonals, we immunoprecipitated a 130 kD glycoprotein from transfected COS cells, which we have designated Pseudo-X. Similarly, CHO cells transfected with clone 7.2 also became visible to ELAM1 and α-CDX. They express a 140 kD glycoprotein which we have designated Pseudo-$X_2$.

Neither Pseudo-X nor Pseudo-$X_2$ are CDX. Pseudo-X has a molecular weight of about 130 kD and Pseudo-$X_2$, of 140 kD. CDX has a molecular weight of 150 kD. When treated with N-glycanase or hydrofluoric acid (which removes all carbohydrate)., Pseudo-X shifts to 110 kD. Pseudo-$X_2$ shifts to approximately 120 kD. CDX shifts to about 70 kD. Neither migrates at 46 kD or 59 kD, the predicted molecular weights of protein 7.2 and protein 1. Pseudo-X and CDX also have different V8 and chymotrypsin digestion patterns.

We isolated clone 7.2 and clone 1 as follows: We created a cDNA library from mRNA of a human cell line, HL-60, that expresses CDX. We enriched this library by using subtraction techniques, as we describe below, with a human cell line that does not express CDX, in this case HeLa cells. This produced a subtracted library containing about 2100 clones. We transfected a monkey kidney cell line, COS 7, with the subtracted library which we assayed in a number of ways.

We incubated the transfected cells with the α-CDX monoclonal antibodies and panned them on plates coated with anti-mouse IgG or IgM (Wysocki and Sato, 1978); cells binding to the plates would be those expressing a molecule recognized by α-CDX Moabs. In this manner, we identified adherent cells transfected with a 2.1 kb DNA insert. We subcloned a portion of this sequence into a sequencing vector and designated it pSQ219. The DNA insert in the pCDM8 clone was designated clone 7.2. We also isolated a 2.9 kb insert by hybridization, which we designated clone 1. These two clones encode protein 7.2 and protein 1, respectively.

We are also isolating a DNA sequence that codes on expression for CDX using technique known to the art. Some practical techniques involve using expression systems to express cloned DNA. As we have mentioned, a variety of eukaryotic expression systems are available.

One can isolate a DNA sequence encoding CDX using antibodies that recognize the CDX polypeptide, rather than the CDX glycoprotein. These antibodies are used to probe an HL-60 cDNA library like the one we described above.

Another method for isolating a DNA sequence encoding CDX (or another MILA) would employ fluorescent-antibody labeling. In this method, CDX-expressing cells are incubated with α-CDX Moabs and then the Moabs are labeled with, e.g., fluorescently tagged anti-mouse antibody. Cells binding the fluorescent antibodies may then be sorted with a fluorescence activated cell sorter (FACS). The DNA from the sorted cells may be used to transform a bacterial host such as *E. coli*. DNA from the resulting colonies may then be used to transfect COS 7 cells, and this procedure may be repeated until a single CDX-expressing clone is identified.

A third method is to pan the transfected calls as described above on plates coated with recombinant soluble ELAM1 (rsELAM1). We describe a method to coat plates with rsELAM1 in Example VIII. Cells binding to the plates will be those expressing CDX. Other soluble ELAMs can similarly be used to isolate cells expressing their ligands or MILAs involved in their adhesion pathways.

An expression library may also be created in *E. coli*. For example, a λ ZAP® (Stratagene)/HL-60 library may be constructed and used to express the inserted DNA in *E. coli*. After plating, the plaques can be directly screened with, e.g., radioactively labeled α-CDX monoclonals. (Young and Davis, 1983 and Young and Davis, 1984.) The plaques to which the monoclonals bind can be picked and the DNA insert isolated from them.

Another method we are using to identify ELAM ligands, not based on antibody recognition, is to transfect COS 7 cells with an appropriate library, that may be subtracted, and then pan them directly onto ELAM-expressing cells (such as induced HUVECS, ELAM-expressing COS 7 cells, or ELAM-expressing CHO cells). Once again, multiple rounds of panning are required to enrich the library sufficiently to isolate the pertinent clones.

Another technique for isolating the DNA sequences coding for CDX (or other MILAs) involves screening a cDNA library with oligonucleotide probes. By purifying a sufficient quantity of CDX, for example by affinity chromatography using immobilized antibody to CDX or immobilized ELAM1, one may determine a partial amino acid sequence and synthesize oligonucleotide probes that correspond to at least a portion of the CDX gene. These probes may then be used to screen the cDNA library. Alternatively, the oligonucleotides may be used as primers to generate long probes to be used in screening the library for CDX (MILA) genes.

We have also identified a ligand for VCAM1 and VCAM1b. It is the integrin VLA4. (Hemler, 1988; Hemler et al., 1987a; and Hemler et al., 1987b.) The integrins are a group of cell-extracellular matrix and cell-cell adhesion receptors exhibiting an αβ heterodimeric structure. (Hynes, 1987; Marcantonio and Hynes, 1988.) Investigators have identified three subfamilies of integrins categorized according to the β subunit. The VLA (very Late Antigen) proteins belong to the $β_1$ subfamily, many of whose members are specialized for cell-extracellular matrix attachment. (Hynes, 1987 and Ruoslahti, 1988.) VLA4 is expressed in relatively high levels on lymphoid cells (such as B and T cells) and myeloid cells, but is hardly detectable in other cells (Hemler et al., supra.) The binding of B and T cells to the extracellular matrix is mediated by VLA4 and its ligand, human fibronectin (FN). (Wayner et al., 1989.) The discovery that VLA4 is a ligand for VCAM1 is important because it now defines one binding pathway of B and T lymphocytes to activated endothelial cells. Therefore, we describe the use of VLA4 and VCAM1 and 1b as ligand and receptor in the methods described below.

We contemplate several uses for ELAM and MILA DNA sequences and molecules in the present invention. First, one may use ELAMs and MILAs to produce monoclonal antibody preparations that are reactive for these molecules. The Moabs may be used in turn as therapeutic agents to inhibit leukocyte binding to endothelial cells.

Second, one may use a soluble form of ELAM, 'soluble ELAM ligand or fragments of either as binding inhibitors. The ELAM peptides would bind to the ELAM ligand on leukocytes, and the ELAM ligand would bind to ELAM on endothelial cells. Both methods would thereby inhibit leukocyte binding to endothelial cells. To produce recombinant soluble ELAM (rsELAM) or rsELAM ligand one preferably would alter a DNA encoding those molecules to eliminate the transmembrane region. Thus, DNAs for soluble molecules would include all or part of the extracellular domain, perhaps attached to the cytoplasmic domain. This approach has already been validated using soluble CD4, the surface protein on T-cells that binds to the AIDS virus. (Fisher et al., 1988.) This approach also avoids the problems of antibody therapy, since the polypeptides used would be less likely to induce an immune response.

One problem investigators have encountered with soluble recombinant molecules is a short in vivo plasma half-life. (Capon et al., 1989.) Because such molecules are quickly cleared from the system, large doses or frequent injections are necessary to have a therapeutic effect. Therefore, investigators have sought methods to increase the half-life of soluble molecules. A potential solution is to link the soluble molecule to another molecule known to have a longer half-life in the blood stream. Due to their long half life, immunoglobulin molecules are promising candidates. Capon et al. (1989) have described the linking of soluble CD4 to an immunoglobulin molecule using recombinant DNA techniques. In this approach, one replaces the variable region of an immunoglobulin molecule with the soluble protein, forming a protein/immunoglobulin fusion protein.

It is expected that the rsELAM/immunoglobulin fusion proteins will have greater plasma half-life than rsELAM alone. Such fusion proteins are preferably produced with recombinant constructs, fusing a DNA sequence encoding the soluble molecule to a DNA sequence encoding the constant domain of an immunoglobulin molecule. The recombinant DNA may then be expressed in an appropriate host cell, preferably an animal cell, to produce the fusion protein.

We expect ELAM/immunoglobulin fusion proteins to have another advantage. Because immunoglobulin molecules are normally bivalent (i.e., they have two binding sites) an ELAM/immunoglobulin fusion protein would have two ELAMs and so, two ELAM ligand binding sites. Therefore, one would expect them to have greater affinity or avidity for cells displaying ELAM ligands.

Third, one may use molecules binding to ELAMs (such as anti-ELAM antibodies, or markers such as the ligand or fragments of it to detect inflammation. This involves, for example, making a molecule detectable by fluorescence or radioactivity, administering it to a patient and determining where in the body it accumulates. In this way one could also identify the type of inflammation. For example, binding to ELAM1 would indicate acute, as opposed to chronic inflammation.

Fourth, if an ELAM binds to its ligand through a carbohydrate moiety or some other post-translational modification, one could use ELAM to identify the carbohydrate on the ELAM ligand to which it bound.

Fifth, one could use ELAMs and MILAs as part of a system to screen small molecules for adhesion inhibitors. For example, one could create an assay system in which small molecules are tested for the ability to inhibit the interaction between CDX and ELAM1. Small molecule inhibitors identified in this way would provide candidates for anti-inflamatory drugs.

Sixth, one could use these molecules to identity endogenous proteins that inhibit leukocyte binding to ELAMS. Investigators have tentatively identified one such molecule, leukocyte adhesion inhibitor (LAI), that is involved in detaching bound PMNs from endothelium. (Wheeler et al., 1988.)

Seventh, one can generate VCAM/ICAM fusion proteins. We know that both proteins are composed of several structural domains. (Simmons et al., 1988.) DNA sequences encoding various domains of each protein are fused using, for example, the genetic fusion techniques we describe for making ELAM/immunoglobulin fusion proteins. The domains chosen are those having the ability to bind VCAM1 or VCAM1b ligands and ICAM1 ligands, respectively. Domains binding VLA4 and LFA1, the known ligands, are preferable. The polypeptides produced on expression of these DNA sequences are useful because they would block adhesion of any cell having a ligand to either VCAM1 or VCAM1b, or ICAM1 or both.

Finally, one could use ELAM and ELAM ligand DNA sequences to produce nucleic acid molecules that intervene in ELAM or ELAM ligand expression at the translational level. This approach utilizes antisense nucleic acid and ribozymes to block translation of a specific mRNA, either by masking that mRNA with an antisense nucleic acid or cleaving it with a ribozyme. These methods will be useful in treating inflammatory conditions.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into ELAM-producing cells. Antisense methods have been used to inhibit the expression of many genes in vitro. (Marcus-Sekura, 1988; Hambor et al., 1988.)

Ribozymes are RNA molecules possessing the ability to specifically cleave other single stranded RNA molecules in a manner somewhat analogous to DNA restriction endonucleases: Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it. (Cech, 1988.) Because they are sequence-specific, only mNAs with particular sequences are inactivated.

Investigators have identified two types of ribozymes, Tetrahymena-type and "hammerhead"-type. (Hasselhoff and Gerlach, 1988.) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen-base recognition sequences are preferable to shorter recognition sequences.

The DNA sequences described herein may thus be used to prepare antisense molecules against, and ribozymes that cleave, mRNAs for ELAM1, VCAM1 and VCAM1b, CDX and VLA4.

Antisense molecules and ribozymes may be used in methods to treat inflammation by introducing into calls molecules that interfere with the expression or adhesion molecules. Since ELAMs are induced on endothelial cells during inflammatory episodes, and since therapeutic agents can be delivered to vascular endothelium easily by intravenous injection, endothelial cells are attractive targets for such therapies, provided the antisense molecules or ribozymes can be delivered effectively to the appropriate cells.

Investigators have suggested two approaches which could be used to deliver these molecules to target cells. The first involves transfecting the target cell with a vector that expresses the anti-ELAM antisense nucleic acid or the ELAM-specific ribozyme as an mRNA molecule. (Hambor et al., supra.) While this approach is very useful when dealing with cell lines in vitro, it may not be as effective in vivo. A second approach that is more promising for in vivo delivery involves loading liposomes with anti-ELAM antisense molecules, ELAM-specific ribozymes or vectors which express them. These liposomes could also contain anti-ELAM monoclonal antibodies to direct the liposome to sites of inflammation. This form of delivery would provide a negative feedback system, since appearance of an ELAM on a cell would make the cell a target for suppression; and successful penetration of the antisense or ribozyme component would halt ELAM production, thereby eliminating the cell as a target.

Another feature of this invention is the expression of the ELAM, MILA and other DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequences, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAs, e.g., the numerous derivatives of phage λ, e.g., NM989, and other phage DNA, e.g., M13 and Filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention, Such useful expression control sequences include, for example, the early and late promoters of SV40 or adenovirus, the lac system, the third system, the TAC or TRE system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokariotic hosts such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

It will also be recognized, that expression of the DNA sequences of the present invention may have different effects in different hosts. For example, whereas clone 7.2 expressed in COS cells leads to the appearance of an ELAM1-binding surface molecule, expression of clone 7.2 in, e.g., prokaryotic host cells may have no similar effect, since prokaryotes lack internal cell structures (e.g., Golgi apparatus) that may be necessary for the biological functionality of protein 7.2. On the other hand, for isolation and purification of the clone 7.2 expression product intact, host cells in which protein 7.2 does not have a function in the cellular biochemistry (such as the catalytic role of a glycosyl transferase) may be preferred. The practitioner will be able to select the appropriate host cells and expression mechanisms for a particular purpose.

Considering these and other factors, a person skilled in the art will be able to construct a variety of vector/expression control sequence/host combinations that will express the DNA sequences of this invention on fermentation or in large scale animal culture.

Several strategies are available for the isolation and purification of protein 7.2 and protein 1 after expression in a host system. One method involves expressing the proteins in bacterial cells, lysing the cells, and purifying the protein by conventional means. Alternatively, one can engineer the DNA sequences for secretion from cells. For example, Colley et al. (1989) describe purifying a sialyltransferase by engineering the cleavable signal peptide of human gamma-interferon onto the DNA sequence for the transferase. Larsen et al. (1990) fused the DNA sequence for protein A to the amino-torminal and of a fucosyl transferase gene and expressed it as an excreted fusion protein. In these constructions, one can optionally remove the transmembrane region of these proteins that exist near the amino terminus. After secretion the proteins are purified from the medium. Similar strategies are available for bacteria.

Increasingly scientists are recognizing the value of enzymes as catalysts in organic synthetic. (Wong, 1989.) The 1,3-fucosyl transferases of this invention are useful for enzymatic synthesis of carbohydrates in vitro. Specifically, they are useful for catalyzing the linkage of fucose to appropriate receptors through a 1,3 glycosidic bond. We describe one set of suitable conditions for this catalysis in Example XII, relating to an assay for fucosyl transferase activity. One skilled in the art will recognize other suitable conditions under which the 1,3 fucosyl transferases described herein may be advantageously employed.

It is now clear that the carbohydrate moiety of CDX is important in ELAM1-mediated cell adhesion. A molecule comprising the carbohydrate moiety of CDX, Pseudo-X or Pseudo-$X_2$, or a fucose-containing portion of that moiety may be sufficient to function as an ELAM1 ligand. Such molecules may be useful in methods, including therapies, directed to inhibiting ELAM1-mediated cell adhesion.

This invention is also directed to small molecules that inhibit the activity of the 1,3-fucosyl transferases described herein, including synthetic organic chemicals, natural fermentation products, peptides, etc. These molecules may be useful in therapies aimed at inhibiting ELAM1-mediated cell adhesion. To identify such molecules, one produces a test mixture by contacting together an inhibitor candidate, a fucose acceptor and a 1,3-fucosyl transferase. The fucose acceptor is, preferably, LacNAc or 2'-fucosyllectose. The 1,3-fucosyl transferase preferably is derived from an extract from a cell transformed with clone 7.2 or clone 1. Then one assays the test mixture for 1,3-fucosyl transfersee activity, such as described in Example XII.

The existence of antibodies against ELAM1, VCAM1 and 1b, CDX and VLA4 makes possible another method for isolating other ELAMs and ELAM ligands. The method takes advantage of an antibody characteristic known as idiotypy. Each antibody contains a unique region that is specific for an antigen. This region is called the igiotype. Antibodies, themselves, contain antigenic determinants; the idiotype of an antibody is an antigenic determinant unique to that molecule. By immunizing an organism with antibodies, one can raise "anti-antibodies" that recognize them, including antibodies that recognize the idiotype. Antibodies that recognize the idiotype of another antibody are called anti-idiotypic antibodies. Some anti-idiotypic antibodies mimic the shape of the original antigen that the antibody recognizes and are said to bear the "internal image" of the antigen. (Kennedy, 1986.) When the antigen is a ligand, certain anti-idiotypes can bind to that ligand is receptor. Investigators have identified several of these, including anti-idiotypes that bind to receptors for insulin, angiotensin II, adenosine I, β-adrenalin, and rat brain nicotine and opiate receptors. (Carlsson and Glad, 1989.)

Taking advantage of this phenomenon, other ELAMs and ELAM ligands may be isolated using anti-idiotypic antibodies. Anti-idiotypes may be used to screen for molecules binding to the original antigen. For example, one may use this technique to identify other ELAM ligands.

We have demonstrated that related ELAMs exist with similar domain structures (i.e., VCAM1 and VCAM1b.) As a result of gene shuffling, there may be several adhesion molecules on the cell surface that share one or more domains. Anti-idiotypic antibodies, which recognize any shared domains, are useful to isolate immunochemically ELAMs or ELAM-ligands not identified by bioassay, which relies on the protein's function, rather than structure.

In order that one may better understand this invention, we set forth the following examples. These examples are for purposes of illustration and are not to be construed as limiting the scope of the invention in any manner.

EXAMPLE I

PREPARATION OF A cDNA SUBLIBRARY ENRICHED FOR ELAM SEQUENCES

We prepared a cDNA sublibrary enriched for ELAN sequences as follows:

We isolated human umbilical vein endothelial cells (HUVECs) from umbilical cords, grew the cells in primary culture, and serially passaged them as described in Gimbrone (1976). We used HUVECs for library construction at passages 4 or 5. To induce the cells to produce mRNA for ELAMs we incubated confluent monolayers for 2.5 hours at 37° C. with recombinant human IL-1β (10 units/ml). We isolated the mRNA from these cells and reverse-transcribed it into cDNA using techniques well known to the art. (Gubler and Hoffman, 1983.) Using standard procedures, we ligated double stranded cDNA to a NotI-BstXI linker/adaptor having the following sequence:

GCGGCCGCTT TAGAGCACA 3' (SEQ ID NO:11)
CTCTAAAGCG GCCGC 3' (SEQ ID NO:12)

We then size-selected the cDNA on a 4.2 ml 5–20% potassium acetate gradient, 2 mM EDTA, 1 μg/ml ethidium bromide, in a Beckman® SW60 Rotor for 3 hours at 50,000 rpm at 22° C. according to the protocols of Brian Seed. (See also Maniatis, 1982, p. 278.) We pooled the cDNA fragments of greater than 500 base pairs. Then we repared the vector, pCDM8 (a gift from Brian Seed). We digested this plasmid with BstXI. To remove the 400 base pair stuffer fragment we centrifuged the mixture on a potassium acetate gradient, as above, and isolated the large fragment. We further purified this fragment by agarose gel electrophoresis, and then ligated the cDNA to the vector. In this way we created recombinant DNA molecules containing DNA sequences for mRNA expressed in induced HUVECs. We used these plasmids to transform *E. coli* MC1061 P3. The result was a collection of over $7 \times 10^6$ recombinant clones comprising a cDNA library for IL-1β-induced HUVEC mRNA.

In order to prepare from this cDNA library a sublibrary enriched for ELAM cDNA sequences, we first prepared a subtracted probe enriched for ELAM sequences. We prepared cDNA as above from HUVECs induced with IL-1β and labeled it with $^{32}$P. (Davis, 1986.) Then we isolated mRNA from HUVECs that had not been induced. To subtract uninduced cDNA sequences from induced sequences we hybridized the mRNA with the cDNA and isolated cDNA that had not hybridized to mRNA, as described by Davis (1986). We subjected the isolated cDNA to another round of subtraction to increase the level of enrichment. In all, we prepared three batches of subtracted probes enriched for ELAM sequences.

We tested the level of purification of the probe by Northern blot. (Lehrach et al., 1977.) We ran a gel with parallel lanes of polyA+ mRNA from induced and uninduced HUVECs and blotted it on Gene Screen® (New England Nuclear). Hybridization and subsequent autoradiography revealed that the probe bound strongly to a 4 kb band in the induced lane but did not bind, beyond background, to the uninduced lane. Occasionally we noted less intense hybridization bands to other messages in the induced lane.

We used the subtracted probe to create a cDNA sublibrary in *E. coli* MC1061 P3 enriched for IL-1β induced sequences. We began by plating-out one million clones of the IL-1β-induced HUVEC cDNA library. We plated one million colonies on Gene Screen Plush® filters (New England Nuclear) on LB agar containing 12.5 μg/ml ampicillin and 7.5 μg/ml tetracycline, and grew them at 37° C. for 12 hours. We made two replicate filters (lifts) from each master. We grew these on LB agar containing 12.5 μg/ml ampicillin and 7.5 μg/ml tetracycline for 4 hours and amplified them on LB agar containing 250 μg/ml chloramphenicol for 16 hours. We lysed the filters according to manufacturer's protocol and then prehybridized them in Plaque Screen® Buffer (0.05M TRIS-HCl pH7.5, 1M NaCl, 1% SDS, 0.1% sodium pyrophosphate, 0.2% polyvinylpyrrolidone (PVP), 0.2% Ficoll-400, 0.2% BSA). We hybridized the filters at 65° C. for 40 hours in 50 ml Plaque Screen® Buffer containing 10% dextran sulfate and 100 μg/ml yeast tRNA and approximately $1 \times 10^7$ cpm of the subtracted IL-1β-HUVEC cDNA. We then washed the filters twice with Plaque Screen® Buffer, twice with 2×SSC, 1% SDS, and twice with 1×SSC, 1% SDS at 65° C. We then exposed the filters to film for 5 days.

We selected colonies that hybridized to the probe by aligning the master filters with the autoradiographs and scraping the colonies off the filters with sterile toothpicks. We placed each scraping in one well of a 96-well microtiter plate filled with LB broth containing 7.5 μg/ml tetracycline and 12.5 μg/ml ampicillin. After inoculation, we incubated the microtiter plates overnight at 37° C. When the cells had grown we added glycerol to each well to a final concentration of 20% and stored the plates at −70° C. In this way we isolated from the master library filters 864 colonies comprising the cDNA sublibrary enriched for ELAM sequences. We point out that because of the plating density, not all the colonies of the enriched sublibrary were pure.

We carried out two sets of procedures in parallel with the enriched cDNA sublibrary.

EXAMPLE II

ISOLATION OF A CLONE EXPRESSING ELAM1

In a first procedure we isolated from the enriched sublibrary a clone expressing ELAM1. We chose to transfect this sublibrary into a cell line competent for high-level transient expression, the African Green Monkey kidney cell line, COS 7. We plated the cells and transfected the sublibrary by spheroplast fusion. (Sandri-Goldin et al., 1981.) Forty-eight hours after transfection, we assayed the COS 7 cells for expression of ELAM1 by their ability to bind HL-60 cells, a cell line known to bind to endothelial cells stimulated with inflammatory agents.

We performed the assay as follows: We labeled HL-60 cells with carboxyfluorescein diacetate according to the Brenan and Parish method. (Brenan and Parish, 1984.) Briefly, we resuspended HL-60 cells in RPMI/10% FCS at a concentration of $1 \times 10^7$ cells/ml, and added carboxyfluorescein diacetate to a final concentration of 0.1 mg/ml from a stock solution of 10 mg/ml in acetone. We incubated COS 7 cells with labeled HL-60 cells for minutes at room temperature. We washed the cells 3–4 times with RPMI/1% FCS. We examined the petri dish by fluorescence microscopy for clusters of adherent HL-60 cells. We picked regions of the cell plates with clusters of HL-60 cells and lysed the cells in 0.6% SDS, 10 mM EDTA, pH 8, then rescued the plasmids according to the method of Hirt, (Hirt, 1967.) We used these pooled plasmids to transform *E. coli* MC1061 P3. We grew colonies from these transformants and performed a second round of spheroplast fusion with COS 7 cells with subsequent assay for HL-60 adhesion. From among the cells that were positive for adhesion we selected one and isolated the plasmid from it. We designated a culture containing this plasmid ELAM CDM8 clone 6. We deposited this plasmid under the Budapest Treaty with In Vitro International, Inc., 611 P. Hammonds Ferry Rd., Linthicum, Md., 21090 (USA) on Apr. 20, 1989. It is identified as:

ELAM pCDM8 clone 6/*E. coli* MC1061 P3 Accession Number IVI-10204

EXAMPLE III

ISOLATION OF cDNA INSERTS FOR ELAM1 SEQUENCES

In a second procedure, we isolated cDNA inserts for IL-1β-induced cDNA sequences. We selected at random twenty-four of the 864 colonies of the enriched library and isolated plasmids from them using the alkaline miniprep procedure of Maniatis. (Maniatis, 1982.) We digested the plasmid DNA with XhoI or NotI and separated the fragments on 1% agarose gels. We identified from this gal two plasmids with inserts of greater than 3 kb, isolated these inserts and labeled them with $^{32}$P. (See, Feinberg and Vogelstein, 1983 and 1984.)

We then performed Northern blots with these inserts, as described above. Both inserts hybridized to bands at 4 kb in the induced HUVEC mRNA lane but did not hybridize to the uninduced HUVEC mRNA lane. The inserts cross-hybridized with the ELAM1 expressing plasmid ELAM pCDM8 clone 6 (described above) as well. We subcloned these inserts into NotI-digested pNN11 that had been treated with calf intestinal alkaline phosphatase. We constructed the sequencing plasmid pNN11 by removing the synthetic polylinker from the commercially available plasmid PUC8 (Pharmacia PL Biochemicals) by restriction digestion and replacing it with a new synthetic segment. The 2.5 kb backbone common to the pUC plasmids, that provides an origin of replication and confers ampicillin resistance, remained unchanged. The novel synthetic portion of pNN11 is shown in (SEQ ID NO:2). We called these new constructs pSQ148 and pSQ149, respectively.

EXAMPLE IV

A DNA SEQUENCE FOR ELAM1

We determined the entire DNA sequence for the inserts of plasmids pSQ148 and pSQ149 and 624 nucleotides of the sequence at the 5' end of the insert of EAM pCDM8 clone 6. We used the Maxam-Gilbert method. (Maxam and Gilbert, 1980.) Because the sequences have significant overlap, we obtained a composite sequence of ELAM cDNA, a sequence of 3863 nucleotides. This sequence consists of 140 nucleotides of the 5' untranslated region, 1830 nucleotides encoding 610 amino acids, and 1893 nucleotides of the 3' untranslated region (including a translational stop codon and a polyadenylation signal). The mature protein derived from the deduced amino acid sequence has been designated ELAM1, and the coding sequence has been designated the ELAM1 DNA sequence. The cDNA sequence of ELAM1 is shown in FIG. 1 (SEQ ID NO:1).

A search of the Genbank Data Base, release 58, December 1988, revealed that the DNA sequence for ELAM1 has no significant homologies to known DNA sequences.

We used this cDNA sequence to deduce the ELAM1 amino acid sequence, that is also presented in FIG. 1 (SEQ ID NO:1). Our analysis of the sequence revealed the following properties: The protein possesses a hydrophobic N-terminal sequence characteristic of a signal sequence.

(von Heijne, 1986.) We have not yet determined the signal cleavage site and the mature N-terminus through protein sequencing, however based on von Heijna we predict that the mature N-terminal amino acid will be tryptophan, at nucleotide number 204 in FIG. 1 (SEQ ID NO:1). The extracellular domain of the polypeptide is approximately 554 amino acids including the signal sequence and is followed by a hydrophobic transmembrane region of 24 amino acids. The protein possesses a short, charged cytoplasmic tail of 32 amino acids. We note that the protein is cysteine-rich and contains eleven potential N-glycosylation sites.

When we compared the amino acid sequence of ELAM1 to other proteins in the NBRF and NEW protein data bases we found significant homology with several proteins, including complement C2 precursor, β-2-glycoprotein I, C4b-binding protein, complement factor B, complement factor H, Drosophila notch protein, the IgE receptor Hepatic lectin, and Coagulation factors IX and X precursors. Thus, we can divide ELAM1 into at least three domains based on homology to the above-mentioned proteins: (1) a lectin-like domain (nucleotides 204–563 of FIG. 1 (SEQ ID NO:1)); (2) an EGF-like domain (nucleotides 564–668); and (3) a consensus cysteine repeat unit of 59–63 amino acids containing six cysteine residues per repeat (nucleotides 669—1793). Other invariable amino acids in each repeat are proline, glycine, and tryptophan.

EXAMPLE V

MONOCLONAL ANTIBODIES RECOGNIZING ELAM1

To make monoclonal antibodies that recognize ELAM1 we prepared hybridomas in essentially the same manner as we did in Example X, infra. However, we immunized the mice with ELAM1-expressing COS cells and identified mice producing anti-ELAM1 antibodies by testing their antiserum for the ability to block HL-60 cell adhesion to IL-1β induced HUVECs.

We screened hybridomas produced in this manner for those producing anti-ELAM1 monoclonals using several assays. First, we tested the culture supernatants for antibodies having the ability to bind to a cell line that stably expressed ELAM1. This cell line was a line of CHO-DHFR⁻ cells transfected with the ELAM1 animal cell expression vector, pBG341jod.ELAM. We created this plasmid by introducing the DNA sequence encoding ELAM1 from pCDM8 clone 6 into the NotI site of pBG341.jod (described in Example VIII, infra). The ELAM1 expressing CHO-DHFR⁻ derived cell line was detected using an adhesion assay to HL-60 cells.

Second, we screened hybridoma culture supernatants for the ability to bind cytokine-induced, but not control, HUVECs.

Third, we tested them for their ability to inhibit HL-60 cell adhesion to cytokin-induced HUVEC monolayers.

We identified one hybridoma clone, BB11, which produced a positive result in all three assays. BB11 immunoprecipitates proteins with molecular weights of about 110 kD and 96 kD from ELAM1-expressing HUVECs and COS cells, representing variably glycosylated forms of ELAM1. (Bevilacqua et al., 1989.) It also completely blocked adhesion of HL-60 cells to ELAM1-expressing COS and CHO cells. It produced immunoglobulins of the $IgG_{2b}$ class. We deposited a subclone of this hybridoma under the Budapest Treaty with In Vitro International, Inc., 611 P. Hammonds Ferry Rd., Linthicum, Md. 21090 (USA) on Dec. 13, 1989. It is identified as:

Monoclonal antibody CDB.BB11.BC6 Accession Number IVI-10220.

EXAMPLE VI

ISOLATION OF CLONES EXPRESSING VCAM1 and VCAM1b

We have also characterized and cloned two different ELAMs that bind to lymphocytes and lymphocyte-like cell lines. As a first step, we characterized the binding pathways of RAMOS, a B-lymphocyte-like line, and JURKAT, a T-lymphocyte-like line, to HUVECs induced with IL-1β or TNF for 4, 24, or 48 hours. We found that both RAMOS and JURKAT binding was maximal at 4 hours after induction with either IL-1β or TNF, and binding was maintained at 24 hours and 48 hours after induction. RAMOS binding was temperature-sensitive, occurring at room temperature but not at 4° C. JURKAT binding was reduced but not completely eliminated at 4° C., and thus JURKAT exhibited both a temperature-sensitive and temperature-insensitive component. Antisera from mice immunized with JURKAT cells inhibited binding from both JURKAT and RAMOS cells to HUVECs, inaicating that RAMOS and JURKAT share a MILA. Neither RAMOS nor JURKAT bound to COS or CHO cells expressing ELAM1, indicating the presence of at least one other inducible ELAM on HUVECs, at 4 to 48 hours after induction.

In order to isolate clones expressing the ELAMs involved in RAMOS and JURKAT binding to HUVECs, We screened the previously described ELAM-enriched HUVEC cDNA sublibrary by the method described in Example II, supra. We incubated carboxy-fluorescein diacetate-labeled RAMOS and JURKAT cells with sublibrary-transfected COS 7 cells. Regions of the cell plates with clusters of bouna cells were picked and lysed, and the plasmids were rescued, transformed into E. coli, and reassayed in COS 7 cells as previously described. Plasmids were isolated from individual bacteria colonies from the transformants that were positive on reassay. These plasmids were transfected individually into COS 7 cells, and a plasmid that tested positive for adhesion to RAMOS and JURKAT was identified. The cDNA insert from this plasmid was excised, radioactively labeled, and used to probe a Northern blot according to the procedures of Lehrach (1979). The probe hybridized to an RNA species approximately 3.4 kb in length. The RNA was undetectable in uninduced HUVEC RNA, barely detectable at 5, 10, 30 or 60 minutes after treatment with IL-1β, but abundant at 2, 24, 48 and 72 hours after treatment with IL-1β.

We designated the plasmid AM pCDM8 clone 41. We deposited this plasmid under the Budapest Treaty with In Vitro International, Inc., Linthicum, Md. (USA) on May 24, 1989. It is identified as:

AM pCDM 8 clone 41/E. coli MC1061 P3 Accession Number IVI-10206

We have also isolated a cDNA for another VCAM. We screened the IL-1β-induced HUVEC cDNA library (Example I) with a labeled VCAM1-encoding insert from AM pCDM 8 clone 41. We sequenced one of these, clone 1E11. We found several clones that were longer than the clone 41 insert as analyzed by rectriction mapping with XbaI. We sequenced one of these; clone 1E11. We deposited it under the Budapest Treaty with In Vitro International, Inc., Linthicum, Md. (USA) on Dec. 7, 1989. It is identified as:

VCAM 1B Clone 1E11 pCDM8/*E. coli* MC1061p3 Accession Number IVI-10216.

We are also isolating DNA sequences for other ELAMs. We are collecting mRNA from HUVECs around forty-eight hours after IL-1β induction. We will isolate the ELAM cDNA sequences in a manner similar to the one we used to isolate the cDNA sequences for ELAM1 and VCAM1 and 1b.

Alternatively, one may identify other ELAMs by inducing cells with other inflammatory agents, such as TNF, LT, LPS, interferons, or combinations of such agents.

EXAMPLE VII

DNA SEQUENCES FOR VCAM1 and VCAM1b

We determined the entire DNA sequence for the insert of plasmid AM pCDM8 clone 41 by the method of Maxam and Gilbert (1980). This sequence consists of 106 nucleotides of the 5' untranslated region, 1941 nucleotides encoding 647 amino acids, and 764 nucleotides of the 3' untranslated region including a translational stop codon. The protein derived from the cDNA sequence has been designated VCAM1, and the coding sequence has been designated the VCAM1 DNA sequence. We have presented the cDNA sequence of VCAM1 in FIGS. 2A–D (SEQ ID NO:3). The putative amino acid sequence of VCAM1 is also indicated in FIGS. 2A–D (SEQ ID NO:3).

We also determined the entire DNA sequence for the insert of plasmid VCAM1b pCDM8 1E11 by the method of Maxam and Gilbert (1980). This sequence consists of 99 nucleotides of the 5' untranslated region, 2217 nucleotides encoding 739 amino acids and 764 nucleotides of the 3' untranslated region including a translational stop codon. We have designated the mature protein derived from the cDNA sequence as VCAM1b and the coding sequence as the VCAM1b DNA sequence. We have presented the cDNA sequence and putative amino acid sequence of VCAM1b in FIGS. 3A–D (SEQ ID NO:4).

Comparison of the DNA and amino acid sequences of VCAM1 and VCAM1b revealed that they are virtually identical except for one significant differene: VCAM1b contains an insertion of 276 nucleotides near the middle of the coding region. These nucleotides encode 92 additional amino acids which form an extra domain of 84 amino acids situated between the end of VCAM1 domain 3 and the beginning of VCAM1 domain 4. We discuss the significance of this domain, designated VCAM1 domain 3B, below.

Our analysis of the sequences revealed the following properties: The VCAM1 polypeptida possesses a hydrophobic N-terminal sequence characteristic of a signal sequence. (von Heijne, 1986.) We have not yet determined the signal cleavage site and the mature N-terminus through protein sequencing, however based on von Heijne we predict that the N-terminal amino acid of the mature protein will be phenylalanine, at nucleotide number 179 in FIG. 2A (SEQ ID NO:3). The extracellular domain of the polypeptide is approximately 606 amino acids including the signal sequence and is followed by a hydrophobic transmembrane region of 22 amino acids. The protein possesses a short, charged cytoplasmic tail of 19 amino acids. We note that the protein contains six potential N-glycosylation sites.

Similarly, the N-termindl amino acid of the mature VCAM1b protein should be the phenylalanine, at nucleotide number 172 of FIG. 3A (SEQ ID NO:4). The extracellular domain of the polypeptide, which is longer than VCAM1, is approximately 698 amino acids including the signal sequence and is followed-by a hydrophobic transmembrane region of 22 amino acids. The protein possesses a short, charged cytoplasmic tail of 19 amino acids. We note that the protein contains seven potential N-glycosylation sites.

Comparison of the amino acid sequences of VCAM1 and VCAM1b with other proteins in the NBRF and NEW protein databases revealed significant homologies with several proteins, including non-specific cross-reactive antigen (NCA), biliary glycoprotein 1 (BG1), neural cell adhesion molecule (NCAM), carcinoembryonic antigen (CEA), immunoglobulin alpha chain constant region, the T cell receptor (TCR) alpha and beta chain variable regions, and myelin associated glycoprotein (MAG). Lesser homology is seen with myosin light chain kinase, ribulose biphosphate carboxylase, adenovirus E1A 28K protein, pseudouridine synthetase, and xylulokinase. VCAM1 and 1b and the VCAM1 and 1b DNA sequences show no homology with, and are distinct from, the previously described ELAM1 (supra).

Importantly, NCA, BG1, NCAM, CEA, MAG, and TCR are members of the immunoglobulin gene superfamily. (Williams and Barclay, 1988; Hunkapiller and Hood, 1989.) Members of this family are defined by the presence of one or more regions homologous to the basic structural unit of immunoglobulin (Ig) molecules, the Ig homology unit. (Hunkapiller and Hood, 1989.) These units are characterized by a primary amino acid sequence of about 70–110 residues in length, with an essentially invariant disulfide bridge spanning 50–70 residues, and several other relatively conserved residues involved in establishing a tertiary structure referred to as the "antibody fold". These units may be further subdivided into three groups, i.e., V, C1, And C2 (Williams and Barclay, 1988), or V, C, and H (Hunkapiller and Hood, 1989), based on various criteria, including intercysteine spacing, number of beta strands, and type of conserved residues. When these criteria are applied to the predicted primary sequence of VCAM1, the sequence can be divided into six Ig units, designated domains 1–6, all of which fall into the C2 or H subset, each of about 100 amino acids in length. The invariant disulfide bridges of the six domains, referring to FIGS. 2A–D (SEQ ID NO:3), occur between cysteines 47 and 95 (domain 1), 137 and 195 (domain 2), 246 and 291 (domain 3), 333 and 391 (domain 4), 442 and 487 (domain 5), and 531 and 576 (domain 6).

As we stated above, VCAM1b has seven domains. We have designated the additional domain as domain 3B. This domain in included in the additional 276 nucleotides of VCAM1b that begin at nucleotide 1027 and end at nucleotide 1305 of FIG. 4 (SEQ ID NO:4). The DNA sequence encompassing domains 1–3 is 72% homologous to the DNA sequence encompassing domains 3B-5. At the polypeptide level, there is significant homology between domains 1 and 3B, 2 and 4, and 3 and 5, respectively. We present the domain structures of VCAM1 and VCAM1b in FIGS. 4 and 5 (SEQ ID NO:6).

Messenger RNAs for VCAM1 and VCAM1b could arise by two mechanisms: They could represent alternately spliced forms of the same gene product, or they could be the products of separate VCAM alleles. To help distinguish between these possibilities, we examined VCAM1 and mRNA from three individuals, at different time-points after cytokine induction. HUVECs were prepared from umbilical cords from three different individuals, the cord samples being labeled #1, #2 and #3. Each preparation was split into four separate flasks for treatment with TNF for 0 (untreated), 2.5, 24, and 48 hours. Relative amounts of VCAM1 and VCAM1b mRNA were determined by Northern blotting and probing with synthetic oligonucleotides specific for each form. VCAM1b was clearly the major mRNA present in all three umbilical cord preparations. VCAM1 was present in cords #1 and #3, most prominently at the 2.5 hour induction time-point, although in cord #3 VCAM1 was also present at 24 and 48 hours. Cord #2 cells had little or no VCAM1 mRNA, although amounts of VCAM1b mRNA were comparable to those in HUVECs from cords #1 and #3. The mechanism by which these two products arise is still unclear, although alternate splicing seems likely because the two mRNAs are identical except for the deletion of one domain, at a point likely to be a splice junction, judging by its position between domains (Hunkapiller and Hood, 1989) and by the presence of the dinuclaotide AG, typical of splice junctions (Breathnach and Chambon, 1981). Furthermore, alternate splicing is common among other members of the Ig gene superfamily to which VCAM1 is most clearly related. (Hunkapiller and Hood, 1989.)

Functionally, differences between the two forms of VCAM1 appear to be minimal. Both forms, when expressed transiently in COS 7 cells, bound RAMOS cells, and this binding was completely inhibited by Moab 14B9, indicating that the same epitope is relevant to binding in each case. Furthermore, we have shown that this epitope is located within the first three domains, which are common to both forms (see Example VIII, supra).

EXAMPLE VIII

RECOMBINANT SOLUBLE ELAM1 AND VCAM1b

We constructed a vector expressing recombinant soluble ELAM1 (rsELAM1). We called this vector pSAB108. The rsELAM1 expressed by pSAB108 contains the portion of the extracellular domain of ELAM1 encoded by the DNA sequence of FIG. 1 (SEQ ID NO:1) from nucleotide 141 to nucleotide 1790.

To construct pSAB108 we first created a DNA fragment which encoded an rsELAM1. We digested ELAM pCDM8 clone 6 with MluI and NotI. This yielded a 3.8 kb DNA fragment including a DNA sequence encoding ELAM1. We subcloned this fragment into NotI-digested pNN11 that had been treated with calf intestinal alkaline phosphatase (described in Example III). We called this vector pNNELAM1.

We used site specific mutagenesis to eliminate the transmembrane and intracellular regions of ELAM1. (Peden and Nathans, 1982; Kalderon et al., 1982; Oostra et al., 1983.) Accordingly, we digested a sample of pNNELAM1 with EcoRI and isoldted the large fragment. We linearized another sample of pNNELAM1 with ScaI. Then we synthesized an oligonucleotide having the sequence 5' TGT-GAAGCTC CCTAAATTCC C (SEQ ID NO:13). When this sequence hybridizes to an ELAM1 antisense sequence it introduces a stop codon and a BamHI restriction site into the ELAM1 DNA sequence after nucleotide number 1790. We created a heteroduplex using these three fragments according to the methods of Morinaga et al. (1984) and Chang et al. (1984). We filled in the single stranded gaps with Klenow fragment and T4 ligase and used the mixture to transform *E. coli* MC1061. We screened the resulting colonies by checking for a BamHI site and selected mutagenized clones. Consequently on expression, the transmembrane region of the polypeptide is eliminated and the C-terminal amino acid is proline. We called this plasmid pSAB100.

Then we digested pSABb100 with AatII and NcoI and isolated the 5.2 kb fragment. We also digested pNNELAM1 with these two enzymes and isolated the 1.4 kb fragment. NcoI cuts at nucleotide 927 of FIG. 1 (SEQ ID NO:1), about the middle of the ELAM1 coding area. We ligated these two DNA fragments and called the plasmid pSAB108. We made this construction because site-directed mutagenesis sometimes causes mutations in other parts of the molecule and we wanted to avoid any such mutations in the coding region of rsELAM1. We digested pSAB108 with NotI and isolated the 3.8 kb fragment. We ligated this fragment to a 7819 bp fragment of pBG341.jod, created as follows.

First we obtained pSV2-DHFR, ATCC 37146, from the American Type Culture Collection, Bethesda, Md. (USA). (Subramani et al., 1981.) We digested this with ApaI and EcoRI and isolated the 4420 bp fragment. Then, we produced a synthetic double stranded DNA sequence having an ApaI overhang, a DNA sequence encoding nucleotides +190 to +233 of the human gastrin gene (Sato et al., 1986, FIG. 4), an XhoI site, and an EcoRI overhang. We ligated this oligonucleotide with the 4420 bp fragment of pSV2-DHFR and called the resulting plasmid pDT4. We digested this plasmid with AatII and XhoI and isolated the 4391 bp fragment.

Then we cleaved the Mullerian Inhibiting Substance expression vector pD1 (Cate et al., 1986) with AatII and SalI and isolated the 5462 bp fragment. We ligated this fragment with the 4391 bp fragment of pDT4 to make pJOD-10.

We digested pJOD-10 with HindIII and BstEII and isolated the large fragment which did not encode Mullerian Inhibiting Substance. We blunt-ended the fragment ends, ligated SalI linkers to the ends and self-ligated the vector. This produced pJOD-s.

Then we digested pJOD-s with AatI and NotI and isolated the 6750 bp fragment. We ligated this to a 1100 bp NotI fragment from pBG341, which we created as follows.

We created pBG341 by replacing the SmaI site of pBG312 (Cate et al., 1986) with a NotI site. We linearized pBG312 with BglII, blunt-ended the fragment by filling in with Klenow, and self-ligated it. We linearized this plasmid with BamHI and again blunt-ended and self-ligated it. We linearized this plasmid with SmaI and ligated to the ends a NotI linker having the sequence 5' GCGGCGC. We called the resulting plasmid pBG341.

We digested pBG341 with AatII and NotI and isolated the 1100 bp fragment. We ligated this fragment to a 6750 bp fragment of pJOD-s. We called the resulting plasmid pBG341.jod. This plasmid contains the SV40 early and the adenovirus major late promoter. Genes inserted into the plasmid at the NotI site are transcribed from either of these promoters.

Then we linearized pBG341.jod with NotI and isolated the linear 7819 bp fragment. We ligated this fragment with the 3.8 kb fragment of pSAB108, which encoded rsELAM1, generating plasmid pSAB110.

We transfected CHO-DHFR$^-$ cells by electroporation with plasmid pSAB110 linearized with AatII. We performed electroporation with a Biorad® Gene Pulser at 270V and 960 $\mu$FD using $10^7$ cells/ml in 20 mM HEPES pH 7.05, 137 mM NaCl, 5 mM KCl, 0.7 mM $Na_2HPO_4$, and 6 mM dextrose with 20 $\mu$g plasmid and 200 $\mu$g sonicated salmon sperm DNA. Following transfection we cultured the cells in selective medium, alpha$^-$ MEM containing 500 nM methotrexate and 10% dialyzed FCS. We picked colonies, plated them onto 96-well cluster plates and detected rsELAM1-expressing cells using the monoclonal antibody BB11. After growing cells to confluence in complete medium containing 10% fetal calf serum (FCS) we maintained them in medium containing 2% FCS in which the cells produced rsELAM1. We harvested medium and replaced it with fresh 2% serum every three or four days.

We isolated rsELAM1 from this conditioned medium to at least 95% purity. This involved concentrating the medium and incubating it overnight with Moab BB11(Example V) covalently coupled to protein A sepharose. (Schneider et al., 1982.) Then we washed this resin with PBS to remove unbound protein, eluted bound material with 0.1 M glycine, pH 2.7, neutralized the aluate with sodium phosphate and dialyzed it against PBS. We further purified the rsELAM1 by chromatography with Protein A sepharose in PBS.

Using the following assay, we demonstrated that we had produced rsELAM1. To a 6 cm diameter Petri dish of bacteriologic plastic (e.g., Falcon #1007®) we added 2.5 ml of 50 mM Tris buffer, pH 9.5. To this we added 10 $\mu$g of pure rsELAM1. We incubated the plate for 60 minutes at room temperature to allow the rsELAM1 to bind to the plate. Then we aspirated the medium and replaced it with PBS containing 10 mg/ml bovine serum albumin. We incubated the plates overnight at 4° in this solution to block remaining protein binding sites on the plates. We warmed the plates to room temperature, washed them with medium containing 10% fetal calf serum, and incubated them with 2 ml of cells ($2 \times 10^6$ ml$^{-1}$) for 20 minutes. We aspirated the medium and washed the plates twice with 3 ml each of medium (RPMI 1640 with 10% serum). Then we examined the plates by microscopy.

We found that cells which bind ELAM1, such as HL-60 cells, bind to rsELAM1-coated plates, while cells which do not bind to ELAM1, e.g., the B cell line RAMOS, do not bind to these plates.

In addition, we found that the specific Moab BB11 blocks the binding of HL-60 cells to rsELAM1coated plates. Together, these results show first, that we have produced rsELAM1, and, second, that like ELAM1, rsELAM1 possesses the ability to bind to leukocytes.

We also constructed a vector expressing recombinant soluble VCAM1b (rsVCAM1b). This vector was named pBN1006, and the rsVCAM1b expressed by pBN1006 contains the portion of the extracellular domain of VCAM1b encoded by the DNA sequence shown in FIGS. 3A–D (SEQ ID NO:4) from nucleotide 107 to nucleotide 2193.

In order to generate a cell line capable of constitutively expressing full length soluble VCAM1b, we first created a vector derived from pJOD-s having a unique NotI site downstream from the adenovirus major late promoter, so that NotI fragments could be inserted into the expression vector. pJOD-s was linearized by NotI cleavage of the plasmid DNA. The protruding 5' termini were blunt-ended using Mung bean nuclease and the linearized DNA fragment was purified by low melting temperature agarose (LMA) gel electrophoresis. The DNA fragment was religated using T4 DNA ligase. The ligated molecules were then transformed into E. coli JA221 (ATCC accession no. 33875). Colonies were screened for the absence of a NotI site. The resulting vector was designated as pJOD-s delta Not1. pJOD-s delta Not1 was linearized using saI and the 5' termini were dephosphorylated using calf intestine alkaline phosphatase. The linearized DNA fragment was purified by LMA gel electrophoresis and ligated in the presence of phosphorylated oligonucleotide ACE 175 (5' pTCGACGCGGC CGCG) (SEQ ID NO:14). The ligation mixture was transformed into E. coli JA221 and colonies were screened for the presence of a NotI site. The correct plasmid was named pMDR901.

Soluble VCAM1b was obtained by truncating VCAM1b clone 1E11 at nucleotide 2193 by digestion with AluI, thus eliminating the transmembrane and intracellular portion as well as the 3' untranslated region. A stop codon-NotI linker was added, and the insert was religated into pCDM8. The insert was excised from pCDM8 with NotI and ligated into pMDR901 at the NotI site. This construct, designated pBN1006t encodes full length soluble VCAM1b, having amino acids 1–698 as ghown in FIGS. 3A–D (SEQ ID NO:4).

Using materials and methods already described, we have also constructed plasmids expressing truncated forms of the rsELAM1 and rsVCAM1b molecules described above. These truncated forms, comprising the amino acid sequences of one or more of the particular domains of the axtracellular regions of ELAM1 and VCAM1b, were used to investigate which domain or domains are involved most directly in cell-to-cell adhesion. Our initial experiments have investigated the domains of ELAM1 and VCAM1 and 1b that are recognized by antibodies against those molecules, i.e., antibodies BB11 and 4B9, respectively.

A soluble ELAM1 construct designated CH101 was prepared comprising the lectin-like domain of ELAM1. Referring to FIG. 1 (SEQ ID NO:1), CH101 was the expression product of a cDNA sequence including nucleotides 1–557 (coding for amino acids 1 through 139 of ELAM1) and a stop codon. Another soluble construct designated CH102 was prepared comprising the lectin-like domain and the EGF-like domain of ELAM1. Referring to FIG. 1 (SEQ ID NO:1), CH102 was the expression product of a cDNA sequence that included nucleotides 1–671 (coding for amino acids 1 through 177 of ELAM1) and a stop codon. The soluble ELAM1 construct CH102 was found to immunoprecipitate the anti-ELAM1 monoclonal antibody, BB11.

The following soluble VCAM1 and 1b constructs were similarly prepared:

(A) domain 1 (nucleotides 1–430 of FIG. 2A (SEQ ID NO:3), coding for amino acids 1–108);

(B) domain 1+domain 2 (nucleotides 1–757 of FIG. 2A (SEQ ID NO:3), coding for amino acids 1–217);

(C) domain 1+domain 2+domain 3 (nucleotides 1–1036 of FIGS. 2A and 2B (SEQ ID NO:3), coding for amino acids 1–310);

(D) domain 1+domain 2+domain 3 (from a hybrid of VCAM1 and VCAM1b cDNA, coding for amino acids 1–317 as depicted in FIG. 3A (SEQ ID NO:4));

(E) full length soluble VCAM1 (nucleotides 1–1924 of FIG. 2A–C (SEQ ID NO:3), coding form amino tides 1–606); and (F) full length soluble VCAM1b (nucleotides 1–2193 of FIGS. 3A–C (SEQ ID NO:4), coding for amino tides 1–698).

Of the foregoing VCAM1 constructs, B, C, D, E and F (but not A) were immunoprecipitated with the anti-VCAM1 antibody 4B9. Constructs B, D, E and F were also found to produce protein functional for cell adhesion. Conditioned media containing protein encoded by constructs B, D, E and F were concentrated, passed over an immunoaffinity column of immobilized 4B9 antibody, and the bound protein eluted and neutralized as described for rsELAM1. The eluted proteins were immobilized on plastic as described for rsELAM1 and found to support specific adhesion of RAMOS and JURKAT cells. These results indicate that the first two domains of VCAM1 are sufficient to support adhesion of certain VLA4-expressing human lymphoid cell lines.

EXAMPLE IX

ISOLATION OF THE ELAM1 AND VCAM1 PROMOTER

We have isolated and characterized genomic clones for the ELAM1 and VCAM1 genes. We isolated the ELAM1 clones as follows:

We selected as probes either the entire ELAM pCDM8 clone 6 insert or a 400 base pair fragment from its 5' end. We labeled these molecules with $^{32}$P by random priming. Then we screened a human genomic EMBL3 library with the ELAM cDNA probes. We isolated and characterized a genomic ELAM1 clone from the library and designated it EL1-07. It includes approximately 15 kb of 5' flanking sequence including the transcriptional promoter for ELAM1 and approximately 100 base pairs of coding sequences at the 5' end of the gene. Current knowledge suggests that the relevant control sequences for induction will be included within the DNA sequence represented by this phage clone. (Leonardo and Baltimore, 1989.) We sequenced a region including 840 bp of 5' flanking sequence and 720 bp of the 5' end of the ELAM1 gene, including the first two exons, the first intron and part of the second intron. We present this sequence in FIG. 7 (SEQ ID NO:7). The 5' flanking region displays a classical promoter structure including TATAAA and CAAT sequences. It also contains the sequence GGG-GATTTCC (SEQ ID NO:15) about 95 base pairs upstream from the presumed start of transcription. This sequence is an NF-κB binding sequence identical to that found in the human κ immunoglobulin (Ig) gene enhancer. NF-κB is an inducible DNA binding protein known or suspected to stimulate transcription of a number of genes relevant to inflammation and the immune response (such as the immunoglobulins, the interleukin-2 receptor, and β-interferon, among others). It can be activated by TNF, IL-1, and LPS, the same inducers known to stimulate production of ELAM1, VCAM1, and ICAM1. (Lenardo and Baltimore, 1989; Osborn et al., 1989.) We have demonstrated that NF-κB DNA binding activity is stimulated in endothelial cells by IL-1 and TNF, and we are currently engaged in defining minimal DNA sequences necessary for inducible transcription from the ELAM1 promoter, by transfection of promoter/reporter gene constructs into endothelial and other cell types.

We deposited clone EL1-07 under the Budapest Treaty with In Vitro International, Inc., Linthicum, Md. (USA) on Dec. 7, 1989. It is identified as:

EL1-07 Accession Number IVI-10218.

We also isolated an EMBL3 genomic clone representing the VCAM1 gene by probing the previously mentioned EMBL3 human genomic library with a $^{32}$P-labeled 30 base oligomer probe homologous to the 5' end of the VCAM1 cDNA. We designated this clone VC1-16 and deposited it under the Budapest Treaty with In Vitro International, Inc., Linthicum, Md. (USA) on Dec. 7, 1989. It is identified as:

VC1-16 Accession Number IVI-10217.

We sequenced a region including approximately 300 bp of 5' flanking sequence and 900 bp of the 5' end of the VCAM1 gene, including the first exon, the first intron, and part of the second exon. We present this sequence in SEQ ID NO:8. The 5' flanking region has a classical TATAAA sequence, and two NF-κB consensus sequences: AGGGATTTCC (SEQ ID NO:16) on the sense strand from about −63 to −54 from the start of transcription, and GGGGAAACCC on the reverse compliment strand from about −69 to −78. This sequence will be used for studies analogous to those proposed for the ELAM1 promoter sequence.

EXAMPLE X

ANTIBODIES RECOGNIZING CDX

We isolated CDX, a MILA involved in ELAM1-mediated adhesion. As a first step, we prepared monoclonal antibodies that recognized an antigen on the leukocyte cell surface and that interfered with leukocyte-endothelial cell binding. In order to assure that the antigen that these monoclonals recognized was involved in ELAM1-mediated adhesion, we tested the monoclonals in systems in which ELAM1-mediated binding was the exclusive cell-cell binding pathway.

1. Preparation and Analysis of Monoclonal Antibodies Against CDX a. Adhesion Assay To identify Moabs that inhibit leukocyte-endothelial cell binding, we devloped an improved assay to detect endothelial cell-leukocyte adhesion. We performed this assay using HL-60 cells and HUVECs. It should be clear that one can perform such an assay using any cell line that expresses a MILA and with any cell line that expresses an ELAM. In 48-well tissue-culture plates we grew HUVECs to confluence ($8\times10^4$ cells/well). We washed the cells once with RPMI/1% FCS and added 0.5 ml RPMI/1% FCS with 13 U/ml of IL-1β to each well (except the control wells). We incubated these cells for 4 hours at 37° C. Just before use, we washed them once with RPMI/1% FCS. The HL-60 cells we used in the assay had been labeled overnight with 1 μCi/ml of $^{35}$S-methionine. We washed these cells once and then resuspended them in RPMI/1% FCS at $5\times10^6$ cells/ml. We took 100 μl of the HL-60 cells and incubated them for 30 min at 0° C. with 50 μl of Moab (1 μg/ml). Then we added the 150 μl to each well of HUVECs. We allowed the cells to bind for 10 min at 20° C. and then washed the wells gently once with RPMI/1% FCS. We filled the wells with RPMI/ 1% FCS, sealed the plates, inverted them, and centrifuged them for 2 min at 500×g. We removed the media and washed the wells two more times with PBS⁻. (PBS⁻ is PBS without $Ca^{++}$ and without $Mg^{++}$.) We determined the number of HL-60 cells bound to the HUVECs by solubilizing the cells in each well with 200 μl of 0.2N NaOH/1% SDS, adding 4.5 ml of scintillant (Ready Protein, Beckman), and counting with a scintillation counter.

b. Preparation of Hybridomas

To make monoclonal antibodies against CDX we prepared hybridomas in the following manner. We injected BALB C mice with whole, live HL-60 cells. Initially, each mouse received $2\times10^7$ cells in PBS⁻ intraperitoneally (IP). We injected complete Freund's adjuvant intraperitoneally at a different site 2–24 hours later. We boosted the mice with $2\times10^7$ cells IP every second week for six weeks. Four days before fusing we injected the mice intravenously with $5\times10^6$ cells and IP with $5\times10^6$ cells.

We tected immune serum from these animals for the ability to inhibit binding of the HL-60 cells to IL-1β stimulated HUVECs by the adhesion assay described above. The immune serum tested positive after the third boost and we proceeded to produce hybridomas from the spleen cells of the immunized animals. We performed fusion of spleen cells and myeloma cells in a manner standard to the art. (See, Goding, 1983.)

Using the adhesion assay we described above, we screened the hybridomas for those producing monoclonal antibodies that inhibited the binding of HL-60 cells to IL-1β-induced HUVECs. In this way we identified hybridomas that produced monoclonal antibodies that recognized CDX. We used five of these hybridomas to produce ascites fluid. We deposited one of them, designated $SGB_3B_4$, under the Budapest Treaty with In Vitro International, Inc., Linthicum, Md. (USA) on Apr. 25, 1989. It is identified as:

SGB$_3$B$_4$ Accession number: IVI-10205 c. FACS Analysis

To identify to which cell types our monoclonals bound, we performed FACS analysis. This involved taking 2×10$^5$ cells, washing them one time with PBS$^-$, and then blocking Fc receptors by incubation in 25 µl of RPMI, 1% FCS, 0.1 mg/mL human IgG, and 0.1% sodium azide for 10 min at 0° C. We then added antibody (25 µl at 1 µg/ml) and incubated the cells 30 min at 0° C. We centrifuged the cells at 250×g for 5 min, washed them two times wih Buffer A (PBS$^-$, 5% FCS, 0.1% azide) and resuspended them in 25 µl Buffer A containing 0.1 mg/ml human IgG. We added fluorescein-conjugated anti-mouse IgG (25 µl at 5 µg/ml in Buffer A (Cappel)) and incubated the mixture 30 min at 0° C. We centrifuged the cells, washed them once with Buffer A, and resuspended them in 250 µl Buffer A. Then we analyzed them on a Becton-Dickinson FACStar Cell Sorter.

We performed cell binding studies with the ELAM1-expressing COS cells essentially as described for the HL-60 cell-HUVEC adhesion assay.

2. Demonstration that Hybridoma SGB$_3$B$_4$ Produced Monoclonal Antibodies that Recognize CDX We have developed several lines of evidence that demonstrate that monoclonals from hybridoma SGB$_3$B$_4$ specifically recognize a MILIA involved in ELAM1-mediated binding, specifically, CDX.

First, the α-CDX antibodies should inhibit binding of cells expressing CDX to ELAM1-expressing cells. Using the adhesion assay, we showed that these monoclonals do indeed inhibit the binding of HL-60 cells and PMNs to IL-1β-induced HUVECs and ELAM1-expressing COS 7 cells. In the presence of 60.3, a monoclonal antibody against the β$_2$ integrin chain, the only binding pathway for HL-60 cells and PMNs that is utilized in ELAM1-expressing COS 7 cells is ELAM1 itself. Therefore, antibody inhibition of cell-cell adhesion in this system must be through the ELAM1 pathway via CDX.

Second, α-CDX monoclonals should recognize those cells that bind to ELAM1-expressing cells in an adhesion assay, but should not recognize those cells that do not bind to ELAM1 in this assay. Using FACS analysis, we determined the binding pattern of our Moabs. These monoclonals bound to the following cell types: HL-60, U937, HT-29, THP-1, SW620, SW948, SW1417, monocytes, eosinophils, and PMNs. They did not bind to these cells: RAJI, DAUDI, RAMOS, HeLa, or JY. (We isolated the non-transformed cells by fractionating peripheral blood leukocytes.) This binding pattern precisely parallels the binding of these cells to ELAM1-expressing COS 7 cells and to rsELAM1-coated plates.

Third, α-CDX monoclonals should exhibit a different recognition pattern than monoclonals against other leukocyte cell-surface antigens, such as LFA-1, LFA-3, CD44, ICAM1 and CD4. In fact, no other monoclonal of which we are aware exhibits the same cell-recognition pattern as our antibodies.

Fourth, and most convincing, using these MoAbs we cloned a gene that can confer ELAM1 binding activity in cells that otherwise do not bind to ELAM1.

In sum, it is apparent that the monoclonals produced by hybridoma SGB$_3$B$_4$, and by other hybridomas we isolated, recognize CDX. Consequently, we used these monoclonals to isolate CDX itself.

EXAMPLE XI

ISOLATION OF CDX

1. Iodinatign of HL-60 Cell Surface Proteins

We washed 1×10$^7$ HL-60 cells three times with PBS$^-$, resuspended them in 0.5 ml PBS$^-$ and added them to a tube coated with 50 µg 1,3,4,6-tetrachloro-3α,6α-diphenylglycouril (Sigma Chemical Co.). To this we added 1 mCi of $^{125}$I. We incubated the imixture for 30 min at 0° C. We transferred labeled cells to a tube containing 10 ml of RPMI/10% FCS and centrifuged them at 1000×g for 5 min. Then we washed them first with another 10 ml of RPMI/10% FCS and second with 2 ml of PBS$^-$. (Alternatively, we have labeled the cells metabolically with $^{35}$S-methionine or $^{35}$S-cysteine.) We lysed the cells by addition of 1.0 ml PBS$^×$ containing 1% NP40, 2 mM PMSF, 1 mM EDTA, soybean Trypsin inhibitor (50 mg/ml), and Leupeptin (1 mM) (Sigma Chemical Co.). Then we incubated them for 30 min at 0° C. We centrifuged the lysate for 10 min at 10,000×g to remove particulate matter. We precleared the supernatant containing labeled solubilized membrane proteins with 10 µg of rabbit anti-mouse IgM (Jackson Immuno-Research Labs) and 50 µl of Protein A sepharose (Zymed, 2 mg Protein A/ml) for 2 hours at 0° C. We stored the lysate at 4° C.

2. Immunoprecipitation of CDX

We purified CDX away from the other labeled proteins using the Moabs to immunoprecipitate it. We performed the immunoprecipitation as follows:

We incubated precleared lysate (50–100 µl) with 10λ of ARX beads for 2 hours at 4° C. We washed the sepharose four times with 2 ml PBS$^-$ containing 0.75% NP40, 0.2% DOC, and 1 mM EDTA. Then we resuspended the ARX beads in non-reducing SDS sample buffers. We heated the sample for 10 min at 85° C. and removed the supernatant. To this we added β-ME to 5%, heated for 5 min, and separated the molecules on a 10% SDS polyacrylamide gel. We dried the gel and autoradiographed it.

CDX appeared on the autoradiograph as a single, diffuse band with molecular weight of approximately 150 kD.

EXAMPLE XII

ISOLATION AND CHARACTERIZATION OF CLONE 7.2 AND CLONE 1

We prepared two cDNA libraries in the pCDM8 vector from two types of CDX-expressing cells, HL-60 cells and U937 cells. We isolated the mRNA from these cells and reverse-transcribed it into cDNA using techniques well known to the art. (Gubler and Hoffman, 1983.) Using standard procedures, we ligated double stranded cDNA to a NotI-BstXI linker/adaptor having the following sequence:

5' GCGGCCGCTT TAGAGCACA 3' (SEQ ID NO:11)

CTCTAAAGCG GCCGC 3' (SEQ ID NO:12)

We then size-selected the cDNA on a 4.2 ml 5–20% potassium acetate gradient, 2 mM EDTA, 1 µg/ml ethidium bromide, in a BECKAN SW60 Rotor for 3 hours at 50,000 rpm at 22° C. according to the protocols of Brian Seed. (See also Maniatis, 1982, p. 278.) We pooled the cDNA fragments of greater than 500 base pairs. Then we prepared the vector, pCDM8 (a gift from Brian Seed). We digested this plasmid with BstXI. To remove the 400 base pair stuffer fragment we centrifuged the mixture on a potassium acetate gradient, as above, and isolated the large fragment. We further purified this fragment by agarose gel electrophoresis, and then ligated the cDNA to the vector.

We then prepared an enriched cDNA library by first creating a $^{32}$P-labeled cDNA probe from 1 microgram of HL-60 poly A+ mRNA, then subtracting non-CDX related cDNA sequences from the probe by hybridizing with 30 micrograms of poly A+ mRNA from HeLa cells, which do not express CDX. (See, Davis, 1986.) We used the subtracted probe to screen the pCDM8 cDNA library and thus created an enriched sublibrary from HL-60 cells in *E. coli* MC1061 P3. We grew about 2100 clones in twenty-two 96-well plates. A U937 enriched sublibrary was prepared in a similar manner, and 1400 clones were obtained.

We divided the colonies from our HL-60 enriched library into 22 pools for transfection of COS 7 cells by spheroplast fusion. (Sandri-Goldin et al. 1981.) We assayed transfected COS 7 cells for ELAM1-binding activity by panning with α-CDX monoclonal antibodies from hybridoma $SGC_2E_5$ (an antibody similar in function to $SGB_3B_4$) according to the method of Seed and Aruffo (1987). (See also Aruffo and Seed, 1987 and Wysocki and Sato, 1978). Pool #7 assayed positive, yielding two clones with a 2.1 kb cDNA insert. These were designated clones 7.1 and 7.2.

We obtained the DNA sequence of clone 7.2 by the Maxam and Gilbert technique (Maxim and Gilbert, 1980) from CDX pCDM8 clone 7.2 and from a portion of the 7.2 insert subcloned into the sequencing vector, pNN11. The latter plasmid was designated pSQ219. The DNA sequence obtained is set forth in (SEQ ID NO:9).

We deposited a culture containing the plasmid CDX pCDM8 clone 7.2 under the Budapest Treaty with In Vitro International, Inc., 611 P. Hammonds Ferry Rd., Linthicum, Md. 21090 (USA) on Apr. 26, 1990. The deposit is identified as:

CDX pCDM8/*E. coli* MC1061 P3 Accession Number IVI-10242

We also performed a Northern blot on mRNA from HL-60 cells and probed it with clone 7.2. Clone 7.2 hybridized to three mRNA species, two prominent bands at 6.0 kb and 2.4 kb and another band at 3.0 kb. Clone 7.2, a cDNA of 2.1 kb, is not large enough to be a full length cDNA from the 3.0 kb and 6.0 kb species. Therefore, in order to identify DNA sequences for these messages, we probed the enriched cDNA sublibrary from both U937 and HL-60 cells with an oligonucleotide derived from clone 7.2. We isolated several long inserts from the HL-60 library, transfected them into COS 7 cells, and selected clones that bound to ELAM1 and α-CDX. In this way we identified a 2.9 kb insert that could have come from the 3.0 kb message. We called it CDX clone 1.

We determined the DNA sequence of CDX clone 1 by the Maxam and Gilbert technique. The DNA sequence obtained is set forth in (SEQ ID NO:10).

We deposited a culture containing the plasmid CDX clone 1 under the Budapest Treaty with In Vitro International, Inc., 611 P. Hammonds Ferry Rd., Linthicum, Md. 21090 (USA) on Oct. 11, 1990. The deposit is identified as:

CDX clone 1 pCDM8/*E. coli* MC1061 P3 Accession Number IVI-10255.

We transfected clone 7.2 and clone 1 into COS 7 and CHO cells. At 48 hours after transfection these cells expressed a glycoprotein on their cell surfaces to which fluorescently labelled α-CDX antibodies bound, as assayed by FACS. These cell surface proteins could be labeled with $^{125}I$ and immunoprecipitated with α-CDX Moabs. We designated the protein isolated from COS 7 cells, Pseudo-X and from CHO cells, Pseudo-$X_2$. On SDS polyacrylamide gels, Pseudo-X and Pseudo-$X_2$ were approximately 130 kD and 140 kD, respectively.

The transfectea COS cells also formed rosettes around Sepharose beads coated with recombinant soluble ELAM1 (rsELAM1); and the resetting was cation dependent and was inhibited by both BB11 (anti-ELAM1 antibody) and α-CDX. COS cells and CHO cells transfected with pCDM8 alone (without the inserted clone) did not rosette rsELAM1 beads. Also, the COS and CHO cells transfected with clone 7.2 did not rosette to beads coated with bovine serum albumin.

We further characterized clone 7.2 and clone 1 by DNA sequence analysis and enzyme assays. Clone 1 encodes a polypeptide of 530 amino acids (encoded by nucleotides 174–1763 of FIG. 10 (SEQ ID NO:10)). Clone 7.2 encodes a 405-amino acid polypeptide (encoded by nucleotides 66–1280 in FIG. 9 (SEQ ID NO:9)). Using UWGCG Sequence Analysis Software Package (version 6.1, August 1989), we searched the NBRF Protein database (release Dec. 23, 1989) using the program FASTA for homology to other proteins. We also searched GenBank (release 63, March 1990) and EMBL (release May 19, 1989) using TFASTA. In these searches we found short regions (e.g., about 23 amino aclds) of homology to certain viral envelope proteins including Herpes simplex virus type 1, Dengue virus, yellow fever and other flaviviruses. In general the homology to known proteins was low, and we conclude that the polypeptides are novel.

The portion of the nucleotide sequence of clone 7.2 from nucleotide 9 to nucleotide 2162 (SEQ ID NO:9) is identical to the portion of the sequence of clone 1 from nucleotide 492 to nucleotide 2645 (SEQ ID NO:10). The first methionine of protein 7.2 corresponds to the methionine at amino acid 126 of protein 1. One explanation of this homology is that the two inserts represent different transcripts from the same DNA segment.

As we stated earlier, these clones do not code for CDX, Pseudo-X or Pseudo-$X_2$—the polypeptides they encode are not the correct size. Rather, the evidence strongly supports the conclusion that clone 7.2 and clone 1 encode 1,3-fucosyl transferases that glycosylate other proteins, such as CDX, Pseudo-X and Pseudo-$X_2$, in a way that makes them "visible" (i.e., recognized by or able to bind to) ELAM1 or α-CDX. First, the DNA sequences of clone 1 and clone 7.2 share several structural features with the DNA sequences of known glycosyl transferases. For example, genes encoding known glycosyl transferases commonly have consecutive methionine start sites and are capable of producing more than one mRNA transcript. As mentioned above, we have identified three mRNA transcripts that hybridize to clone 7.2, and clone 1 contains two codons that can serve as transcription start signals. Also, like known glycosyl transferases, the clones have multiple SP1 enhancer sites. The nucleotide sequences for these sites are GGGCGG or CCGCCC; clone 1 has five such sites. Also, like known glycosyl transferases, clones 7.2 and 1 are rich in guanine (G) and cytosine (C). For example, clone 1 is 75% GC rich in the 5' region of the gene and 60% GC rich in the 3' region of the gene. Glycosyl transferases in addition are typically class II membrane proteins, in which the membrane-spanning domain is near the amino terminus and the extracellular portion is near the carboxy terminus. Clone 1 and clone 7.2 encode a polypeptide having a hydrophobic region near the amino terminus. Glycosyl transferases also tend to have molecular weights between 40 kD to 60 kD; clone 1 encodes a polypeptide of about 59 kD and clone 7.2 encodes a polypeptide of about 46 kD. Finally, known glycosyl transferases usually have one to three N-glycosylation sites; clone 1 and clone 7.2 both encode two such sites.

Second, enzyme assays performed on extracts from CHO cells transfected with clone 7.2 revealed the presence of fucosyl transferases not expressed in untransformed cells. The assays tested the ability of the enzyme to link radioactively labelled fucose to an acceptor molecule. We performed the assays as follows.

We prepared assay samples containing 10 μl enzyme, 8 μl cocktail and 2 μl 10× acceptor. We prepared the enzyme by isolating about 1.5 million CHO cells transfected with clone 7.2 and lysing them by sonication for 15 seconds in 150 μl ice-cold 1% Triton X-100 in water. The cocktail contained 75 μM $^{14}$C-GDP fucose, 100 mM ATP, 500 mM L-fucose, 1 M $MnCl_2$ and 1 M cacodylate at pH 6.2. 10× acceptor contained, variously, 200 mM LacNAc, Lac-N-biose, or lactose, 250 mM phenyl-β-D-galectoside, or 50 mM 2'-fucosyllectose. We incubated the assay samples for 1 hour at 37° C. We stopped the reaction by addition of 20 μl ethanol. We diluted the sample with 560 μl water and centrifuged in an EPPENDORF centrifuge for 5 minutes at high speed.

We had prepared a DOWEX 1×2-400 column (Sigma Chemical Co.) to separate the unconverted $^{14}$C fucose-GDP from the converted. We loaded the matrix into a large column and washed it with 10 volumes of 1N NaOH, followed by 5 volumes of water, followed by 10 volumes of 5% concentrated formic acid. Then we repeated this wash cycle. We used this material to create small columns of 0.4 ml. We prepared the small columns for use by washing them with 10 volumes of water.

We loaded 200 μl of the sample onto the small column, collected the eluate, rinsed with 2 ml water and collected it into the eluate. We determined the radioactivity of this eluate by scintillation counting.

The results of this assay demonstrated that the induced enzyme is a 1,3-fucosyl transferase. (See Table 1.) The enzyme linked fucose to LacNAc, 2'-fucosyllactose and lactose, acceptors having GlcNAc or glucose moieties with free 3' hydroxyls. It did not link fucose to LacBiose, whose GlcNAc moiety does not have a free 3' hydroxyl, or phenyl-β-D-galectoside, the negative control acceptor. Control samples from untransfected cells showed only insignificant linking of fucose to these acceptors.

TABLE 1

Efficiency of Fucosylation

| Acceptor | picomoles mg Total protein · hr |
| --- | --- |
| LacNAc | 1110 |
| Lac-N-Biose | 76 |
| 2'-Fucosyllactose | 151 |
| Lactose | 290 |
| PhβDgal | Not detectable |

[The enzyme was freshly produced from transfected CHO cells.]

Therefore, both genetic and enzymatic evidence indicate that clone 7.2 and clone 1 encode 1,3-fucosyl transferases.

EXAMPLE XIII

ANTIBODIES RECOGNIZING MILAs FOR VCAM1

Polyclonal antisera were obtained from three mice that had been immunized with whole JURKAT cells. The serum from one mouse completely inhibited both RAMOS and JURKAT binding to 4 hour-induced HUVECs at room temperature. The sera from the two other mice completely inhibied RAMOS but only partially inhibited JURKAT binding under the same conditions. These data indicate that RAMOS and JURKAT share a MILA, and that JURKAT exhibits at least one other MILA not shared by RAMOS.

To prepare Moabs to lymphocyte MILAS, we immunized mice against whole live RAMOS and JURKAT cells and performed fusion of spleen cells from JURKAT-immunized mice and myeloma cells in the manner described in Example VIII, above. We are screening the resulting hybridomas by the method described in Example VII, which we used successfully to obtain monoclonal antibodies to CDX. To date we have screened the conditioned medium from about 260 hybridomas for inhibition of RAMOs adhesion to HUVEC treated with TNF for 24 hours. About 25 hybridomas have shown consistent partial inhibition of adhesion, and these are currently being subcloned for re-screening. Such antibodies may be used to both isolate and clone lymphocyte MILAs.

EXAMPLE XIV

EVIDENCE THAT VLA4 IS A VCAM1 LIGAND

We and other colleagues have performed several studies that demonstrate that VLA4 is a VCAM1 ligand and that VLA4 has separate binding sites for VCAM1 and fibronectin.

First, we showed that monoclonal antibodies against the subunits of VLA4 inhibited the attachment of VLA4-expressing cells to activated HUVECs and to COS cells transfected with VCAM1. VLA4 is composed of the subunits $β_1$ and $α^4$. (Hemler, 1988.) We found that a monoclonal antibody against $β_1$, designated B1E11, and goat anti-$β_1$ heteroantiserum completely inhibited the adhesion of RAMOS cells to activated HUVECs and transfected COS cells. A control antibody did not inhibit adhesion. Furthermore, a monoclonal antibody against the $α^4$ subunit, designated HP2/1, also blocked attachment of RAMOS to these cells. Similarly, these antibodies inhibited the attachment of the VLA4-expressing T lymphoblastoid cell line HPB-ALL.

Next, we showed that transfecting cells that do not ordinarily express VLA4 with $α^4$ enabled them to bind to VCAM1-expressing cells. We transfected two sets of K-562 erythroleukemic cells. One set was transfected with a cDNA coding for $α^4$. (Takada et al., 1989.) The other was transfected with $α^2$, which is not part of VLA4. (Takada and Hemler, 1989.) We showed that K-562 cells transfected with $α^4$ were now able to bind with a monolayer of VCAM1-transfected COS cells or TNF-activated HUVECs, but parent K-562 cells and K-562 $α^2$-transfected cells were not. In addition, monoclonal antibodies against $α^4$ or $β_1$ abolished the adhesion of $α^4$-transfected K-562 cells (that normally express the $β_1$ subunit) to these VCAM1-expressing cells.

Recent studies have shown that VH4 mediates cell attachment to human plasma fibronectin (FN) through the FN CS-1 site. (Wayner et al., 1989.) We have shown that the VLA4 binding site for VCAM1 is different than its binding site for FN. First, we found that preincubation of RAMOS cells or $α^4$-transfected K-652 cells with FN-40 (a soluble FN fragment) inhibited their binding with FN-40, but not with VCAM1-transfected COS cells or TNFα activated HUVECs. Second, we found that a monoclonal against VLA4, HP1/3, inhibited the binding of these cells to transfected COS cells or activated HUVECs, but not to FN-40.

EXAMPLE XV

INHIBITOR SCREENING

One can use ELAMs and their ligands in three basic adhesion assays to screen for potential inhibitors of adhesion, such as synthetic organic chemicals, natural fermentation products, peptides, etc.:

1. Cell-Cell Adhesion Assays

A first assay would test the ability of molecules to inhibit cell-cell adhesion. One could perform this assay in 96-well microtiter plates. First, one creates a cell line that stably expresses an ELAM, for example, as described in Example V. Then one plates out these cells and adds HL-60 cells. Inhibitors are identified by their ability to inhibit HL-60 binding to the ELAM-expressing cells. One would perform an assay exactly as described for screening for monoclonal antibodies to the ELAM ligand.

2. Cell-Adhesion Protein Assays

A second assay would test the ability of a small molecule to inhibit cell binding to ELAM itself. We have developed such an assay with rsELAM1 which works in 96 well microtiter plates. These plates, made of bacteriologic plastic (e.g. Linbro/Titertek #76-232-05®), are incubated with 0.5 $\mu$g per well of rsELAM1 in 50 $\mu$l of 15 mM sodium carbonate/35 mM sodium bicarbonate, pH 9.2, overnight at 4°. The plates are then blocked for one hour at room temperature with PBS containing 10 mg/ml of bovine serum albumin, and then adhesion assays performed as described in Example VIII using, e.g., HL-60 cells, $2\times10^6$/ml, 50 $\mu$l per well. Under these conditions HL-60 cells bind well to rsELAM1, providing a convenient microassay for screening. One would identify inhibitors by their ability to inhibit HL-60 binding to the plate. Alternatively, one could use an ELAM ligand in this assay, using as the probe a cell line that stably expresses an ELAM.

Another alternative assay in this category would examine the binding of a soluble ELAM or ELAM ligand to monolayers of cells stably expressing an ELAM ligand or ELAM, respectively. The soluble molecule would be labeled with a reporter group (e.g., radioactivity, fluorescent probe, enzyme, etc.)

3. Adhesion Protein-Adhesion Protein Assays

This assay tests the ability of a small molecule to inhibit the binding of an ELAM to its ligand. One of the two molecules in soluble form, e.g., a soluble ELAM, is immobilized in the wells of a 96-well microtiter plate, and adhesion is measured by binding of the other member of the pair, e.g., an ELAM ligand labeled with a reporter group.

In each of these three assays, one detects inhibitors by their ability to inhibit adhesion.

EXAMPLE XVI

VCAM1/IMMUNOGLOBULIN CONSTRUCT

We have prepared a DNA sequence which, on expression, produces an rsvcAM1/immunoglobulin fusion protein. The DNA sequence contains, from 5' to 3', VCAM1 domains 1–3 and the constant region of an $IgG_1$ heavy chain gene.

We produced a DNA fragment containing the VCAM1 domains 1–3 through nucleotide 1035 of FIGS. 2A–D (SEQ ID NO:13) by polymerase chain reaction (PCR). (Sambrook et al., 1989) The 3'-5' primer had the sequence 5' GAGCT-GAGG CCGCACCATG CCTGGGAAGA TG (SEQ ID NO:18). It is complementary to nucleotides 100–114 in FIG. 3 and contains the VCAM1 initiation codon and recognition sites for XhoI and NotI. The 5'-3' primer had the sequence 5' CTAGCTAGCG CGTTTACTT CAC (SEQ ID NO:19). It is complementary to nucleotides 1016–1035 in FIG. 2B (SEQ ID NO:3), at the end of domain 3, and contains an NheI recognition site. We used these primers to amplify a segment from a plasmid containing VCAM1 coding region of AM pcDM8 clone 41. The product of this process was a DNA sequence encoding VCAM1 domains 1–3. We digested this DNA fragment with XhoI and NheI and inserted it into pAB53, which we made as follows.

We digested pJOD-s (Example VIII) with SalI and inserted a cDNA sequence encoding human rsCD4. We called this plasmid pJOD-rsT4. We partially digested pJOD-rsT4 with PvuII and SphI to delete the fragment containing the two SV40 enhancer repeats in the SV40 promoter which control transcription of the DHFR cDNA. We religated the plasmid and designated it pJOD-rsT4 delta E. Then we digested pJOD-rsT4 delta E with NheI and NotI and inserted two DNA fragments: first, an NheI-HindIII linker containing a 5' mRNA splice site and second, a DNA fragment encoding the constant region of an IgG heavy chain gene. We obtained these fragments as follows.

We synthesized an NheI-HindIII linker having the following sequence:

5' splice

5' AGCTTAGGAC TCACCTTGGA AAG 3' (SEQ ID NO:21)

CCCAGGCATT TTAAG (SEQ ID NO:22)

The DNA sequence of an IgG heavy chain gene is described in Ellison et al. (1982). We isolated a fragment of this gene from an EMBL3 human genomic library (Example VIII) using an oligonucleotide probe. We digested the fragment with HindIII and NotI and isolated the fragment which included the constant heavy domains and the associated introns.

We ligated there two fragments into pJOD-rsT4 delta E and called the resulting plasmid pAB53. We digested pAB53 with XhoI and NheI to delete the rsT4 coding region. We inserted in its place the XhoI-NheI fragment encoding VCAM1 domains 1–3. We called this plasmid VCAM1-$IgC_1$.

An rsVCAM1/IgG fusion protein is expressed using this plasmid. The plasmid is transfected into CHO cells for stable expression. After transcription of this gene, the mRNA is spliced to remove the introns and upon translation, the cell produces rsVCAM-IgG fusion protein.

EXAMPLE XVII

INHIBITING VCAM1 EXPRESSION WITH AN ANTISENSE NUCLEIC ACID

We describe here an antisense nucleic acid against VCAM1 and a method for testing its ability to inhibit VCAM1 expression in induced HUVECs. An effective nucleic acid sequence for an antisense nucleic acid is one that is complementary to the coding region of the mRNA and, more particularly, to either the initiation codon, AUG, or the splice sites. (Marcus-Sekura, 1988.) Also, oligomers of about 15 nucleotides are most preferred. Thus, an effective antisense nucleic acid against VCAM1 is an oligomer with the DNA sequence 5' CCCAGGCATT TTAAG (SEQ ID NO:22). This would bind to nucleotides 94–108 of FIG. 2A (SEQ ID NO:3). (CAT is the antisense initiation codon.) This DNA sequence is synthesized, for example, by an automated DNA synthesizer.

The ability of this antisense nucleic acid to inhibit VCAM1 expression is tested as follows. HUVECs are grown to confluence as in Example V except that the serum used for cell growth would be heat inactivated for 30 min. at 60° to inactivate nucleases. Cells are preincubated with the oligomers at concentrations between 10 $\mu$M and 100 $\mu$M, most preferably the highest concentration having no effect on cell viability, for four to forty-eight hours. These ranges are required for effective inhibition. (Marcus-Sekura, 1988; Becker et al., 1989.) The HUVECs are then treated with 10 ng/ml TNF to induce VCAM1. About four hours later the presence of VCAM1 on the surface of the cells is tested by the adhesion assay.

EXAMPLE XVIII

A HAMMERHEAD RIBOZYME WHICH RECOGNIZES VCAM1 mRNA

A hammerhead-type ribozyme which recognizes VCAM1 mRNA is prepared according to the rules of Haselhoff and Gerlach (1988) as follows. First, a cleavage site on the target mRNA is identified. Hammerhead ribozymes cleave after the sequence 5' GUX, where X is any nucleotide. The first instance of this sequence in the coding region of VCAM1 mRNA is the sixth codon: 5' AUGCCUGGGA AGAUG-GUCGU GAUCCUU (SEQ ID NO:23). An appropriate recognition sequence includes about six nucleotides of the 5' and 3' regions flanking the cleavage site. An eighteen-base recognition sequence which contains the cleavage site is 5' AAGAUGGUCG UGAUCCUU (SEQ ID NO:24).

Then, one designs an RNA sequence for the ribozyme containing the recognition sequence and a sequence for the catalytic "hammerhead." Such a sequence is 5' AAG-GAUCACC UGAUGAGUCC GUGAGGACGA AAC-CAUCUU (SEQ ID NO:25). The sequence in brackets generates the catalytic "hammerhead" and the 5' and 3' flanking sequences are complementary to and bind to the recognition sequence. In a similar way, one can also design shorter recognition sequences or those for other cleavage sites in VCAM1 mRNA or the other ELAM or ELAM ligand mRNAs.

EXAMPLE XIX

ANTI-IDIOTYPIC ANTIBODIES RECOGNIZING ELAM1 LIGANDS

We have prepared anti-idiotypic antibodies against anti-ELAM1 antibodies that bind to the ligand of ELAM1 on HL-60 cells. We immunized rabbits with protein-A-purified CDB.BB11.BC6 monoclonal (Example V) emulsified 1:1 in complete Freund's adjuvant. Twenty-six days after immunization we bled the rabbits and analyzed the anti-sera for specific antibodies using FACS. We incubated the antibody preparation with either HL-60 cells, which express a ligand for ELAM1, or RAMOS cells, which do not. We found that this antibody preparation specifically bound to the HL-60 cells and not to the RAMOS cells, indicating that it contained antibodies that recognize the ELAM1 ligand. Control anti-serum did not react with either cell line.

EXAMPLE XX

EVIDENCE OF A NEW ELAM

The binding of U937 cells (which are monocyte-like) to induced HUVECs is not blocked by specific Moabs to the ELAM1, VCAM1, and/or ICAM1 pathways. U937 binding is blocked, however, by a monoclonal antibody to CD29, the $\beta_1$ integrin subunit. This leads us to postulate the existence of a new adhesion molecule on HUVECs that interacts with leukocytes via a $\beta^1$ integrin. The new molecule is induced with a time-course similar to VCAM1, remaining at maximal levels 48 hours after induction. We have generated a subtracted library from 48-hour TNF-treated HUVECS, using the methods previously described for the 2.5-hour IL-1 induced HUVEC subtracted sublibrary. We are attempting to clone the new molecule using the direct expression protocol described previously.

On Jun. 20, 1991 the microorganism deposits we identified herein were transferred from In Vitro International, Inc. to the American Type Culture Collection ("ATCC"), 10801 University Boulevard, Manassas, Va. 20110-2209, U.S.A. The ATCC assigned the following accession numbers:

IVI 10204—ATCC 68790
IVI 10205—ATCC HB 10879
IVI 10206—ATCC 68764
IV 10216—ATCC 68777
IVI 10217—ATCC 75123
IVI 10218—ATCC 75124
IVI 10220—ATCC HB 10880
IVI 10242—ATCC 68759
IVI 10255—ATCC 68741.

While we have described herein a number of embodiments of this invention, it is apparent that one of skill in the art could alter our procedures to provide other embodiments that utilize the processes and compositions of this invention. Therefore, one will appreciate that the scope of this invention is to be defined by the claims appended hereto rather than by the specific embodiments that we have presented by way of example.

CITED PUBLICATIONS

Arfors, K. -E., et al., "A Monoclonal Antibody to the Membrane Glycoprotein Complex CD18 Inhibits Polymorphonuclear Leukocyte Accumulation and Plasma Leakage In Vivo", *Blood*, 69, pp. 338–40 (1987)

Aruffo, A., and B. Seed, "Molecular Cloning of a CD28 cDNA by a High Efficiency COS Cell Expression System", *Proc. Natl. Acad. Sci. USA*, 84, pp. 8573–77 (1987)

Becker, D., et al., "Proliferation of Human Malignant Melanomas Is Inhibited by Antisense Oligodeoxynucleotides Targeted Against Basic Fibroblast Growth Factor," *EMBO J.*, 8, pp. 3685–91 (1989)

Benchimol, S., et al., "Carcinoembryonic Antigen, A Human Tumor Marker, Functions as an Intercellular Adhesion Molecule", *Cell*, 57, pp. 327–34 (1989)

Bevilacqua, M. P., and M. A. Gimbrone, "Inducible Endothelial Functions in Inflammation and Coagulation", *Seminars in Thrombosis and Hemostasis*, 13, pp. 425–33 (1987)

Bevilacqua, M. P., et al., "Interleukin 1 Acts on Cultured Human Vascular Endothelium to Increase the Adhesion of Polymorphonuclear Leukocytes, Monocytes, and Related Leukocyte Cell Lines", *J. Clin. Invest.*, 76, pp. 2003–11 (1985) ("Bevilacqua I")

Bevilacqua, M. P., et al., "Endothelial-Dependent Mechanisms of Leukocyte Adhesion: Regulation by Interleukin-1 and Tumor Necrosis Factor", *Leukocyte Emigration and Its Sequelae* (S. Karger A. G., Switzerland, 1987a), pp. 79–93 ("Bevilacqua II")

Bevilacqua M. P., et al., "Identification of an Inducible Endothelial-Leukocyte Adhogion Molecule", *Proc. Natl. Acad. Sci. USA*, 84, pp. 9238–42 (1987b) ("Bevilacqua III")

Bevilacqua, M. P., et al., "Endothelial Leukocyte Adhesion Molecule 1: An Inducible Receptor for Neutrophils Related to Complement Regulatory Proteins and Lectins", *Science*, 243, pp. 1160–5 (1989) ("Bevilacqua IV")

Breathnach, R. and P. Chambon, "Organization and Expression of Eucaryotic Split Genes Coding for Proteins", *Ann. Rev. Biochem.*, 50, pp. 349–83 (1981)

Brenan, M. and C. R. Parish, "Intracellular Flourescent Labelling of Cells for Analysis of Lymphocyte Migration", *J. Immun. Meth.*, 74, pp. 31–38 (1984)

Capon, D. J., et al., "Designing CD4 Immunoadhesins for AIDS Therapy," *Nature*, 337, pp. 525–31 (1989)

Carlsson, R., and C. Glad, "Monoclonal Antibodies into the '90s," *Bio/Technology*, 7, pp. 567–73 (June 1989)

Cate, R., et al., "Isolation of the Bovine and Human Genes for Mullerian Inhibiting Substance and Expression of the Human Gene in Animal Cells", *Cell*, 45, pp. 685–98 (1986)

Cech, T. R., "Ribozymes and Their medical Implications," *J. Amer. Med. Assn.*, 260, pp. 3030–4 (1988)

Chang et al., "Recombination Following Transformation of *Escherichia coli* by Heteroduplex Plasmid DNA Molecules," *Gene*, 29, pp. 255–61 (1984)

Colley, K. J., et al., "Conversion of a Golgi Apparatus Sialyltransferase to a Secretory Protein by Replacement of the $NH_2$-terminal Signal Anchor with a Signal Peptide", *J. Biol. Sci.* 264, pp. 17619–22 (1989).

Cotran, R. S., et al., "Induction and Detection of a Human Endothelial Activation Antigen In Vivo", *J. Exp. Med.*, 164, pp, 661–66 (1986)

Cotran, R. S., and J. S. Pober, "Endothelial Activation: Its Role in Inflammatory and Immune Reactions," in *Endthelial Cell Biology*, Simionescu and Simionescu, Eds., Plenum Press, New York (1988), pp. 3335–47

Dana, N., et al., "Mo1 Surface Glycoprotein: Structure, Function and Clinical Importance", *Pathol. Immunopathol. Res.*, 5, pp. 371–83 (1986)

Davis, M. M., "Substractive cDNA Hybridization and the T-Cell Receptor Gene", *Handbook of Experimental Immunology In Four Volumes*, 4th ed. Blackwell Scientific Publications, Oxford, England (1986), pp. 76.1–76.13

Davis, M. M., et al., "Cell Type-Specific cDNA Probes and the Murine I Region: The Localization and Orientation of Ad", *Proc. Natl. Acad. Sci. USA*, 81, pp. 2194–98 (1984)

Devereux, J., et al., "A comprehensive Set of Sequence Analysis Programs for the VAX," *Nucl. Acids Res.*, 12, pp. 387–95 (1984)

Duguid, J. R., et al., "Isolation of cDNAs of Scrapie-Modulated RNAs by Subtractive Hybridization of a cDNA Library", *Proc. Natl. Acad. Sci. USA*, 85, pp. 5738–42 (1988)

Dustin, M. L., and T. A. Springer, "Lymphocyte Function-Associated Antigen-1 (LFA-1) Interaction with Intercellular Adhesion Molecule 1 (ICAM1) Is One of at Least Three Mechanisms for Lymphocyte Adhesion to Cultured Endothelial Cells," *J. Cell. Biol.*, 107, pp. 321–33 (1988)

Dustin, M. L., et al., "Induction by IL1 and Interferon-gamma: Tissue Distribution, Biochemistry, and Function of a Natural Adherence Molecule (ICAM-1), *J. Immunol.*, 137, pp. 245–254 (1986)

Ellison, J. W., et al., "The Sequence of a Human Immunoglobulin C-gamma-1 Gene," *Nucl. Acids Res.*, 10, pp. 4071–79 (1982)

Feinberg, A. P., and B. Vogelstein, "A Technique for Radiolabeling DNA Restriction Endonuclease Fragments to High Specific Activity", *Anal. Biochem.*, 132, pp. 6–13 (1983)

Feinberg, A. P., and B. Vogelstein, "A Technique for Radiolabeling DNA Restriction Endonuclease Fragments to High Specific Activity", *Anal. Biochem.*, 137, pp. 266–67 (1984) (Addendum)

Fisher, R. A., et al., "HIV Infection Is Blocked In Vitro by Recombinant Soluble CD4", *Nature*, 331, pp. 76–78 (1988)

Gimbrone, M. A., "Culture of Vascular Endothelium", *Prog. Hemostasis Thromb.*, 3, pp. 1–28 (1976)

Goding, W., ed., *Monoclonal Antibodies: Principles and Practice*, (Academic Press, New York, 1983)

Goldenberg, D. M., "Targeted Cancer Treatment," *Immunology Today*, 10, pp. 286–88 (1989)

Gubler, U. and Hoffman, B. J., "A Simple and Very Efficient Method for Generating cDNA Libraries", *Gene*, 25, pp. 263–69 (1983)

Hambor, J. E., et al., "Functional Consequences of Anti-Sense RNA-Mediated Inhibition of CD8 Surface Expression in a Human T Cell Clone," *J. Exp. Med.*, 168, pp. 1237–45 (1988)

Harlan, J. M., "Leukocyte-Endothelial Interactions," *Blood*, 65, pp. 513–25 (1985) ("Harlan I")

Harlan, J. M., "Neutrophil-Mediated Vascular Injury", *Acta Med. Scand., Suppl.*, 715, pp. 123–29 (1987) ("Harlan II")

Harlan, J. M., et al., "The Role of Neutrophil Membrane Proteins in Neutrophil Emigration," in *Leukocyte Emigration and Its Sequelae*, H. Movat, ed. (S. Karger AG, Basel, Switzerland, 1987), pp. 94–104

Haselhoff, J., and W. L. Gerlach, "Simple RNA Enzymes with New and Highly Specific Endoribonuclease Activities," *Nature*, 334, pp. 585–591 (1988)

Hedrick, S. M., et al., "Isolation of cDNA Clones Encoding T Cell-Specific Membrane-Associated Proteins," *Nature*, 308, pp. 149–53 (1984)

Hemler, M. E., "Adhesion Protein Receptors on Hematopoietic Cells", *Immunol. Today*, 9, pp. 109–113 (1988)

Hemler, M. E., et al., "The VLA Protein Family (Characterization of Five Distinct Cell Surface Heterodimers Each with a Common 130,000 Molecular Weight β Subunit)," *J. Biol. Chem.*, 262, pp. 3300–09 (1987a)

Hemler, M. E., et al., "Characterization of the Cell Surface Heterodimer VLA-4 and Related Peptides," *J. Biol. Chem.*, 262, pp. 11478–85 (1987b)

Hirt, B., "Selective Extraction of Polyoma DNA from Infected Mouse Cell Cultures", *J. Mol. Biol.*, 26, pp. 365–69 (1967)

Hough, A. and L. Sokoloff, "Pathology", Chap. 4, *Rheumatoid Arthritis*, P. D. Ustinger, N. J. Zugifler, and Ehrlich, G. E., eds., (Lippencott, Philadelphia, 1985), pp. 49–69

Hunkapiller, T. and L. Hood, "Diversity of the Immunoglobulin Gene Superfamily", *Adv. Immunol.*, 44, pp. 1–63 (1989)

Huse, W. D., et al., "Generation of a Large Combinatorial Library of the Immunoglobulin Repertoire in Phage Lambda," *Science*, 246, pp. 1275–81 (1989)

Hynes, R. O., "Integrins: A Family of Cell Surface Receptors", *Cell*, 48, pp. 549–554 (1987)

Kalderon et al., *Nucl. Acids Res.*, 10, pp. 5161–71 (1982a)

Kennedy, R. C., et al., "Anti-idiotypes and Immunity," *Sci. Am.*, 255, pp. 48–56 (July 1986)

Kukowska-Latallo, J. F., et al., "A Cloned Human cDNA Determines Expression of a Mouse Stage-specific Embryonic Antigen and the Lewis Blood Group α(1,3/1,4) Fucosyltransferase", *Genes and Development*, 4, pp. 1288–1303 (1990)

Kurzinger, K., et al., "A Novel Lymphocyte Function-Associated Antigen (LFA-1): Cellular Distribution, Quantitative Expression, and Structure", *J. Immunol.*, 127, pp. 596–602 (1981)

Larsen, R. D., et al., "Molecular Cloning, Sequence, and Expression of a Human GDP-L-Fucose:β-D-Galactoside 2-α-L-Fucosyltransferase cDNA That Can Form the H Blood Group Antigen", *Proc. Natl. Acad. Sci. USA*, 87, pp. 6674–6678 (1990)

Lehrach, H., et al., "RNA Molecular Weight Determinations by Gel Electrophoresis under Denaturing Conditions, a Critical Reexamination", *Biochem.*, 16, pp. 4743–51 (1977)

Lenardo, M. J. and D. Baltimore, "NF-κB: A Pleiotropic Mediator of Inducible and Tissue Specific Gene Control," *Cell*, 58, pp.227–30 (1989)

Malech, H. L. and Gallin, J. I., "Neutrophils in Human Diseases", *N. Eng. J. Med.*, 317, pp. 687–94 (1987)

Maniatis, T., et al., Molecular Cloning: *A Laboratory Manual* (Cold Spring Harbor Laboratory, Cold Spring Harbor, N.Y., 1982)

Marcantonio, E. E., and R. O. Hynes, "Antibodies to the Conserved Cytoplasmic Domain of the Integrin β-1 Subunit React with Proteins in Vertebrates, Invertebrates and Fungi," *J. Cell. Biol*, 106, pp. 1765–72 (1988)

Marcus-Sekura, C. J., "Techniques for Using Antisense oligonucleotides to Study Gene Expression," *Anal. Biochem.*, 172, pp. 289–95 (1988)

Marlin, S. D., and T. A. Springer, "Purified Intercellular Adhesion Molecule-1 (ICAM-1) Is a Ligand for Lymphocyte Function-Associated Antigen 1 (LFA-1)," *Cell*, 51, pp. 813–9 (1987)

Maxam, A. and W. Gilbert, "Sequencing End-Labeled DNA with Base-Specific Chemical Cleavages", *Methods in Enzymol.*, 65, pp. 499–560 (1980)

Morinaga et al., "Improvement of Oligonucleotide-Directed Site-Specific Mutagenesis Using Double-Stranded Plasmid DNA," *Bio/Technology*, 2, pp. 636–9 (1984)

Oostra et al., "Transforming Activity of Polyoma Virus Middle-T Antigen Probed by Site-Directed Mutagenesis," *Nature*, 304, pp. 456–60 (1983)

Osborn, L., et al., "Tumor Necrosis Factor α and Interleukin 1 Stimulate the Human Immunodeficiency Virus Enhancer by Activation of the Nucleus Factor κB," *Proc. Natl. Acad. Sci. U.S.A.*, 86, pp. 2336–40 (1989)

Paulson, J. C., and K. J. Colley, "Glycosyltransferases: Structure, Localization, and Control of Cell Type-specific Glycosylation", *J. Biol. Chem.*, 264, pp. 17615–17618 (1989)

Peden, K. W. C. and D. Nathans, "Local Mutagenesis Within Deletion Loops of DNA Heteroduplexes," *Proc. Natl. Acad. Sci. U.S.A.*, 79, 7214–17 (1982)

Pober, J. S., et al., "Overlapping Patterns of Activation of Human Endothelial Cells by Interleukin 1, Tumor Necrosis Factor, and Immune Interferon," *J. Immunol.*, 137, pp. 1895–6 (1986)

Ross, R., "The Pathogenesis of Atherosclerosis—An Update", *N. Eng. J. Med*, 314, pp. 488–500 (1986)

Rothlein, R., et al., "A Human Intercellular Adhesion Molecule (ICAM-1) Distinct from LFA-1," *J. Immunol.*, 137, pp. 1270–4 (1986)

Ruoslahti, E., "Fibronectin and its Receptors", *Ann. Rev. Biochem.*, 57, pp. 375–413 (1988)

Sambrook, J., et al., "In Vitro Amplification of DNA by Polymerase Chain Reaction," Chapter 14 in *Molecular Cloning, A Laboratory Manual*, Cold Spring Harbor Laboratory Press, Cold Spring Harbor, N.Y. (1989)

Sandri-Goldin, R. M., et al., "High Frequency Transfer of Cloned Herpes Simplex Virus Type I Sequences to Mammalian Cells by Protoplast Fusion", *Molec. and Cell Biol.*, 1, pp. 743–52 (1981)

Sargent, T. D., "Isolation of Differentially Expressed Genes", *Methods in Enzymol.*, 152, pp. 423–47 (1987)

Sato, K., et al., "A Specific DNA Sequence Controls Termination of Transcription in the Gastrin Gene," *Molec. and Cell Biol.*, 6, pp. 1032–43 (1986)

Schneider, C., et al., "A One-Step Purification of Membrane Proteins Using a High Efficiency Immunomatrix" *J. Biol. Chem.*, 257, pp. 10766–69 (1982)

Seed, B., "An LFA-3 cDNA Encodes a Phospholipid-Linked Membrane Protein Homologous to Its Receptor CD2", *Nature*, 329, pp. 840–42 (1987)

Seed, B. and A. Aruffo, "Molecular Cloning of the CD2 Antigen, the T-cell Erythrocyte Receptor, by a Rapid Immunoselection Procedure", *Proc. Natl. Acad. Sci. USA*, 84, pp. 3365–69 (1987)

Skerra, A. and A. Plückthun, "Assembly of a Functional Immunoglobulin $F_v$ Fragment in *Escherichia coli*," *Science*, 240, pp. 1038–1043 (1988)

Simmons et al., "ICAM, an Adhesion Ligand of LFA-1, Is Homologous to the Neural Cell Adhesion Molecule NCAM," *Nature*, 331, pp. 624–47 (1988)

Smith, C. W., et al., "Cooperative Interactions of LFA-1 and Mac-1 with Intercellular Adhesion Molecule 1 in Facilitating Adherence and Transendothelial Cell Migration of Human Neutrophils in Vitro," *J. Clin. Invest.*, 83, pp. 2008–17 (1989)

Springer, T. A., et al., "The Lymphocyte Function-Associated LFA-1, CD2, and LFA-3 Molecules: Cell Adhesion Receptors of the Immune System", *Ann. Rev. Immunol.*, 5, pp. 223–252 (1987)

Staunton, D. E., et al., "Primary Structure of ICAM-1 Demonstrates Interaction Between Members of the Immunoglobulin and Integrin Supergene Families", *Cell.*, 52, pp. 925–33 (1988)

Subramani, S., et al., "Expression of the Mouse Dihydrofolate Reductase Complementary Deoxyribonucleic Acid in Simian Virus 40 vectors," *Molec. Cell. Biol.*, 1, pp. 854–64 (1981)

Takada, Y., and M. E. Hemler, "The Primary Structure of the VLA-2/Collagen Receptor $\alpha^2$ Subunit (Platelet GP Ia): Homology to Other Integrins and the Presence of a Possible Collagen-Binding Domain," *J. Cell. Biol.*, 109, pp. 397–407 (1989)

Takada, Y., et al., "The Primary structure of the α4 Subunit of VLA-4: Homology to Other Integrins and a Possible Cell-Cell Adhesion Function," *EMBO J.*, 8, pp. 1361–68 (1989)

Thomas, H. and Sikora, K., "Biological Approaches to Cancer Therapy", *J. Intl. Med. Res.*, 17, pp. 191–204 (1989)

Todd III, R. F., et al., "The Anti-Inflammatory Properties of Monoclonal Anti-Mo1 (CD11B/CD18) Antibodies in Vitro and in Vivo," in *Structure and Function of Molecules Involved in Leukocyte Adhesion*, Rosenthal et al., Eds., Springer-Verlag, N.Y. (1989) in press Vedder, N. B., et al., "A Monoclonal Antibody to the Adherence-Promoting Leukocyte Glycoprotein, CD18, Reduces Organ Injury and Improves Survival from Hemorrhagic Shock and Resuscitation in Rabbits", *J. Clin. Invest.*, 81, pp. 939–44 (1988)

von Heijne, G., "A Method for Predicting Signal Sequence Cleavage Sites", *Nucl. Acids Res.*, 14, pp. 4693–90 (1986)

Ward, E. S., et al., "Binding Activities of a Repertoire of Single Immunoglobulin Variable Domains Secreted from *Escherichia coli*," *Nature*, 341, pp. 544–46 (1989)

Wallis, W. J., and J. M. Harlan, "Effector Functions of Endothelium in Inflammatory and Immunologic Reactions," *Pathol. Immunopathol. Res.*, 5, pp. 73–103 (1986)

Wayner, E. A., et al., "Identification and Characterization of the Lymphocyte Adhesion Receptor for an Alternative Cell Attachment Domain in Plasma Fibronectin," *J. Cell. Biol.*, in press (1989)

Weintraub, H. M., "Antisense RNA and DNA," *Sci. Am.*, 262, pp. 40–46 (January 1990)

Wheeler, M. E., et al., "cultured Human Endothelial Cells Stimulated with Cytokines or Endotoxin Produce an Inhibitor of Leukocyte Adhesion", *J. Clin. Invest.*, 82, pp. 1211–18 (1988)

White, J. and D. Littman, "Viral Receptors of the Immunoglobulin Superfamily", *Cell*, 56, pp. 725–28 (1989)

Williams, A. and Barclay, A. N., "The Immunoglobulin Superfamily—Domains for Cell Surface Recognition", *Ann. Rev. Immunol.*, 6, pp. 381–405 (1988)

Wong, C. -H., "Enzymatic Catalysts in organic Synthesis", *Science*, 244, pp. 1145–1152 (1989)

Wysocki, L. J. and V. L. Sato, "'Panning' for Lymphocytes: A Method for Cell Selection", *Proc. Natl. Acad. Sci. USA*, 75, pp. 2844–48 (1978)

Yamasaki, K., et al., "Cloning and Expression of the Human Interleukin-6 (BSF-2/IFNB2) Receptor", *Science*, 241, pp. 825–28 (1988)

Young, R. A. and R. W. Davis, "Efficient Isolation of Genes by Using Antibody Probes", *Proc. Natl. Acad. Sci. USA*, 80, pp. 1194–98 (1983) ("Young I")

Young, R. A. and R. W. Davis, "Yeast RNA Polymerase II Genes: Isolation with Antibody Probes", *Science*, 222, pp. 778–82 (1984) ("Young II")

Foreign Patent Application

Hemler, M. E. and Y. Takada, "VLA Proteins," EP 330,506, published Aug. 30, 1989.

We claim:

1. A recombinant DNA molecule encoding an VCAM immunoglobulin fusion protein consisting of the DNA of SEQ. ID. NO:3 or SEQ. ID. NO:4 encoding VCAM1, VCAM1b or a fragment thereof that binds of VLA4 and a DNA sequence encoding the constant region of an immunoglobulin molecule.

2. A recombinant DNA molecule according to claim 1 comprising VCAM1 domains 1–3 and the constant regions of human immunoglobulin C-gamma-1.

3. A VCAM/immunoglobulin fusion protein encoded by the DNA molecule according to claim 1.

4. A recombinant DNA molecule encoding a VCAM/immunoglobulin fusion protein, wherein the VCAM of the fusion protein is encoded by a DNA molecule selected from the group consisting of the DNA sequence found in plasmid AM pCDM8 clone 41, ATCC Number 66784; and the DNA sequence found in plasmid 1E11 pCDM8, ATCC Number 68777.

5. The recombinant DNA molecule of claim 4 wherein the immunoglobulin of the fusion protein is encoded by a DNA sequence encoding a constant region of an immunoglobulin.

6. A fusion protein encoded by the DNA molecule of claim 4.

7. A recombinant DNA molecule encoding a soluble VCAM fusion protein, wherein the protein comprisis amino acids selected from the group consisting of:

(a) amino acids 1–217 of FIG. 2 (SEQ ID NO:5)
(b) amino acids 1–317 of FIG. 3 (SEQ ID NO:6)
(c) amino acids 1–606 of FIG. 2 (SEQ ID NO:5)
(d) amino acids 1–698 of FIG. 3 (SEQ ID NO:6).

* * * * *